US011090382B2

(12) United States Patent
Pleass et al.

(10) Patent No.: US 11,090,382 B2
(45) Date of Patent: Aug. 17, 2021

(54) MONOMERIC PROTEINS AND USES THEREOF

(71) Applicant: Liverpool School of Tropical Medicine, Liverpool (GB)

(72) Inventors: Richard Pleass, Liverpool (GB); Patricia Blundell, Liverpool (GB)

( * ) Notice: Subject to any disclaimer, the term of this patent is extended or adjusted under 35 U.S.C. 154(b) by 63 days.

(21) Appl. No.: 16/099,091

(22) PCT Filed: Apr. 28, 2017

(86) PCT No.: PCT/GB2017/051212
§ 371 (c)(1),
(2) Date: Nov. 5, 2018

(87) PCT Pub. No.: WO2017/191439
PCT Pub. Date: Nov. 9, 2017

(65) Prior Publication Data

US 2019/0151446 A1 May 23, 2019

(30) Foreign Application Priority Data

May 6, 2016 (GB) ..................................... 1607979

(51) Int. Cl.

| | |
|---|---|
| ***A61K 39/395*** | (2006.01) |
| ***A61K 47/68*** | (2017.01) |
| ***A61K 47/64*** | (2017.01) |
| ***C07K 16/46*** | (2006.01) |
| ***C07K 16/00*** | (2006.01) |
| ***A61P 37/06*** | (2006.01) |
| ***A61K 9/00*** | (2006.01) |
| ***C07K 16/18*** | (2006.01) |
| *A61K 39/00* | (2006.01) |

(52) U.S. Cl.
CPC ........ *A61K 39/3955* (2013.01); *A61K 9/0019* (2013.01); *A61K 47/6811* (2017.08); *A61P 37/06* (2018.01); *C07K 16/00* (2013.01); *C07K 16/18* (2013.01); *A61K 2039/54* (2013.01); *C07K 2317/30* (2013.01); *C07K 2317/35* (2013.01); *C07K 2317/40* (2013.01); *C07K 2317/41* (2013.01); *C07K 2317/52* (2013.01); *C07K 2317/60* (2013.01); *C07K 2319/00* (2013.01)

(58) Field of Classification Search
None
See application file for complete search history.

(56) References Cited

U.S. PATENT DOCUMENTS

2017/0088603 A1* 3/2017 Fallah-Arani ........... A61P 37/02
2018/0194856 A1* 7/2018 Griffin .................. C07K 16/32

FOREIGN PATENT DOCUMENTS

WO 0187982 A2 11/2001
WO 2015132364 A1 9/2015
WO 2017005767 A1 1/2017

OTHER PUBLICATIONS

Sorensen et al. Effect of the IgM and IgA Secretory Tailpieces on Polymerization and Secretion of IgM and IgG. The journal of Immunology, 1996, 156: 2858-2865.*

Hadlington et al. The C-terminal Extension of a Hybrid Immunoglobulin A/G Heavy Chain Is Responsible for Its Golgi-mediated Sorting to the Vacuole. Molecular Biology of the Cell. vol. 14, 2592-2602, Jun. 2003.*

Blundell et al, "Engineering the fragment crystallizable (Fc) region of human IgG1 multimers and monomers to fine-interactions with sialic acid-dependent receptors," Journal of Biological Chemistry, US, Jun. 15, 2017, 40 pages.

Brunke, et al, "Effect of a tail piece cysteine deletion on biochemical and functional properties of an epidermal growth factor receptor-directed IgA2 m(1) antibody," MABS, vol. 5, No. 6, Nov. 1, 2013, pp. 936-945.

Choi, et al, "Recombinant chimeric OKT3 scFv IgM antibodies mediate immune suppression while reducing T cell activation in vitro," Eur. J. Immunol, 2001, 31: 94-106.

Rouwendal et al, "A comparison of anti-HER2 IgA and IgG1 in vivo efficacy is facilitated by high N-glycan sialylation of the IgA," MABS, vol. 8, No. 1, Jan. 2, 2016, pp. 74-86.

Sitia et al, "Developmental regulation of IgM secretion: The role of the carboxy-terminal cysteine," Cell, Cell Press, US, vol. 60, No. 5, Mar. 9, 1990, pp. 781-790.

Sorensen et al, "Effect of the IgM and IgA secretory tailpieces on polymerization and secretion of IgM and IgG," The Journal of Immunology, The American Association of Immunologists, US, vol. 156, No. 8, Apr. 15, 1996, pp. 2858-2865.

* cited by examiner

*Primary Examiner* — Nianxiang Zou
(74) *Attorney, Agent, or Firm* — Brown Rudnick LLP; Adam M. Schoen

(57) ABSTRACT

Provided are proteins comprising two chimeric polypeptide chains; wherein each chimeric polypeptide chain comprises an Fc receptor binding portion comprising two immunoglobulin G heavy chain constant regions; and an immunoglobulin tailpiece region. The amino acid sequence and glycosylation of the tailpiece region of the proteins is adapted, as compared to the sequence and glycosylation of wild-type immunoglobulin, to inhibit polymerisation of the protein. The adaptation of the amino acid sequence may be the loss of a cysteine residue, for example the cysteine residue corresponding to residue 248 of SEQ ID NO: 1. The proteins may be used in intravenous immunoglobulin (IVIG) or subcutaneous immunoglobulin (SCIG) therapy. They may be used in the prevention or treatment of a disease mediated through binding of sialic acid-dependent receptors. Proteins of the invention may be used in the prevention and/or treatment of autoimmune or inflammatory diseases. The proteins may be conjugated to an immune modulator, and in such cases are suitable for vaccine use.

17 Claims, 21 Drawing Sheets

Specification includes a Sequence Listing.

Figure 1

| Fc-construct | Heavy chain composition | State* | DC-SIGN binding | C5b-9 deposition |
|---|---|---|---|---|
| Hexa-Fc | 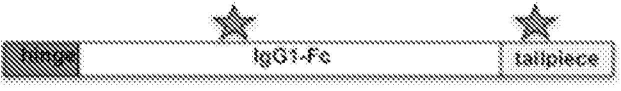 hinge IgG1-Fc tailpiece | P | + | + |
| N297A | hinge IgG1-Fc tailpiece | P | - | - |
| N563A | hinge IgG1-Fc tailpiece | HOP | + | + |
| N297A/N563A | hinge IgG1-Fc tailpiece | M | - | - |
| D221N | hinge IgG1-Fc tailpiece | P | +/- | +/- |
| D221N/N297A | hinge IgG1-Fc tailpiece | P | - | - |
| D221N/N563A | hinge IgG1-Fc tailpiece | HOP | +/- | +/- |
| D221N/N297A/N563A | hinge IgG1-Fc tailpiece | M | - | - |
| L448STOP | hinge IgG1-Fc | M/D | n.d. | n.d. |
| C575A | hinge IgG1-Fc tailpiece C=A | M | +/- | - |
| N563A/C575A | hinge IgG1-Fc tailpiece C=A | HOP ladders | + | + |

Figure 3
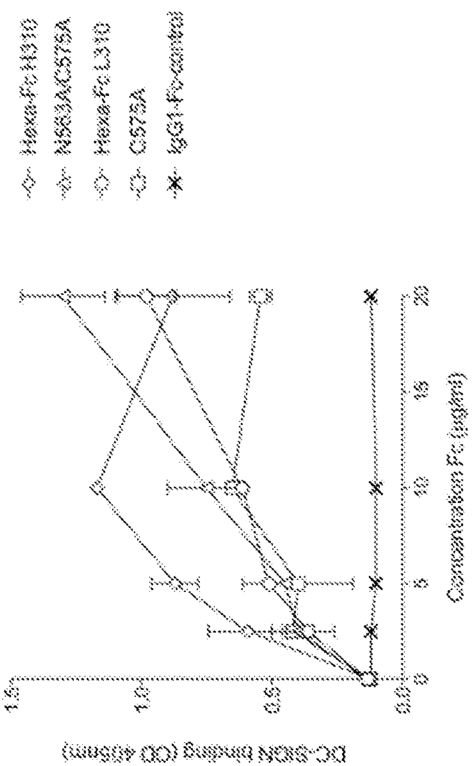
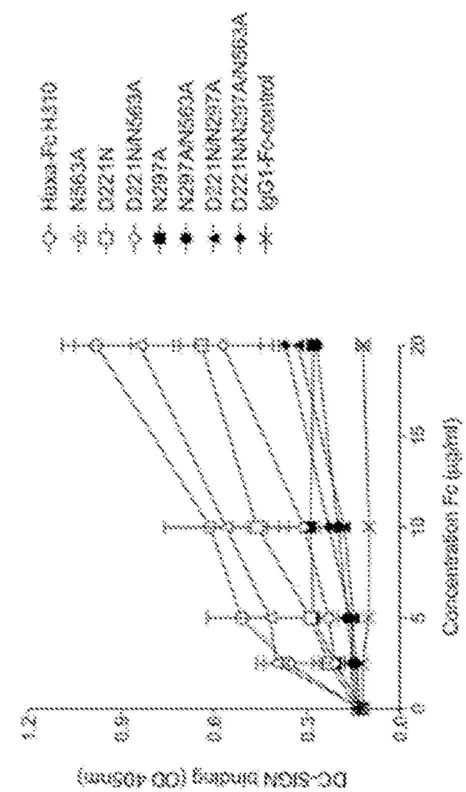

Figure 5
A)
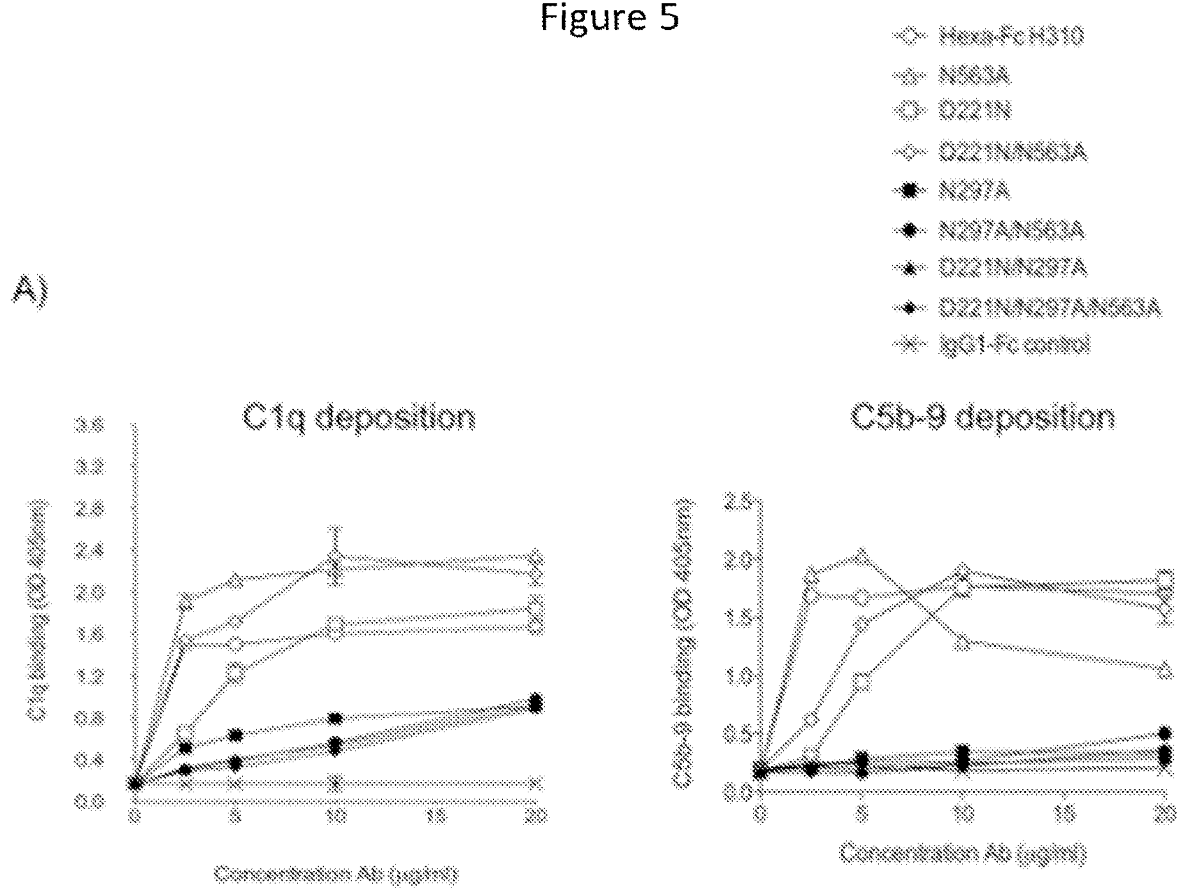
B)
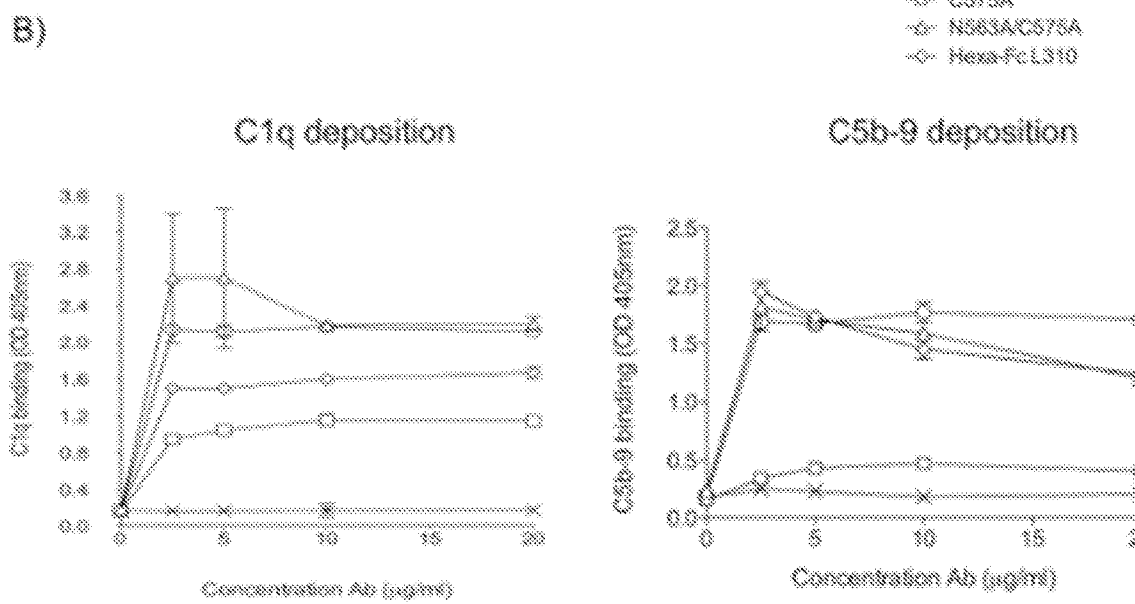

Figure 9

| Fc-construct | Heavy chain composition | State* | DC-SIGN binding | Siglec-1 binding | C5b-9 deposition |
|---|---|---|---|---|---|
| Hexa-Fc-IgM-tp | Hinge IgG1-Fc µ-tailpiece | O | + | + | + |
| Hexa-Fc-IgA-tp | Hinge IgG1-Fc µ-tailpiece | O | n.d | n.d | n.d |
| N297A | Hinge IgG1-Fc µ-tailpiece | O | - | n.d | - |
| N563A | Hinge IgG1-Fc µ-tailpiece | HOO | + | n.d | + |
| N297A/N563A | Hinge IgG1-Fc µ-tailpiece | M | - | - | - |
| L446STOP | Hinge IgG1-Fc | M,D | n.d. | n.d | n.d. |
| D221N | Hinge IgG1-Fc µ-tailpiece | O | +/- | + | +/- |
| D221N/N297A | Hinge IgG1-Fc µ-tailpiece | O | - | + | - |
| D221N/N563A | Hinge IgG1-Fc µ-tailpiece | HOO | +/- | +++ | +/- |
| D221N/N297A/N563A | Hinge IgG1-Fc µ-tailpiece | HOO | - | +++ | - |
| C575A | Hinge IgG1-Fc µ-tailpiece C=A | M,D | +/- | +++ | - |
| N563A/C575A | Hinge IgG1-Fc µ-tailpiece C=A | HOO ladders | + | n.d | + |
| D221N/N297A/C575A | Hinge IgG1-Fc µ-tailpiece C=A | M | n.d. | + | n.d. |
| D221N/N563A/C575A | Hinge IgG1-Fc µ-tailpiece C=A | HOO ladders | n.d. | + | n.d. |

Figure 11:
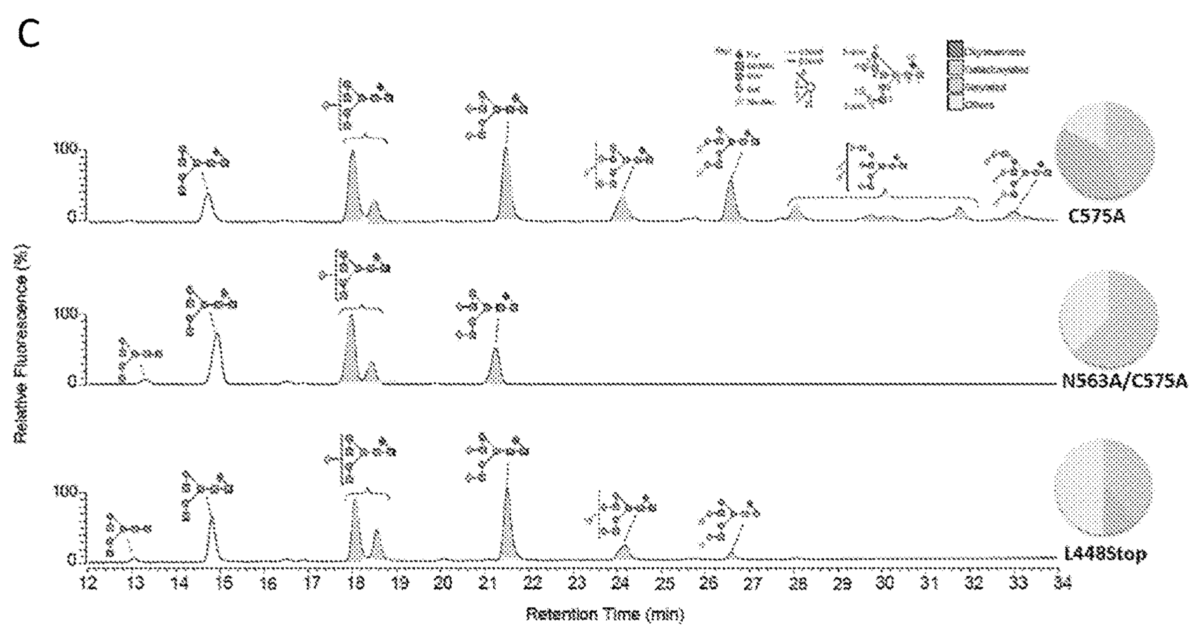

Figure 11
A
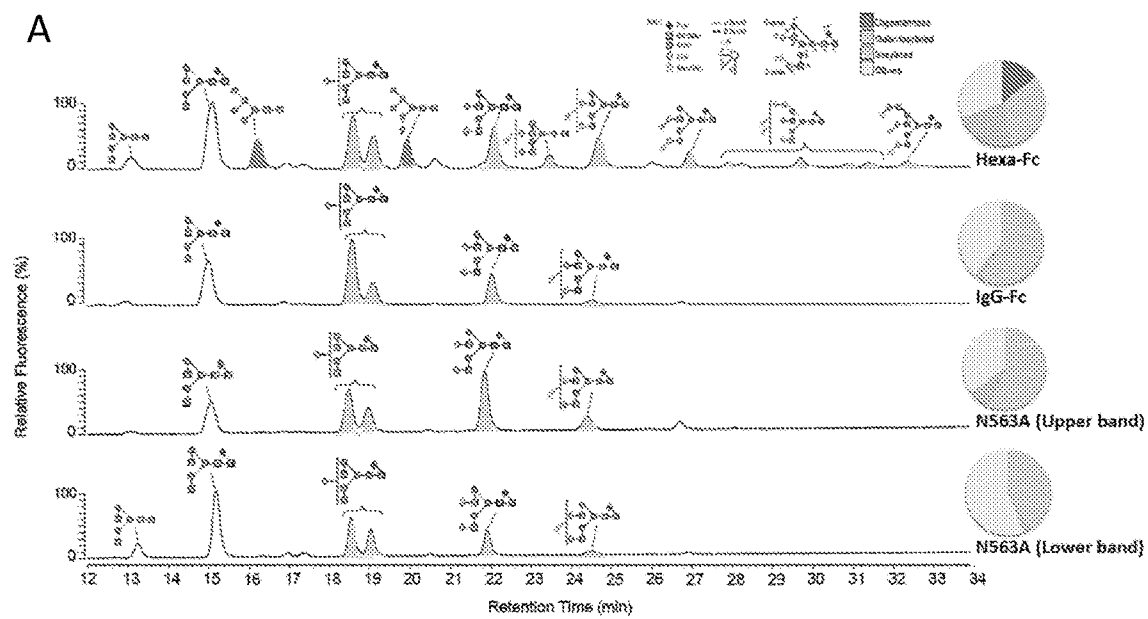
B
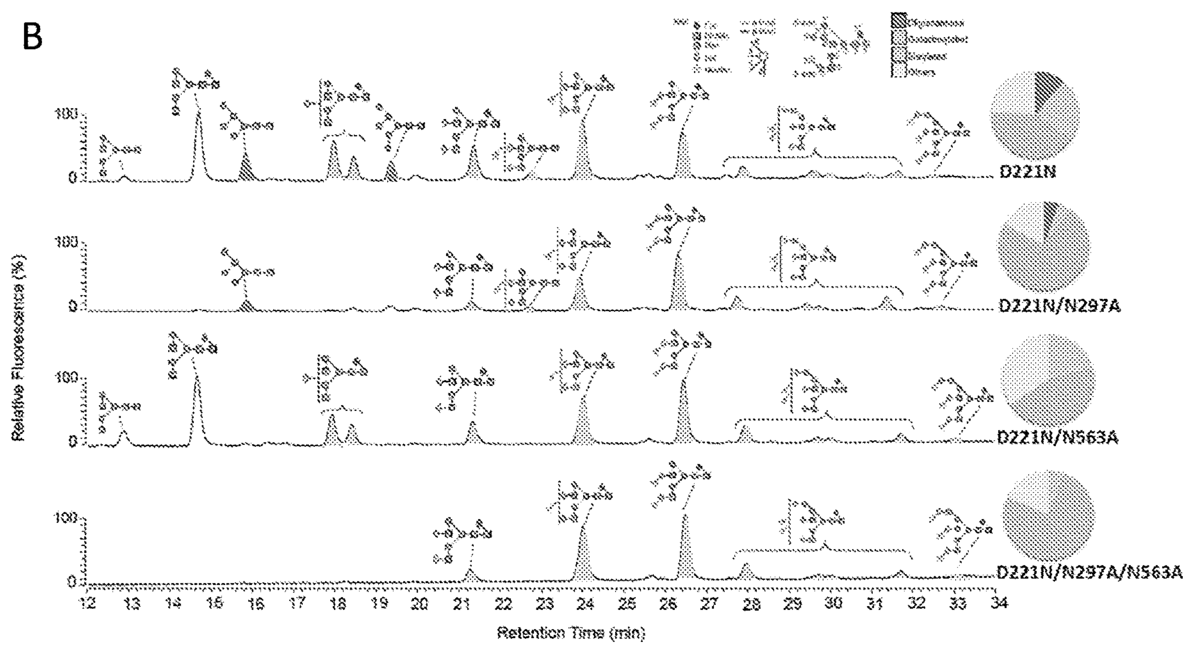

C

Figure 12
A)
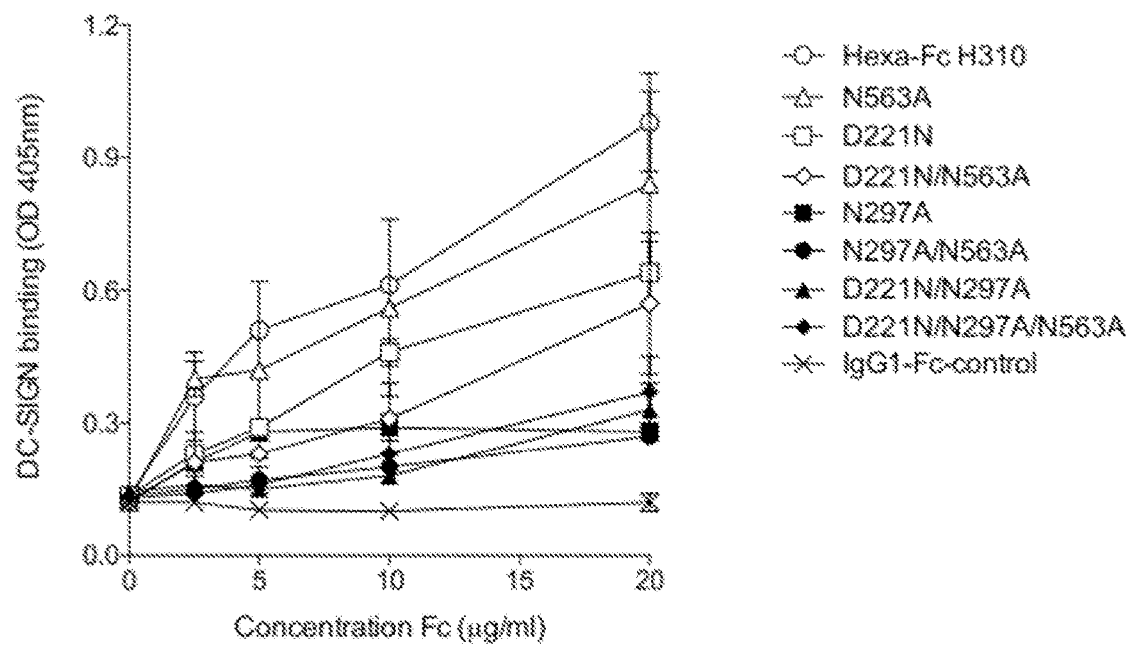
B)
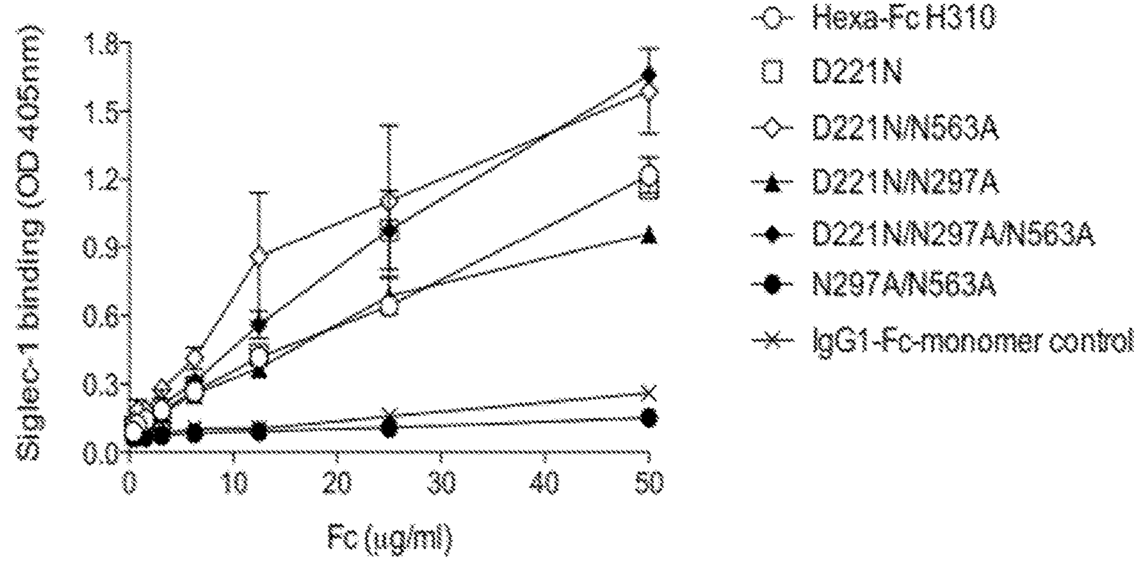

List of N-glycan structures detected by ESI-MS

| *m/z* | Ion[1] | Composition | | | | Structure[2] | Samples[3] | | | | | | | | | | |
|---|---|---|---|---|---|---|---|---|---|---|---|---|---|---|---|---|---|
| | | Hex | HexNAc | Fuc | NeuSAc | | Hexa-Fc | IgG-Fc | N563A (Upper band) | N563A (Lower band) | D221N | D221N/ N297A | D221N/ N563A | D221N/ N297A/ N563A | C575A | N563A/ C575A | L485Stop |
| 1330.2 | a | 5 | 2 | 0 | 0 | | Y | - | - | - | Y | Y | - | - | - | - | - |
| 1413.3 | a | 3 | 4 | 0 | 0 | | Y | - | - | Y | Y | - | Y | - | - | Y | Y |
| 1493.5 | a | 6 | 2 | 0 | 0 | | Y | - | - | - | Y | - | - | - | - | - | - |
| 1559.3 | a | 3 | 4 | 1 | 0 | | Y | Y | Y | Y | Y | - | Y | - | Y | Y | Y |
| 1721.3 | a | 4 | 4 | 1 | 0 | | Y | Y | Y | Y | Y | - | Y | - | Y | Y | Y |
| 1883.3 | a | 5 | 4 | 1 | 0 | | Y | Y | Y | Y | Y | Y | Y | Y | Y | Y | Y |
| 1986.7<br>2076.4 | c<br>b | 5 | 4 | 1 | 1 | | Y | Y | Y | Y | Y | Y | Y | Y | Y | - | Y |
| 1930.4 | b | 5 | 4 | 0 | 1 | | Y | - | - | - | Y | Y | - | - | - | - | - |
| 1183.3 | d | 5 | 4 | 1 | 2 | | Y | - | - | - | Y | Y | Y | Y | Y | - | Y |
| 1365.8 | d | 6 | 5 | 1 | 2 | | Y | - | - | - | Y | Y | Y | Y | Y | - | - |
| 1511.8 | d | 6 | 5 | 1 | 3 | | Y | - | - | - | Y | Y | Y | Y | Y | - | - |

1. Ions:

a = $[M+H_2PO_4]^-$ b = $[M-H]^-$ c = $[M-H+(H_2PO_4)]^{2-}$ d = $[M-H_2]^{2-}$

2. Symbols for monosaccharide residues: ▩ = GlcNAc, ◍ = mannose, ◇ = galactose, ◆ = fucose, ✲ = NeuSAc (sialic acid).

3. 'Y' indicates that the structure was present in the sample.

SEQUENCE LISTING

<160> NUMBER OF SEQ ID NOS: 17

<210> SEQ ID NO 1
<211> LENGTH: 249
<212> TYPE: PRT
<213> ORGANISM: Artificial Sequence
<220> FEATURE:
<223> OTHER INFORMATION: Reference protein, also designated “Hexa-Fc or HexaGard”

<400> SEQUENCE: 1

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Cys Leu Gln Asp Trp Leu Asn Gly
                85                  90                  95
```

```
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Leu Val Leu Gly Pro Pro Leu Tyr Asn Val Ser Leu Val
225                 230                 235                 240

Met Ser Asp Thr Ala Gly Thr Cys Tyr
                245


<210> SEQ ID NO 2
<211> LENGTH: 249
<212> TYPE: PRT
<213> ORGANISM: Artificial Sequence
<220> FEATURE:
<223> OTHER INFORMATION: Exemplary protein of the invention also
      designated “C248A”

<400> SEQUENCE: 2

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Cys Leu Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

```
His Glu Ala Leu His Asn His Tyr Thr Gln Lys Ser Leu Ser Leu Ser
    210                 215                 220

Pro Gly Lys Leu Val Leu Gly Pro Pro Leu Tyr Asn Val Ser Leu Val
225                 230                 235                 240

Met Ser Asp Thr Ala Gly Thr Ala Tyr
                245


<210> SEQ ID NO 3
<211> LENGTH: 747
<212> TYPE: DNA
<213> ORGANISM: Artificial Sequence
<220> FEATURE:
<223> OTHER INFORMATION: DNA sequence for C248A

<400> SEQUENCE: 3

gacaaaactc acacatgccc accgtgccca gcacctgaac tcctgggggg accgtcagtc      60

ttcctcttcc ccccaaaacc caaggacacc ctcatgatct cccggacccc tgaggtcaca     120

tgcgtggtgg tggacgtgag ccacgaagac cctgaggtca agttcaactg gtacgtggac     180

ggcgtggagg tgcataatgc caagacaaag ccgcgggagg agcagtacaa cagcacgtac     240

cgtgtggtca gcgtcctcac cgtctgcctc caggactggc tgaatggcaa ggagtacaag     300

tgcaaggtct ccaacaaagc cctcccagcc cccatcgaga aaaccatctc caaagccaaa     360

gggcagcccc gagaaccaca ggtgtacacc ctgcccccat cccgggagga gatgaccaag     420

aaccaggtca gcctgacctg cctggtcaaa ggcttctatc ccagcgacat cgccgtggag     480

tgggagagca atgggcagcc ggagaacaac tacaagacca cgcctcccgt gctggactcc     540

gacggctcct tcttcctcta cagcaagctc accgtggaca agagcaggtg gcagcagggg     600

aacgtcttct catgctccgt gatgcacgag gctctgcaca accactacac gcagaagagc     660

ctctccctgt ctccgggtaa attagtccta ggaccccccc tgtacaacgt gtccctggtc     720

atgtccgaca cagctggcac cgcctac                                         747


<210> SEQ ID NO 4
<211> LENGTH: 249
<212> TYPE: PRT
<213> ORGANISM: Artificial Sequence
<220> FEATURE:
<223> OTHER INFORMATION: Comparator protein "N236A/C248A"

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Cys Leu Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

```
Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Leu Val Leu Gly Pro Pro Leu Tyr Ala Val Ser Leu Val
225                 230                 235                 240

Met Ser Asp Thr Ala Gly Thr Ala Tyr
                245


<210> SEQ ID NO 5
<211> LENGTH: 747
<212> TYPE: DNA
<213> ORGANISM: Artificial Sequence
<220> FEATURE:
<223> OTHER INFORMATION: DNA sequence of the comparator protein
      "N236A/C248A"

<400> SEQUENCE: 5

gacaaaactc acacatgccc accgtgccca gcacctgaac tcctgggggg accgtcagtc      60

ttcctcttcc ccccaaaacc caaggacacc ctcatgatct cccggacccc tgaggtcaca     120

tgcgtggtgg tggacgtgag ccacgaagac cctgaggtca agttcaactg gtacgtggac     180

ggcgtggagg tgcataatgc caagacaaag ccgcgggagg agcagtacaa cagcacgtac     240

cgtgtggtca gcgtcctcac cgtctgcctc caggactggc tgaatggcaa ggagtacaag     300

tgcaaggtct ccaacaaagc cctcccagcc cccatcgaga aaaccatctc caaagccaaa     360

gggcagcccc gagaaccaca ggtgtacacc ctgcccccat cccgggagga gatgaccaag     420

aaccaggtca gcctgacctg cctggtcaaa ggcttctatc ccagcgacat cgccgtggag     480

tgggagagca atgggcagcc ggagaacaac tacaagacca cgcctcccgt gctggactcc     540

gacggctcct tcttcctcta cagcaagctc accgtggaca agagcaggtg gcagcagggg     600

aacgtcttct catgctccgt gatgcacgag gctctgcaca accactacac gcagaagagc     660

ctctccctgt ctccgggtaa attagtccta ggaccccccc tgtacgccgt gtccctggtc     720

atgtccgaca cagctggcac cgcctac                                         747


<210> SEQ ID NO 6
<211> LENGTH: 227
<212> TYPE: PRT
<213> ORGANISM: Artificial Sequence
<220> FEATURE:
<223> OTHER INFORMATION: Comparator protein "L448STOP"

<400> SEQUENCE: 6

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
```

```
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Cys Leu Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 7
<211> LENGTH: 748
<212> TYPE: DNA
<213> ORGANISM: Artificial Sequence
<220> FEATURE:
<223> OTHER INFORMATION: DNA sequence of the comparator protein "L448STOP"

<400> SEQUENCE: 7

```
gacaaaactc acacatgccc accgtgccca gcacctgaac tcctgggggg accgtcagtc     60

ttcctcttcc ccccaaaacc caaggacacc ctcatgatct cccggacccc tgaggtcaca    120

tgcgtggtgg tggacgtgag ccacgaagac cctgaggtca agttcaactg gtacgtggac    180

ggcgtggagg tgcataatgc caagacaaag ccgcgggagg agcagtacaa cagcacgtac    240

cgtgtggtca gcgtcctcac cgtctgcctc caggactggc tgaatggcaa ggagtacaag    300

tgcaaggtct ccaacaaagc cctcccagcc cccatcgaga aaaccatctc caaagccaaa    360

gggcagcccc gagaaccaca ggtgtacacc ctgcccccat cccgggagga gatgaccaag    420

aaccaggtca gcctgacctg cctggtcaaa ggcttctatc ccagcgacat cgccgtggag    480

tgggagagca atgggcagcc ggagaacaac tacaagacca cgcctcccgt gctggactcc    540

gacggctcct tcttcctcta cagcaagctc accgtggaca agagcaggtg gcagcagggg    600

aacgtcttct catgctccgt gatgcacgag gctctgcaca accactacac gcagaagagc    660

ctctccctgt ctccgggtaa atgagtccta ggaccccccc tgtacaacgt gtccctggtc    720

atgtccgaca cagctggcac ctgctact                                       748
```

<210> SEQ ID NO 8
<211> LENGTH: 19
<212> TYPE: PRT

<213> ORGANISM: Artificial Sequence
<220> FEATURE:
<223> OTHER INFORMATION: hinge sequence

<400> SEQUENCE: 8

Val Pro Ser Thr Pro Pro Thr Pro Ser Pro Ser Thr Pro Pro Thr Pro
1 5 10 15

Ser Pro Ser

<210> SEQ ID NO 9
<211> LENGTH: 6
<212> TYPE: PRT
<213> ORGANISM: Artificial Sequence
<220> FEATURE:
<223> OTHER INFORMATION: hinge sequence

<400> SEQUENCE: 9

Val Pro Pro Pro Pro Pro
1 5

<210> SEQ ID NO 10
<211> LENGTH: 15
<212> TYPE: PRT
<213> ORGANISM: Artificial Sequence
<220> FEATURE:
<223> OTHER INFORMATION: hinge region

<400> SEQUENCE: 10

Glu Pro Lys Ser Cys Asp Lys Thr His Thr Cys Pro Pro Cys Pro
1 5 10 15

<210> SEQ ID NO 11
<211> LENGTH: 12
<212> TYPE: PRT
<213> ORGANISM: Artificial Sequence
<220> FEATURE:
<223> OTHER INFORMATION: hinge region

<400> SEQUENCE: 11

Glu Arg Lys Cys Cys Val Glu Cys Pro Pro Cys Pro
1 5 10

<210> SEQ ID NO 12
<211> LENGTH: 12
<212> TYPE: PRT
<213> ORGANISM: Artificial Sequence
<220> FEATURE:
<223> OTHER INFORMATION: hinge region

<400> SEQUENCE: 12

Glu Ser Lys Tyr Gly Pro Pro Cys Pro Ser Cys Pro
1 5 10

<210> SEQ ID NO 13
<211> LENGTH: 4
<212> TYPE: PRT
<213> ORGANISM: Artificial Sequence
<220> FEATURE:
<223> OTHER INFORMATION: hinge region

<400> SEQUENCE: 13

Cys Pro Pro Cys
1

<210> SEQ ID NO 14
<211> LENGTH: 4

```
<212> TYPE: PRT
<213> ORGANISM: Artificial Sequence
<220> FEATURE:
<223> OTHER INFORMATION: hinge region

<400> SEQUENCE: 14

Cys Pro Ser Cys
1


<210> SEQ ID NO 15
<211> LENGTH: 4
<212> TYPE: PRT
<213> ORGANISM: Artificial Sequence
<220> FEATURE:
<223> OTHER INFORMATION: hinge region

<400> SEQUENCE: 15

Ser Pro Pro Cys
1


<210> SEQ ID NO 16
<211> LENGTH: 4
<212> TYPE: PRT
<213> ORGANISM: Artificial Sequence
<220> FEATURE:
<223> OTHER INFORMATION: hinge region

<400> SEQUENCE: 16

Leu Val Leu Gly
1


<210> SEQ ID NO 17
<211> LENGTH: 249
<212> TYPE: PRT
<213> ORGANISM: Artificial Sequence
<220> FEATURE:
<223> OTHER INFORMATION: Exemplary protein of the invention with
      additional glycosylation site in the hinge region (also referred
      to as "D1N/C248A" or "D221N/C575A")

<400> SEQUENCE: 17

Asn Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Cys Leu Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
```

-continued

```
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Leu Val Leu Gly Pro Pro Leu Tyr Asn Val Ser Leu Val
225                 230                 235                 240

Met Ser Asp Thr Ala Gly Thr Ala Tyr
                245
```

MONOMERIC PROTEINS AND USES THEREOF

RELATED APPLICATIONS

The present application is a 35 U.S.C. § 371 national phase application of PCT/GB2017/051212, filed Apr. 28, 2017, which claims the benefit of and priority to GB 1607979.0, filed May 6, 2016. The contents of each of the above are incorporated by reference herein in their entirety.

FIELD OF THE INVENTION

The present invention relates to proteins, and compositions comprising such proteins. The invention also relates to the medical uses of such proteins and compositions. In particular the proteins or compositions of the invention may be used in the prevention or treatment of autoimmune diseases or inflammatory diseases, or for the prevention or treatment of diseases mediated through binding of sialic acid dependent receptors, or as vaccines. The invention further relates to methods of preventing or treating autoimmune or inflammatory diseases, or diseases mediated through binding of sialic acid dependent receptors, using such proteins. The invention also relates to nucleic acids encoding the proteins, as well as methods of manufacturing the proteins.

BACKGROUND

Autoimmune diseases (ADs) are common and affect 50 million American citizens alone. Intravenous immunoglobulin (IVIG) treatment involves the administration of purified immunoglobulin G, and is one of the most common treatments of ADs, with Food and Drug Administration (FDA) approval for a diverse range of diseases like idiopathic thrombocytopenia (ITP), Kawasaki disease, Guillain-Barré, dermatomyositis, and chronic inflammatory demyelinating polyneuropathy.

As 70% of the global supply (worth $5 billion in 2012) of IVIG is now used to treat ADs, it is increasingly becoming unavailable to patients that need it most, in particular individuals with primary immune deficiency where IVIG is used as replacement therapy.

The worldwide consumption of IVIG has increased over 300 fold since 1980 and currently 100 ton are consumed per annum. Supplies of IVIG within the NHS and globally are critically limited, meaning that patients with an urgent need for the drug are routinely deprived of it. There are also significant clinical limitations resulting from its dependence on human donors for manufacture, and from the fact that <5% of injected IVIG (correctly glycosylated and/or oligomeric-Fc) is therapeutically active leading to a requirement for high doses (2 g/kg) when used in idiopathic thrombocytopenic purpura (ITP). Consequently, IVIG is expensive and adverse events due to excessive protein loading not uncommon.

Whereas some effector mechanisms of IgG relevant to autoimmune diseases may be F(ab')2-mediated, e.g. blocking/neutralization of receptors, cytokines, anaphylatoxins and pathogenic auto-antibodies via anti-idiotypic interactions, many anti-inflammatory functions are thought to be mediated by the Fc portion. They include FcRn saturation, blockade and modulation of FcγR expression, modulation of dendritic cell, B cells and T regulatory cell function and blockade/scavenging of complement components. IVIG suppresses harmful inflammation by engaging low-affinity inhibitory receptors and by forming immune-complexes (ICs) and/or dimers when injected in vivo that allow IVIG to interact with these receptors with greater strength (avidity), thus mediating more potent anti-inflammatory effects.

The problems noted above have led to a number of attempts to generate artificial agents, capable of expression on a large scale that can be used as replacements for human IgG in therapies, such as IVIG, for use in the treatment of autoimmune and inflammatory diseases.

Examples of such artificial agents that have been described to date include "SIFs" (selective immunomodulators of Fc-receptors), such as SIF-3, manufactured by Momenta, "stradomers" manufactured by Pfizer, and "hexa-Fc" an immunoglobulin-based hybrid protein produced by the current inventors. Each of the molecules produced in this manner has been designed to favour the formation of oligomeric structures that incorporate multiple Fc-receptor binding domains. This approach has been taken with a view to increasing avidity of binding of the artificial agents in the subjects to whom they are administered.

Cells carry various receptors that depend upon glycans comprising sialic acid for their binding. Examples of such sialic acid dependent receptors include SIGLEC-1 and SIGLEC-2. It is known that a range of diseases are mediated through binding to these sialic acid dependent receptors. For example, a number of infectious agents, such as retroviruses, bind to cells, and thus cause their associated infections, through binding to the cells' sialic acid dependent receptors.

SUMMARY OF THE INVENTION

In a first embodiment, the invention provides a protein comprising two chimeric polypeptide chains; wherein each chimeric polypeptide chain comprises an Fc receptor binding portion comprising two immunoglobulin G heavy chain constant regions; and an immunoglobulin tailpiece region;

wherein the amino acid sequence and glycosylation of the tailpiece region is adapted, as compared to the sequence and glycosylation of wild-type immunoglobulin, to inhibit polymerisation of the protein.

Suitably, the protein of the invention comprises a cysteine at a residue which corresponds to residue 89 of SEQ ID NO:1 (which in turn, corresponds to residue 309 of human IgG).

In a second embodiment, the invention provides a composition comprising a protein according to the first aspect of the invention, wherein at least 95% of the protein of the first aspect of the invention incorporated in the composition is in monomeric form.

The term "monomeric" as used in the context of the present invention, is considered in more detail elsewhere in this disclosure.

In a third aspect, the invention provides a protein in accordance with the first aspect of the invention for use as a medicament. The protein for use in the third aspect of the invention may be provided in the form of a composition in accordance with the second aspect of the invention.

Proteins or compositions of the invention may be used as medicaments in the prevention and/or treatment of autoimmune or inflammatory diseases. Suitable examples of such diseases are considered elsewhere in the specification.

Alternatively, proteins or compositions of the invention may be used as medicaments in the prevention and/or treatment of diseases mediated through the binding of sialic acid dependent receptors. In an embodiment, the receptor may be selected from the group consisting of: SIGLEC-1 and SIGLEC-2. Suitable examples of such diseases include retroviral infections, as considered elsewhere in the specification.

In a fourth aspect, the invention provides a method of preventing or treating an autoimmune or inflammatory disease, the method comprising providing a therapeutically effective amount of protein in accordance with the first aspect of the invention to a subject in need of such prevention or treatment. The subject may be a human subject.

In a fifth aspect, the invention provides a method of preventing or treating a disease mediated through binding of sialic acid dependent receptors, the method comprising providing a therapeutically effective amount of protein in accordance with the first aspect of the invention to a subject in need of such prevention or treatment. Suitably the subject is human. In an embodiment, the receptor may be selected from the group consisting of: SIGLEC-1 and SIGLEC-2. The disease may be an infection or an autoimmune disease. The disease may be a retroviral infection. The invention also provides corresponding medical uses.

The medical uses or methods of treatment of the third, fourth or fifth aspects of the invention may employ the proteins of the invention in intravenous immunoglobulin (IVIG) or subcutaneous immunoglobulin (SCIG) therapy.

In a sixth aspect, the invention provides a nucleic acid encoding a protein in accordance with the first aspect of the invention.

In a seventh aspect, the invention provides a method of producing a protein in accordance with the first aspect of the invention, the method comprising expressing a nucleic acid in accordance with the sixth aspect of the invention in a host cell.

DETAILED DESCRIPTION OF THE INVENTION

The invention is based upon the inventors' surprising finding that proteins of the invention, which remain monomeric in physiological conditions, are suitable for use in therapeutic applications such as IVIG and/or SCIG. This goes entirely against the expectations of those skilled in the art, since it had been widely considered desirable to produce oligomeric or polymeric Fc receptor-binding molecules, with a view to increasing the effectiveness of artificial agents generated for use in IVIG and/or SCIG.

The ability of a molecule to bind to glycan receptors, in particular Dendritic Cell-Specific Intercellular adhesion molecule-3-Grabbing Non-integrin (DC-SIGN), is associated with therapeutic utility in IVIG or SCIG. Previously it has been found that less than 5% of native, monomeric IgG molecules are correctly glycosylated in a way that allows them to interact with DC-SIGN, thus rendering these molecules unsuitable for therapeutic purposes.

Oligomeric or polymeric Fc receptor-binding molecules have increased avidity for DC-SIGN, which is advantageous in terms of their ability to bind to this receptor. However, oligomeric or polymeric Fc receptor-binding molecules previously described in the prior art have been shown to activate the complement cascade. This is a significant disadvantage in a potential therapeutic molecule, due to the risk of adverse consequences, such as anaphylactic shock.

The inventors have found that an adaptation of the amino sequence and glycosylation of the tailpiece region of the proteins of the invention, results in a monomeric protein glycosylated in a way which allows the protein of the invention to bind to DC-SIGN and sialic acid dependent receptors such as SIGLEC-1, and thus exert therapeutic utility in IVIG or SCIG. Furthermore, the proteins of the invention, surprisingly, do not lead to the activation of the complement cascade.

Proteins of the invention feature adaptation of the amino acid sequence and glycosylation of the tailpiece region, as compared to the sequence and glycosylation found in wild-type immunoglobulins from which they are derived, and these inhibit polymerisation of the hybrid proteins of the invention.

Suitably the adaptation of the amino acid sequence is loss of a cysteine residue. Suitably the adaptation may be loss of a single cysteine residue as compared to the wild-type sequence. Alternatively, the loss may be of multiple cysteine residues as compared to the wild-type sequence.

The loss may comprise loss of the cysteine corresponding to residue 248 of SEQ ID NO:1. In a suitable embodiment, a protein of the invention may also have loss of the cysteine residue corresponding to residue 89 of SEQ ID NO:1.

One or more cysteine residues may be lost, as compared to the sequence of the wild-type immunoglobulin tailpiece (such as the IgM tailpiece), or protein of SEQ ID NO:1, by their substitution or deletion. In a suitable embodiment of a substitution, a cysteine residue, such as the cysteine residue corresponding to residue 248 of SEQ ID NO:1, is replaced with a different amino acid. The cysteine residue by may replaced with any amino acid residue (for example an alanine, aspartic acid, glutamic acid, phenylalanine, glycine, histidine, isoleucine, lysine, leucine, methionine, asparagine, proline, glutamine, arginine, serine, threonine, valine, tryptophan or tyrosine residue). Suitably, cysteine residues, such as the cysteine residue corresponding to residue 248 of SEQ ID NO:1, is replaced with an alanine residue.

As referred to above, proteins of the invention also incorporate an adaptation of glycosylation of the tailpiece region that inhibits their polymerisation. The inventors have found that the glycans attached to glycosylation sites of proteins of the invention (as exemplified by SEQ ID NO:2) are larger than those on relevant control proteins (such as the protein of SEQ ID NO:1).

In a suitable embodiment, proteins of the invention may also comprise an adaptation of glycosylation of the immunoglobulin G derived sequence (such as the immunoglobulin G heavy chain constant region Cγ2) that inhibits their polymerisation. Such a glycosylation may be found, for example, at a residue corresponding to N77 of SEQ ID NO: 2. Proteins of the invention incorporating such an adaptation may be of particular utility in application requiring and making use of the ability to bind sialic acid-dependent receptors.

Suitably, the immunoglobulin G derived sequence of the proteins of the invention may comprise an artificial glycosylation site. Such an artificial glycosylation site may involve a substitution at a residue corresponding to residue D1 of SEQ ID NO:1 (in turn corresponding to D221 of human IgG). Suitably, such an artificial glycosylation may be obtained by an aspartic acid to asparagine substitution (for example a D1N substitution in SEQ ID NO: 1, corresponding to a D221N substitution of human IgG). An example of a protein of the invention comprising such a modification is shown in SEQ ID NO: 17, which corresponds to SEQ ID NO: 2, save for substitution of residue D1 with N. The protein of SEQ ID NO: 17 is a particularly useful example of a protein of the invention. It represents an embodiment that is highly suited to medical uses and methods in which it is desired for proteins of the invention to bind to sialic acid dependent receptors (for example to prevent or treat diseases mediated through binding of sialic acid dependent receptors).

It will be appreciated that artificial glycosylation constitutes further adaptation of the amino acid sequence and glycosylation of proteins of the invention to inhibit their polymerization.

Without wishing to be bound by any hypothesis, the inventors believe that the combination of loss of cysteine residues that would otherwise be able to form disulphide bridges between protein monomers, in combination with the capacity for larger glycans to be added at the glycosylation sites present within the monomers, significantly inhibits polymerisation of the proteins of the invention. As discussed elsewhere in the invention, these changes are sufficient to decrease the proportion of the proteins occurring in polymeric form from greater than 80% to less than <1%. The remarkable extent of this reduction could not be predicted prior to the results disclosed for the first time in the present specification.

Since polymerisation of the proteins of the invention is inhibited through a combined impact of adaptations of the amino acid sequence and glycosylation of the tailpiece, each of these individual modifications can be relatively minimal, while still achieving a marked inhibition in overall levels of polymerisation. The ability to utilise minimal departures from the wild-type sequences in this manner decreases the likelihood of the proteins of the invention inducing adverse immunogenic responses in subjects to whom they are administered, and this provides a further notable advantage of the proteins of the invention.

A further advantage of the modification of glycosylation observed is that, the larger and more complex glycans present are more likely to terminate in sialic acid (neuraminic acid). Glycans terminating in this manner are known to interact with DC-SIGN, and enhanced binding to DC-SIGN and SIGLEC-1 is observed in respect of proteins of the invention.

Additionally, the inventors have found that the introduction of an artificial glycosylation site is able to give rise to a protein with greater sialylation than a protein without such an artificial glycosylation site, and thus may yield a protein with greater efficacy for use in sialic acid dependent therapies.

In light of the above, it will also be appreciated that the presence of an artificial glycosylation site, in particular at residue 1 of SEQ ID NO: 2 (such as in the protein of SEQ ID NO:17), may enable binding of the proteins of the invention to sialic acid dependent receptors including SIGLEC-1, (also known as sialoadhesisn), as well as DC-SIGN.

Accordingly, such proteins may have a therapeutic effect in a number of diseases where binding to sialic acid dependent receptors, such as SIGLEC-1 may be desirable. For example, proteins of the invention may be used as medicaments in diseases in which it is desirable to compete with, and thereby inhibit or prevent, the binding of other molecules to sialic acid dependent receptors, such as SIGLEC-1. Merely by way of example, binding of proteins of the invention to sialic acid dependent receptors such as SIGLEC-1 may have a therapeutic effect in inhibiting retrovirus binding to these receptors, thus preventing or treating retrovirus infections (such as HIV or T-cell leukaemia virus infections).

The presence of an additional glycan at the artificial glycosylation site may also confer a further advantage as it may increase the protein's stability. Currently, in order to increase immunoglobulin stability, immunoglobulins are often chemically glycosylated, for example by in vitro enzymatic or non-enzymatic reactions. However, the presence of an artificial glycosylation site allows such modifications to be introduced by cells expressing the proteins, and thus may eliminate the need for this additional step of chemical glycosylation. As a result, the proteins of the invention may be produced in a more cost and time effective manner than traditional agents used in IVIG treatment.

Various aspects and embodiments of the invention will now be further described in the following paragraphs.

Exemplary Proteins of the Invention

An example of a protein of the invention is set out in SEQ ID NO: 2. A further exemplary protein of the invention is set out in SEQ ID NO: 17. A protein of the invention may comprise SEQ ID NO: 2 or SEQ ID NO: 17. In a suitable embodiment, a protein of the invention may consist of SEQ ID NO: 2 or SEQ ID NO: 17.

The chimeric polypeptide of SEQ ID NO: 2 comprises residues 221 to 447 of human IgG1 (corresponding to residues 1 to 227 of SEQ ID NO: 2) in combination with residues based upon, and adapted from, 558 to 576 of the tailpiece of human IgM (corresponding to residues 232 to 249 of SEQ ID NO: 2). The wild type immunoglobulin tailpiece sequence is adapted in SEQ ID NO: 2 to inhibit polymerisation of the protein of the invention.

SEQ ID NO: 17 corresponds directly to SEQ ID NO: 2, save for the presence of a D to N substitution at residue 1 of SEQ ID NO: 17. As discussed above, this substitution introduces a new glycosylation site in the protein of SEQ ID NO: 17.

It will be appreciated that in chimeric polypeptides, where the full IgG or IgM sequences are not present, numbering of residues based upon the full-length IgG or IgM molecules is no longer informative. Accordingly, we will also refer in this disclosure to a reference chimeric protein sequence, which is set out as SEQ ID NO: 1. This sequence represents a single chimeric polypeptide chain. When referring to this sequence, Cys575 of the full length IgM sequence is renumbered as Cys248 of the fusion protein (the 248$^{th}$ residue of SEQ ID NO: 1).

For the avoidance of doubt, a protein consisting of chimeric protein chains having the sequence set out in SEQ ID NO: 1 will not constitute a protein of the invention, since it will not incorporate the requisite adaptations to inhibit polymerisation.

The inventors' have surprisingly found, that SEQ ID NO: 2 may encode monomeric proteins of two different sizes, specifically ~53 kDa and ~58 kDa. Without wishing to be bound to any hypothesis, the inventors' believe that differentially glycosylated at residues N77 of SEQ ID NO: 2 (corresponding to N297 of human IgG1) in the immunoglobulin G heavy chain constant region (such as Cγ2 domain), and at N236 of SEQ ID NO: 2 (corresponding to N563 of human IgM) in the immunoglobulin tailpiece give rise to the two sizes of monomeric proteins.

In addition to the Fc receptor binding portion and the tailpiece region, the proteins of the invention may further comprise a hinge region and/or a spacer region.

In a suitable embodiment, the proteins of the present invention may be conjugated to a therapeutic payload. Suitable therapeutic payloads are described elsewhere in this specification. Suitably the payload may be conjugated to the Fc receptor binding portion of the protein of the invention. Alternatively, it may be conjugated to the hinge region of the protein of the invention.

In a suitable embodiment, a hinge region may be located at the N-terminus of the Fc receptor binding portion. The hinge region may be a natural or synthetic hinge region.

In a suitable embodiment, the hinge region is natural. A natural hinge region is one that is naturally found between the Fc and Fab portion of an antibody. A natural hinge region may be derived from the same species as the Fc receptor binding portion. Alternatively, it may be derived from a different species.

In a suitable embodiment, a natural hinge region may be derived from an antibody of the same class or subclass as the Fc receptor binding portion. Alternatively, it may be derived from an antibody of a different class or subclass as the Fc receptor binding portion.

In a suitable embodiment, the hinge region is derived from IgG1. More suitably, the hinge region may be derived from human IgG1. By way of example, in the protein of the invention according to SEQ ID NO:2, comprises a hinge region derived from human.

In a suitable embodiment, the N-terminus of the hinge region may be glycosylated in a way so as to inhibit polymerisation of the protein of the present invention. Suitably, the glycosylation may be at a position corresponding to residue 1 of SEQ ID NO:1 or SEQ ID NO: 2 (as exemplified by the protein of SEQ ID NO:17). Glycosylation of the hinge region may be beneficial as it may result in an exposed glycan, which may modify the function of the protein of the invention. By way of example, and as further explained in the Examples section of this description, glycosylation of the hinge region may reduce the protein's interactions with Fc-gamma receptors, while increasing interactions with sialic acid dependent receptors such as SIGLEC-1.

In another embodiment, the hinge region is synthetic. A synthetic hinge region is one that differs in length or sequence from a hinge region which is found naturally. By way of example, the difference in length between a synthetic and natural hinge region may be as a result of the addition or deletion of residues in the synthetic hinge region (for example addition or deletion of cysteine residues). A difference in sequence between a synthetic and natural hinge region may be as a result of a substitution of one or more residues in the synthetic hinge region (for example substitution of a cysteine residue with another residue such as serine or alanine).

In a suitable embodiment, a hinge region may be at least one, at least two, at least three, at least four, at least five, at least six, at least seven, at least eight, at least nine, at least ten, at least fifteen, at least twenty, at least twenty five, at least thirty, or more amino acid residues long.

By way of example and not limitation, a protein of the invention may comprise a hinge region, wherein the hinge region has a sequence selected from the group consisting of: VPSTPPTPSPSTPPTPSPS (SEQ ID NO: 8), VPPPPP (SEQ ID NO: 9), EPKSCDKTHTCPPCP (SEQ ID NO: 10), ERKCCVECPPCP (SEQ ID NO: 11), ESKYGPPCPSCP (SEQ ID NO: 12), CPPC (SEQ ID NO: 13), CPSC (SEQ ID NO: 14), and SPPC (SEQ ID NO: 15). Other suitable natural and synthetic hinges will be known to those skilled in the art.

The presence of a hinge region may be especially desirable in embodiments where the protein of the invention is conjugated to a therapeutic payload. It will be appreciated that such a hinge region may increase the distance between the Fc receptor binding portion and the therapeutic payload, if present. When the therapeutic payload is conjugated to the protein of the invention, increased distance between the Fc receptor binding portion and the therapeutic payload may be desirable in order to provide sufficient space for the attachment of a glycan molecule to a glycosylation site. Suitably, the hinge region provides space for the attachment of a glycan molecule to an artificial glycosylation site (for example at residue 1 of SEQ ID NO: 1, as found in SEQ ID NO:17).

It will be also be appreciated, that the presence of a hinge region may be desirable for the insertion and/or attachment of an additional N-linked glycosylation site in the protein of the invention.

As touched upon above, the protein of the invention may comprise a spacer region. Suitably, the spacer region may be between the Fc receptor binding portion and the tailpiece region.

A suitable spacer region may be at least one, at least two, at least three, at least four, at least five, at least six, at least seven, at least eight, at least nine, at least ten, or more amino acid residues long. More suitably, the spacer region may be four amino acid residues long. In the exemplary protein of the invention as set out by SEQ ID NO: 2, the spacer region may be found at residues 228 to 231.

Suitably the spacer region may have the sequence LVLG (SEQ ID NO: 16).

The presence of a spacer region may improve the disposition of the tailpiece carbohydrate (for example corresponding to amino acid residue N236 of the protein if the invention as set out in SEQ ID NO:1 or SEQ ID NO:2) and thus improve interactions with glycan receptors without compromising interactions mediated through the Fc constant domains.

Adaptation of Tailpiece Amino Acid Sequence to Inhibit Polymerisation

Immunoglobulin tailpieces for incorporation in the proteins of the invention may be based upon any immunoglobulin molecule. Suitably a tailpiece may be based upon the tailpiece of an immunoglobulin selected from the group consisting of: IgM, IgA, and IgE.

A tailpiece based upon that of IgM is particularly suitable for incorporation in the proteins of the invention. Exemplary adaptations are described herein with reference to the IgM tailpiece (which is incorporated in the reference protein of SEQ ID NO: 1, and the exemplary proteins of the invention of SEQ ID NO: 2 or SEQ ID NO:17). It will be appreciated that tailpieces of other immunoglobulins may be adapted at residues corresponding to those exemplified in respect of IgM. Furthermore, tailpieces derived from immunoglobulins other than IgM may be adapted in the same manner as described in respect of IgM.

Tailpieces suitable for incorporation in the proteins of the invention may, as long as they comprise relevant adaptations, share at least 55% identity with a native immunoglobulin tailpiece, such as the IgM tailpiece. Indeed a suitable tailpiece, as long as suitably adapted, may share at least 55%, at least 65%, at least 75%, at least 80%, at least 85%, at least 90%, at least 95% or more identity with the sequence of a corresponding portion of a native immunoglobulin tailpiece.

In particular, tailpieces suitable for incorporation in the proteins of the invention may, as long as they comprise the adaptations found in SEQ ID NO:2, share at least 55% identity with the IgM-derived sequences of SEQ ID NO: 2 (i.e. amino acid residues 232-249 of SEQ ID NO: 2). Suitably a tailpiece for incorporation in a protein of the invention may share at least 55%, at least 65%, at least 75%, at least 80%, at least 85%, at least 90%, at least 95% or more identity with residues 232-249 of SEQ ID NO:2.

For the avoidance of doubt, a protein that comprises the wild-type amino acid sequence of an immunoglobulin tailpiece, such as the IgM tailpiece, without any alteration, whether by substitution or deletion, will not constitute a protein of the invention.

Adaptation of Tailpiece Glycosylation to Inhibit Polymerisation

Proteins of the invention must include at least one glycosylation site, and may include two or more glycosylation sites, within the tailpiece. These may be naturally occurring glycosylation sites retained from the native immunoglobulin tailpiece sequence. Alternatively, the proteins of the invention may include artificially introduced glycosylation sites in the tailpiece region, or combinations of naturally occurring and artificial sites. The inventors have found that when glycosylation sites are absent (such as in the control protein of SEQ ID NO:4) inhibition of polymerisation is much reduced, and so polymer formation increases.

For the purposes of the present disclosure, a protein in which the glycosylation of the immunoglobulin tailpiece, such as the IgM tailpiece, is not altered as compared to the glycosylation observed in respect of the wild-type tailpiece, will not constitute a protein of the invention.

Adaptation of Hinge Region Amino Acid Sequence to Inhibit Polymerisation

Hinge regions for incorporation in the proteins of the invention may be based upon any immunoglobulin molecule. Suitably a hinge region be based upon the hinge region of an immunoglobulin selected from the group consisting of: IgG, IgA, IgE, IgD and IgM. More suitably, the hinge region of an IgG immunoglobulin may be selected from the group consisting of IgG1, IgG2, IgG3 and IgG4.

A hinge region based upon that of immunoglobulin IgG1 is particularly suitable for incorporation in the proteins of the invention. Exemplary adaptations of a hinge region are described herein with reference to the IgG1 hinge region (which is incorporated in the reference protein of SEQ ID NO: 1, and the exemplary proteins of the invention of SEQ ID NO: 2 and SEQ ID NO: 17).

It will be appreciated that hinge regions of other IgG immunoglobulins may be adapted at residues corresponding to those exemplified in respect of IgG1. Furthermore, hinge regions derived from immunoglobulins other than IgG may be adapted in the same manner as described in respect of IgG1.

Hinge regions suitable for incorporation in the proteins of the invention may, as long as they comprise relevant adaptations, share at least 55% identity with a native immunoglobulin hinge region, such as the IgG hinge region. Indeed a suitable hinge region, as long as suitably adapted, may share at least 55%, at least 65%, at least 75%, at least 80%, at least 85%, at least 90%, at least 95% or more identity with the sequence of a corresponding portion of a native hinge region.

In particular, hinge regions suitable for incorporation in the proteins of the invention may, as long as they comprise the adaptations found in SEQ ID NO:2, share at least 55% identity with the IgG hinge region derived sequences of SEQ ID NO: 2. Suitably a hinge region for incorporation in a protein of the invention may share at least 55%, at least 65%, at least 75%, at least 80%, at least 85%, at least 90%, at least 95% or more identity with the residues of the hinge region of SEQ ID NO:2.

Adaptation of Hinge Region Glycosylation to Inhibit Polymerisation

Proteins of the invention may include a glycosylation site within the hinge region. The glycosylation site may be a naturally occurring glycosylation site retained from a native immunoglobulin hinge region sequence. Alternatively, the proteins of the invention may include an artificially introduced glycosylation site in the hinge region, or combinations of naturally occurring and artificial sites. The inventors have found that when glycosylation sites are absent (such as in the control protein of SEQ ID NO: 4) inhibition of polymerisation is much reduced, and so polymer formation may increase.

Inhibition of Polymerisation of Proteins of the Invention

In proteins of the invention, the amino acid sequence and glycosylation of the tailpiece region, and optionally, the hinge region is adapted, when compared to the sequence and glycosylation of the corresponding wild-type tailpiece (such as the IgM tailpiece), and native hinge region respectively, to inhibit polymerisation of the protein. Inhibition of polymerisation of such proteins may be demonstrated by either a decrease in the proportion of protein present in a polymeric form, or an increase in the proportion of the protein that is present in a monomeric form. This may be assessed with reference to the proportion of polymeric or monomeric protein found in an appropriate control protein. Such an appropriate control protein may comprise a wild-type tailpiece, for example the IgM tailpiece, and optionally, may comprise a native hinge region.

In a control protein (SEQ ID NO:1) lacking the adaptations of the proteins of the invention (as exemplified by SEQ ID NO:2) monomers make up less than 20% of the total protein. In contrast, the inventors have found that more than 90% of a protein of the invention (such as SEQ ID NO:2) is present in monomeric form under physiological conditions.

Thus in the case of a protein, such as a protein of the invention as exemplified by SEQ ID NO:2 or SEQ ID NO:17, in which the amino acid sequence and glycosylation of the tailpiece region and hinge region are adapted as compared to the wild type sequence, the adaptation may be demonstrated to be one that inhibits polymerisation if 90% or more of the protein is present in monomeric form under physiological conditions. Indeed, in a suitable embodiment, inhibition of polymerisation may result in 95% or more of a protein being present in monomeric form, for example, 96% or more, 97% or more, 98% or more, or even 99% or more. In a suitable embodiment, inhibition of polymerisation may result in substantially all of a protein of the invention being present in monomeric form under physiological conditions.

Suitable methods by which the proportion of polymeric or monomeric protein in a sample may be determined are described in the Examples section later in this specification. Briefly, these include size-exclusion chromatography and SDS-PAGE acrylamide gradient gels.

IgG Sequences Suitable for Use in the Proteins of the Invention

The proteins of the invention incorporate two immunoglobulin G heavy chain constant regions. In a suitable embodiment, the immunoglobulin G heavy chain constant regions employed in the monomeric proteins of the invention are derived from an immunoglobulin selected from the group consisting of: IgG1; IgG2; IgG3; and IgG4. In particular, the immunoglobulin G heavy chain constant regions may be derived from IgG1.

It will be appreciated that as long as they meet the requirement of forming an Fc receptor binding portion, the immunoglobulin G heavy chain constant regions utilised in proteins of the invention may include an alteration in their sequence as compared to the native sequences from which they are derived. Merely by way of example, a suitable protein of the invention may utilise IgG derived sequences that share at least 60%, at least 70%, at least 75%, at least 80%, at least 85%, at least 90%, at least 95%, at least 96%, at least 97%, at least 98%, or at least 99% sequence identity with the relevant native IgG sequence from which they are derived.

Monomers of Proteins of the Invention

For the avoidance of doubt, in the context of the present disclosure, references to a "monomer" of a protein of the invention are intended to cover a molecule made up of two chimeric polypeptide chains associated with one another. Suitably, the two chimeric polypeptide chains may be linked by an inter-disulphide bond formed between residue Cys226 and Cys229 of SEQ ID NO: 1.

Thus it can be seen that, for present purposes, a "trimer" would be made up of three "monomers" as referred to above—a total of six chimeric polypeptide chains. A "hexamer" would consist of six monomers, and hence a total of twelve chimeric polypeptide chains.

Compositions and Pharmaceutical Compositions of the Invention

The second aspect of the invention provides a composition comprising a protein according to the first aspect of the invention. In such a composition, at least 95% of the protein of the first aspect of the invention incorporated in the composition is in monomeric form.

Suitably a composition of the second aspect of the invention may be a pharmaceutical composition, in which the protein is provided with a pharmaceutically acceptable carrier.

In a suitable embodiment of a composition of the invention, whether a pharmaceutical composition or otherwise, at least 96% or at least 97% of the protein of the first aspect of the invention incorporated in the composition is in monomeric form. Indeed in a suitable embodiment, at least 98% or at least 99% of the protein of the first aspect of the invention incorporated in the composition is in monomeric form. Suitably substantially all of the protein of the first aspect of the invention incorporated in such a composition may be in monomeric form.

Medical Uses of the Proteins of the Invention

The proteins of the invention, for example provided in a composition of the invention, may be used as a medicament.

Proteins of the invention may, for example, be used as medicaments in IVIG or SCIG. Such medical uses of the proteins and compositions are of particular utility in the prevention or treatment of autoimmune or inflammatory diseases. Medical use of the proteins of the invention in this manner may be effective, irrespective of whether or not they are conjugated to a therapeutic payload.

Proteins of the invention may be used as medicaments for the prevention or treatment of diseases mediated through binding of sialic acid-dependent receptors.

As mentioned elsewhere in this specification, proteins of the invention, in particular proteins comprising the artificial glycosylation site at residue 1 of SEQ ID NO:2 or SEQ ID NO:17, have the ability to bind sialic acid-dependent receptors, such as SIGLEC-1, and thereby prevent other molecules from binding to the receptor. The inventors believe that the ability of the proteins to bind SIGLEC-1 and other sialic acid-dependent receptors is a result of their greater sialylation.

Accordingly, the proteins of the invention may be used as medicaments in diseases in which preventing the binding of other molecules to sialic acid dependent receptors may have a therapeutic effect. Merely by way of example, preventing binding to SIGLEC-1 may have a therapeutic effect in retrovirus infections (such as HIV or T-cell leukaemia virus infections), or other conditions in which infectious agents bind via SIGLEC-1. Accordingly, proteins of the invention, and in particular proteins comprising artificial glycosylation site corresponding to that found at residue 1 of SEQ ID NO:2 or SEQ ID NO:17, may be used in the prevention or treatment of infections. Suitably proteins of the invention may be used in the prevention or treatment of retrovirus infections.

Proteins of the invention comprising or consisting of SEQ ID NO:17 are particularly suited for the medical uses described above.

Other suitable examples of such diseases, which may benefit from prevention or treatment through medical use of the proteins of the invention, are considered below.

As mentioned elsewhere in this specification, the protein of the invention may be conjugated to a therapeutic payload. The term "therapeutic payload" as used herein refers to a compound which itself has a therapeutic effect. The therapeutic effect of a therapeutic payload may be in addition to, or independent of, the therapeutic effect of the protein of the invention.

Further medical uses of the proteins of the invention may be selected with reference to a therapeutic payload conjugated to such proteins. A suitable therapeutic payload may be selected from the group consisting of an immune modulator, a drug, a protein, a carbohydrate, and a nucleic acid.

A suitable immune modulator may upregulate or downregulate components of the immune system.

A protein of the invention conjugated to an immune modulator which upregulates components of the immune system may be useful as a vaccine. By way of example an immune modulator which may be useful as a vaccine may be a pathogen-associated molecular pattern (PAMP) molecule or an antigen. Accordingly, the present invention provides the use of proteins of the invention as vaccines.

A protein of the invention conjugated to an immune modulator which down regulates the components of the immune system may be useful as a medicament for autoimmune diseases, for example rheumatoid arthritis.

An examples of such an immune modulator which down regulates the components of the immune system is erythropoietin. Accordingly, it will be appreciated that in a suitable embodiment erythropoietin may be conjugated to a protein of the invention. Such a conjugated protein may be used in the prevention or treatment of an autoimmune disease.

The term "drug" as used herein refers to a compound with therapeutic activity, for example a small molecule, which may be conjugated to a protein of the invention. Merely by way of example, a suitable drug therapeutic payload may be one, such as monomethyl auristatin E, which may be useful in the treatment of cancer. Suitably, the drug, such as monomethyl auristatin E, may be further conjugated to an antibody. Accordingly, a protein of the invention may be conjugated to an anti-cancer drug, such as monomethyl auristatin E. Such a conjugated protein may be used in the prevention or treatment of cancer.

Merely by way of example, a suitable protein therapeutic payload for conjugation to a protein of the invention may be a cytokine receptor. Cytokine receptors may be useful for inhibiting disease causing cytokines, by for example, binding such disease causing cytokines, and thereby preventing them from pathogenically binding to cells.

A suitable carbohydrate payload to be conjugated to a protein of the invention may be, for example, hyaluronic acid.

A suitable nucleic acid payload to be conjugated to a protein of the invention may be, for example, unmethylated CpG oligodeoxynucleotide. Proteins of the invention conjugated in this manner are suitable for medical use as immunostimulants.

Methods of Treatment Using the Proteins of the Invention

The proteins of the invention, for example provided in a composition of the invention, may be used as a medicament. The proteins may be conjugated to a therapeutic payload. Alternatively, they may be not conjugated to a therapeutic payload.

Such medical uses of the proteins and compositions thereof are of particular utility in the prevention or treatment of autoimmune or inflammatory diseases, whether or not the proteins are conjugated to a therapeutic payload.

Additionally, as already mentioned, the inventors have surprisingly found that the proteins of the invention, in particular proteins comprising the artificial glycosylation site at residue 1 of SEQ ID NO:2 (such as the protein of SEQ ID NO:17), have the ability to bind sialic acid dependent receptors, for example, SIGLEC-1 receptors. The proteins may thereby prevent other molecules from binding to the receptor, or may be used to trigger such receptors for therapeutic effect.

Therefore, proteins of the invention which are not conjugated to therapeutic payloads may be particularly useful in the prevention or treatment of diseases in which preventing the binding of other molecules to SIGLEC-1 may have a therapeutic effect. Merely by way of example, preventing binding to sialic acid-dependent receptors such as SIGLEC-1 may have a therapeutic effect in prevention or treatment of infections, such as retrovirus infections (such as Human Immunodeficiency Virus or T-cell Leukaemia Virus infections).

Other suitable examples of such diseases, which may benefit from prevention or treatment through medical use of the proteins of the invention, are considered below.

The subject may be provided with a protein of the invention by any technique through which the subject will ultimately receive a therapeutically effective amount of the protein of the invention.

Thus, in a suitable embodiment the subject may be provided directly with the protein of the invention. In such an embodiment the subject may, for example, be provided with a composition of the invention comprising the protein of the invention in monomeric form.

In another embodiment the subject may be provided indirectly with the monomeric protein. By way of example, in such an embodiment, a nucleic acid according to the sixth aspect of the invention (a nucleic acid encoding a protein of the invention) may be administered to the subject, and the therapeutically effective amount of the protein of the invention provided by expression of the nucleic acid to yield the protein. Accordingly, in a seventh aspect, the present invention provides a nucleic acid in accordance with the sixth aspect of the invention for use as a medicament. The medical use of nucleic acids of the invention in this manner may be of benefit in the applications described with reference to the medical uses of proteins of the invention Nucleic Acids of the Invention The sixth aspect of the invention provides nucleic acids that encode the proteins of the invention. In a suitable embodiment, the nucleic acids may encode a chimeric polypeptide, wherein the cysteine corresponding to that at position 575 of IgM (equivalent to C248 of SEQ ID NO:1) is lost. In such an embodiment the cysteine residue may be substituted by an alanine residue.

The nucleic acid of the invention may be a DNA molecule encoding a protein of the invention. Alternatively, the nucleic acid of the invention may be an RNA molecule, encoding a protein of the invention.

Suitably, a nucleic acid of the invention may comprise SEQ ID NO:3, which encodes a polypeptide of SEQ ID NO: 2.

In a suitable embodiment the nucleic acid of the invention may share at least 70% identity with SEQ ID NO: 3, at least 75% identity with SEQ ID NO: 3, at least 80% identity with SEQ ID NO: 3, at least 85% identity with SEQ ID NO: 3, at least 90% identity with SEQ ID NO: 3, at least at least 95% identity with SEQ ID NO: 3, at least 96% identity with SEQ ID NO: 3, at least 97% identity with SEQ ID NO: 3, at least 98% identity with SEQ ID NO: 3, or at least 99% identity with SEQ ID NO: 3.

It will be appreciated the nucleic acids of the invention may be incorporated in larger nucleic acid sequences, which will comprise regions that do not encode the monomeric proteins of the invention. Merely by way of example, a nucleic acid of the invention may be incorporated in an expression plasmid, such as pFUSE-hIgG1-Fc-TP-LH309/310CL or pFUSE-hIgG1-Fc-TP-L310H.

Production of Proteins of the Invention

The seventh aspect of the invention provides a method of producing a protein in accordance with the first aspect of the invention. These methods comprise expressing a nucleic acid in accordance with the sixth aspect of the invention in a host cell.

In a suitable embodiment, the host cell may be a eukaryotic host cell. In particular, a suitable eukaryotic expression host may be selected from the group consisting of yeasts (for example *Pichia pastoris* and *Saccharomyces cerevisiae*) and mammalian cell systems.

Suitable mammalian cell systems may be selected from the group consisting of: HEK-293 cells, CHO-K1 cells, mouse-derived NS0 cells and BHK cells. Other suitable mammalian cell systems will be known to the skilled person. It will be appreciated that suitable host cells will comprise a means for attaching glycans to the expressed proteins.

It will also be appreciated that the type of cells in which the proteins of the invention are expressed in may impact upon the type of linkages formed between the protein of the invention and a sialic acid. By way of example, proteins of the invention which are produced in CHO-K1 cells, may only form α2,3 linkages, and therefore may only bind SIGLEC-1 (as opposed to SIGLEC-2) receptors.

However, the expression of proteins of the invention in other types of cells, for example human cells (such as HeLa or HEK cells), may allow the formation of α2,3 linkages and α2,6 linkages. The presence of an α2,6 linkage may enable the proteins of the invention to bind SIGLEC-2 receptor (also known as CD22). The ability of the proteins of the invention to bind SIGLEC-2 receptor may be especially useful in the treatment of autoimmune diseases, for example by IVIG or SCIG treatment.

Accordingly, it will be recognised that the cells in which a protein of the invention are to be expressed may be selected with reference to desired glycosylation to be achieved, and the intended therapeutic use of the protein.

The inventors believe that the proteins of the invention are associated with various practical advantages. For example, they simplify the process of manufacturing, since the proteins of the invention are produced as uniform monomers. Thus the step of selecting proteins of only a particular size may be eliminated. The fact the proteins have the ability to not polymerise, may also extend the shelf-life of products comprising the proteins of the invention, without the concern that they will polymerise and lose their biological activities.

Diseases that May be Prevented or Treated

Suitable autoimmune or inflammatory diseases for prevention or treatment using the proteins of the invention include those that are treatable with IVIG. These may be diseases which are currently routinely treated with IVIG or in which IVIG has been found to be clinically useful, such as autoimmune cytopenias, Guillain-Barré syndrome, myasthenia gravis, anti-Factor VIII autoimmune disease, dermatomyositis, vasculitis, and uveitis. IVIG is typically used to treat idiopathic thrombocytopenic purpura (ITP), Kawasaki disease, Guillain-Barré syndrome and chronic inflammatory demyelinating polyneuropathy. IVIG may also be used to treat a diverse array of other autoimmune diseases which are non-responsive to mainstay therapies, including arthritis, diabetes, myositis, Crohn's colitis, and systemic lupus erythematosus.

Autoimmune or inflammatory diseases suitable for treatment include autoimmune cytopenia, idiopathic thrombocytopenic purpura, rheumatoid arthritis, systemic lupus erythematosus, asthma, Kawasaki disease, Guillain-Barré syndrome, Stevens-Johnson syndrome, Crohn's colitis, diabetes, chronic inflammatory demyelinating polyneuropathy myasthenia gravis, anti-Factor VIII autoimmune disease, dermatomyositis, vasculitis, uveitis, and Alzheimer's disease. It will be appreciated that autoimmune or inflammatory diseases such as those listed above may be treatable by a protein of the invention without a therapeutic payload. In such an embodiment treatment may be provided by IVIG or SCIG. Alternatively or additionally, the diseases may be treatable by a protein of the invention conjugated to a therapeutic payload. Such a therapeutic payload may be, for example, an immune modulator which down regulates the components of the immune system.

Conditions to be treated may include an inflammatory disease with an imbalance in cytokine networks, an autoimmune disorder mediated by pathogenic autoantibodies or autoaggressive T cells, or an acute or chronic phase of a chronic relapsing autoimmune, inflammatory, or infectious disease or process. In addition, other medical conditions having an inflammatory component are included, such as Amyotrophic Lateral Sclerosis, Huntington's Disease, Alzheimer's Disease, Parkinson's Disease, Myocardial Infarction, Stroke, Hepatitis B, Hepatitis C, Human Immunodeficiency Virus associated inflammation, T-cell leukaemia virus associated inflammation, adrenoleukodystrophy, and epileptic disorders especially those believed to be associated with postviral encephalitis including Rasmussen Syndrome, West Syndrome, and Lennox-Gastaut Syndrome.

Conditions to be treated may be hematoimmunological diseases, e.g., Idiopathic Thrombocytopenic Purpura, alloimmune/autoimmune thrombocytopenia, Acquired immune thrombocytopenia, Autoimmune neutropenia, Autoimmune hemolytic anemia, Parvovirus B19-associated red cell aplasia, Acquired antifactor VIII autoimmunity, acquired von Willebrand disease, Multiple Myeloma and Monoclonal Gammopathy of Unknown Significance, Aplastic anemia, pure red cell aplasia, Diamond-Blackfan anemia, hemolytic disease of the newborn, Immune-mediated neutropenia, refractoriness to platelet transfusion, neonatal post-transfusion purpura, hemolytic uremic syndrome, systemic Vasculitis, Thrombotic thrombocytopenic purpura, or Evan's syndrome.

Alternatively, a neuroimmunological disease may be treated, e.g., neuritis, Guillain-Barré syndrome, Chronic Inflammatory Demyelinating Polyradiculoneuropathy, Paraproteinemic IgM demyelinating Polyneuropathy, Lambert-Eaton myasthenic syndrome, Myasthenia gravis, Multifocal Motor Neuropathy, Lower Motor Neuron Syndrome associated with anti-GM1 antibodies, Demyelination, Multiple Sclerosis and optic neuritis, Stiff Man Syndrome, Paraneoplastic cerebellar degeneration with anti-Yo antibodies, paraneoplastic encephalomyelitis, sensory neuropathy with anti-Hu antibodies, epilepsy, Encephalitis, Myelitis, Myelopathy especially associated with Human T-cell lymphotrophic virus-1, Autoimmune Diabetic Neuropathy, or Acute Idiopathic Dysautonomic Neuropathy, and Alzheimer's disease.

A rheumatic disease may be treated, e.g., Kawasaki's disease, Rheumatoid arthritis, Felty's syndrome, ANCA-positive Vasculitis, Spontaneous Polymyositis, Dermatomyositis, Antiphospholipid syndromes, Recurrent spontaneous abortions, Systemic Lupus Erythematosus, Juvenile idiopathic arthritis, Raynaud's, CREST syndrome or Uveitis.

A dermatoimmunological disease may be treated, e.g., Epidermal Necrolysis, Gangrene, Granuloma, Autoimmune skin blistering diseases including Pemphigus vulgaris, Bullous Pemphigoid, and Pemphigus foliaceus, Vitiligo, Streptococcal toxic shock syndrome, Scleroderma, systemic sclerosis including diffuse and limited cutaneous systemic sclerosis, Atopic dermatitis or steroid dependent Atopic dermatitis.

A musculoskeletal immunological disease may be treated, e.g., Inclusion Body Myositis, Necrotizing fasciitis, Inflammatory Myopathies, Myositis, Anti-Decorin (BJ antigen) Myopathy, Paraneoplastic Necrotic Myopathy, X-linked Vacuolated Myopathy, Penacillamine-induced Polymyositis, Atherosclerosis, Coronary Artery Disease, or Cardiomyopathy.

A gastrointestinal immunological disease may be treated, e.g., pernicious anemia, autoimmune chronic active hepatitis, primary biliary cirrhosis, Celiac disease, dermatitis herpetiformis, cryptogenic cirrhosis, Reactive arthritis, Crohn's disease, Whipple's disease, ulcerative colitis, or sclerosing cholangitis.

The disease may be, for example, post-infectious disease inflammation, Asthma, Type 1 Diabetes mellitus with anti-beta cell antibodies, Sjogren's syndrome, Mixed Connective Tissue Disease, Addison's disease, Vogt-Koyanagi-Harada Syndrome, Membranoproliferative glomerulonephritis, Goodpasture's syndrome, Graves' disease, Hashimoto's thyroiditis, Wegener's granulomatosis, micropolyarterits, Churg-Strauss syndrome, Polyarteritis nodosa, or Multisystem organ failure.

An exemplary disease for treatment is idiopathic thrombocytopenic purpura (ITP).

It will be appreciated that conditions, such as those listed above, that are capable of treatment by IVIG may also be treated by SCIG. Accordingly, the use of the proteins or compositions of the invention in SCIG treatment of these conditions is also provided by the present invention.

The inventors believe that the proteins of the invention may lend themselves to use in improved activating and/or tolerogenic vaccines. Such vaccines may be suitable for use in individuals where activation of complement activation may not be desirable.

The proteins of the invention may be useful in the prevention or treatment of diseases which are mediated by the SIGLEC-1 receptor. Such diseases include those, such as viral infections, in which an infectious agent binds via SIGLEC-1. Suitable viral infections include retrovirus infections caused by, for example, Human Immunodeficiency Virus, T-cell Leukaemia Virus.

Diseases mediated by the SIGLEC-1 receptor may be prevented or treated by the proteins of the invention regardless of whether they are conjugated to a therapeutic payload or not. Proteins of the invention which are not conjugated to a therapeutic payload may prevent or treat the disease by blocking SIGLEC-1 receptors through competitive binding. Alternatively proteins of the invention, whether conjugated to a therapeutic payload or not, may achieve therapeutic activity by triggering effector functions from such receptors. Proteins of the invention which are conjugated to a therapeutic payload, may prevent or treat the disease through the therapeutic effect of the therapeutic payload, or through a combination of the therapeutic effect of the therapeutic payload and blocking of SIGLEC-1 receptors through competitive binding.

As mentioned elsewhere in the specification, those proteins of the invention to which an additional glycosylation site has been introduced (for example at residue 1 of SEQ ID NO:1 or SEQ ID NO:2, as found in SEQ ID NO:17) represent particularly suitable embodiments for use in the prevention or treatment of diseases modulated by SIGLEC-1.

The invention will now be further described with reference to the following Examples and accompanying figures, in which:

FIG. 1. Schematic showing the glycan and cysteine mutants generated on the hexameric Fc template plasmid hIgG1-Fc-CL309/310CH-TP. Stars indicate the IgG heavy chain constant region (such as Cγ2) N297 and tailpiece N563 glycan sites respectively. C=A indicates mutation of cysteine 575 for alanine in the tailpiece.

Figure 2:
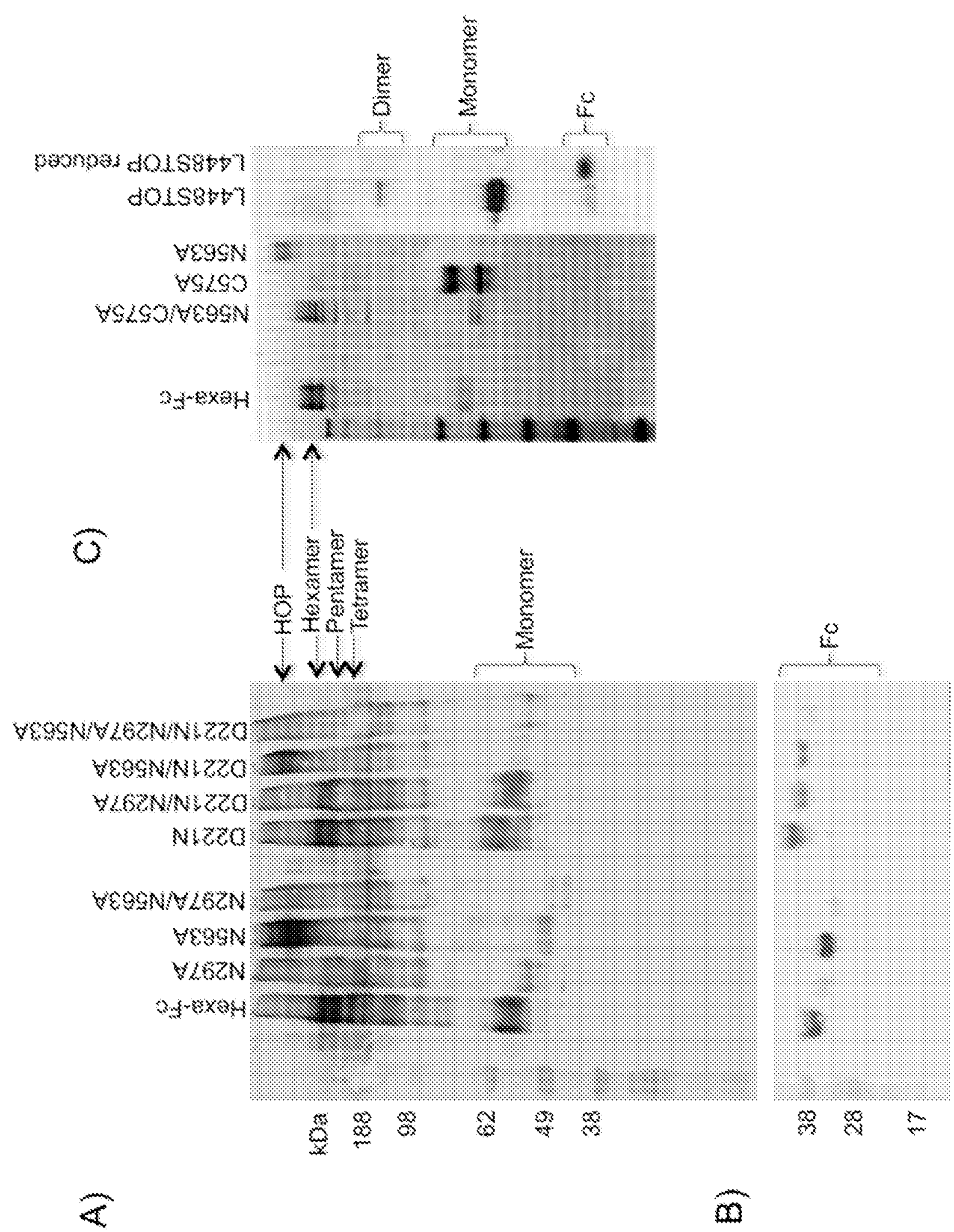

FIG. 2. Characterization of mutant Fc-proteins by SDS-PAGE. (A) Wildtype hexa-Fc and the N297A, D221N/N297A mutants run as high molecular weight pentamers and hexamers. The loss of the N297A glycan does not inhibit oligomerization but results in oligomers that are commensurately smaller than fully glycosylated wildtype hexa-Fc (arrowed). The N563A mutant runs at a molecular weight that approximates dodecamers (also FIG. 7). (C) N563A/C575A mutant results in proteins that run as laddered oligomers, while C575A and L448STOP mutants run as monomers. Removal of C575A may result in more complex glycans being attached to the N563A sequon as a monomer than are possible in an oligomer, and therefore the two monomeric species seen for this mutant most likely represent differentially glycosylated monomers. (B) Proteins from (A) run under reducing conditions. The decreasing molecular weights seen in the Fc represent sequential loss of N-linked glycans. Thus N297A/N563A mutant has the smallest molecular weight as it has no glycans attached to the Fc. This panel also shows the comparative sizes of the glycans attached, the N221 glycan being larger than N563, which in turn is larger than N297.

FIG. 3. Binding of mutants to DC-SIGN. Mutants lacking the N297 glycan are severely restricted in their capacity to bind DC-SIGN by ELISA. The monomeric C575A mutant binds DC-SIGN better than wildtype IgG-Fc (lacking the tailpiece, and as in IVIG preparations) showing that the N563 glycan can contribute to DC-SIGN but only when presented as a monomer through removal of Cys575 (also FIG. 6). The addition of an N-linked sugar at position 221 as with the D221N mutants results in proteins with a reduced capacity to bind DC-SIGN.

Figure 4:
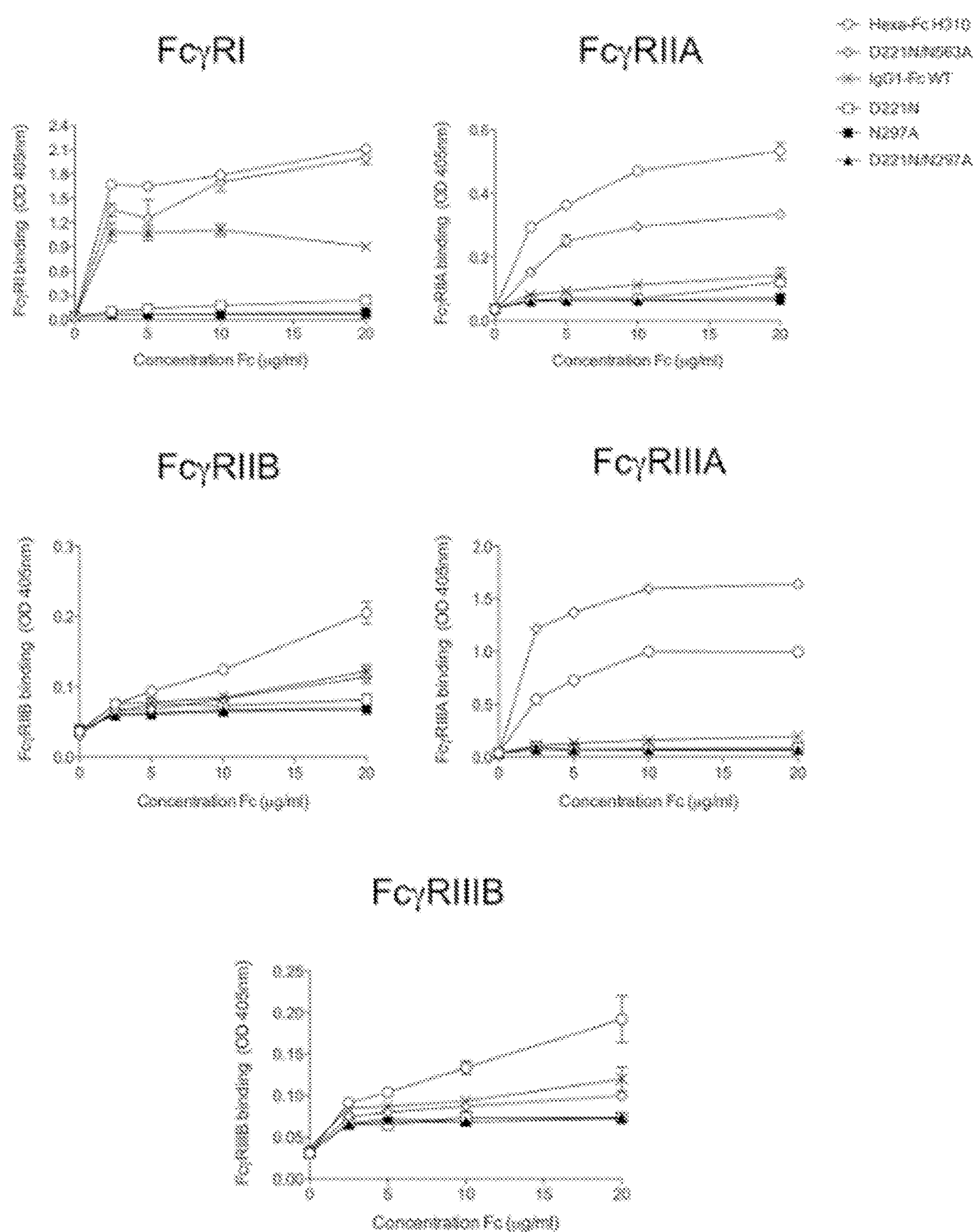
Figure 4:
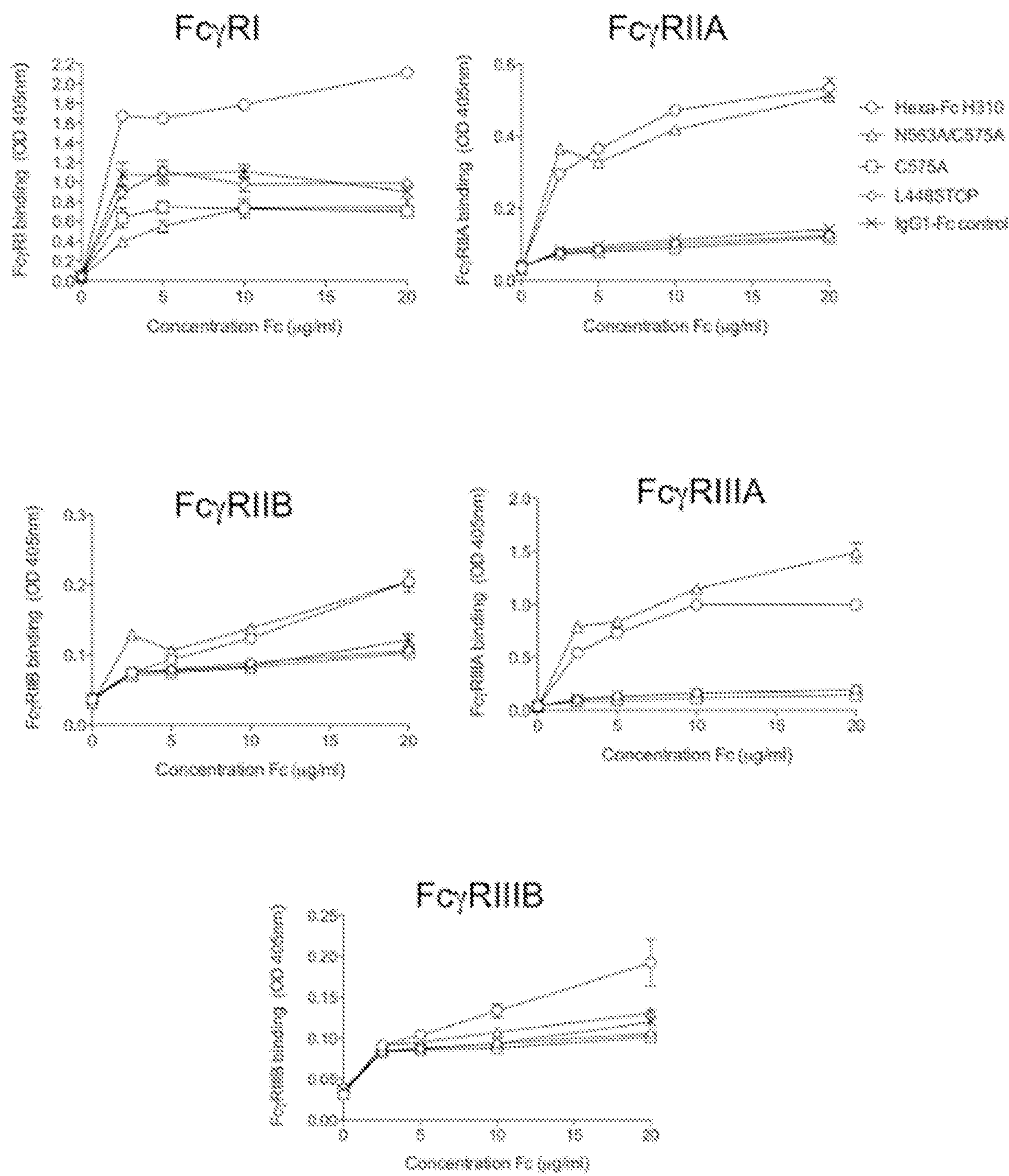

FIG. 4. Binding of mutants to classical FcγRs assessed by ELISA. Removal of the N297 glycan as in the N297A and D221N/N297A mutants (FIG. 4 A) results in a dramatic loss of binding to all FcγRs studied. The N563A/C575A mutant (FIG. 4 B) that gives rise to laddered oligomers binds equally well to low-affinity FcγRIIA, FcγRIIB, FcγRIIIA, FcγRIIIB as either wildtype-hexameric-Fc or the D221N/N563A dodecamer, but binds the high-affinity FcγRI poorly compared to either hexameric-Fc or D221/N563A. The C575A monomer (FIG. 4 B) has an FcγR binding profile that mimics the monomeric IgG1-Fc control.

FIG. 5. Binding of mutants to complement component C1q and subsequent activation of the complement cascade as measured by C5b-9 (membrane attack complex) deposition assessed by ELISA. Removal of the Asn297 glycan as in the N297A, N297A/N563A, D221N/N297A, or D221N/N297A/N563A mutants resulted in dramatic loss of binding to both C1q and subsequent C5b-9 deposition. The N563A and D221N/N563A mutants were as good as wild-type hexa-Fc at activating complement. Although unable to bind FcγRs, the D221N mutant was clearly capable of binding C1q, leading to C5b-9 deposition although not as efficiently as either hexa-Fc or N563A. (n=2 independent experiments)

Figure 6:
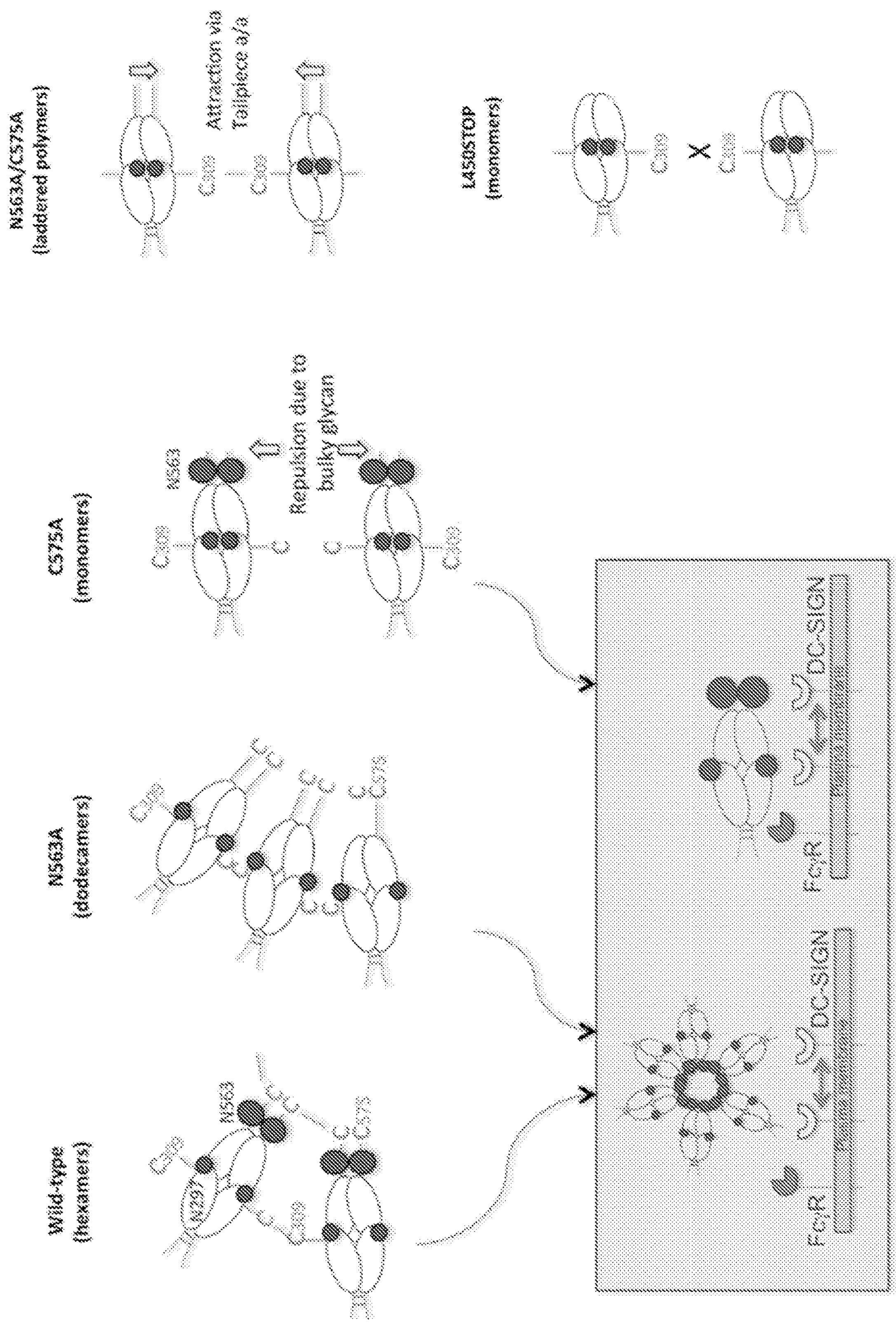

FIG. 6. Model showing the contribution of Asn563, Cys309 and Cys575 to different Fc stoichiometries. The presence of Cys575 allows optimal disulphide bonding between Cys575 in the tailpieces of monomeric-Fcs. The tailpiece glycan Asn563 thereby controls the number of monomeric tails that fit into the central corona (five to six in the case of hexa-Fc), whilst still allowing Cys309 inter-disulfide bridge formation. Cys575 allows disulphide bonding between tailpieces of different monomers, but the absence of the Asn563 glycan now allows many more tailpieces (up to twelve in the case of dodecamers) to fit into the central corona whilst still allowing disulphide bond formation through Cys309. The absence of Cys575 prevents disulphide bonding between tailpieces thereby generating monomers with two occupied N-glycosylation sites (Asn297 and Asn563). The additional tailpiece glycan in these monomers now allowing for greater avidity interactions with DC-SIGN, and as seen with hexamers through the Asn297 glycan (see inset). The bulkier Asn563 glycan with its predicted overall negative charge now causing repulsion between two monomers and preventing disulphide bond formation between two adjacent Cys309 residues in each monomeric Fc. The loss of both Asn563 and Cys575 means that higher order polymers can only arise through disulphide bonding mediated through Cys309 in the IgG heavy chain constant region (such as Cγ2 domain). The presence of dimers, trimers, tetramers, pentamers and hexamers in this N563A/C575A mutant (FIG. 2) implies that these structures arise through a different mechanism, most likely through the sequential addition of monomeric Fc units. The lack of these ladders with the L448STOP mutant (SEQ ID NO: 6 and 7) implies that other amino acids in the tailpiece are involved in bringing about monomer interactions that facilitate disulphide bonding through Cys309.

Figure 7:
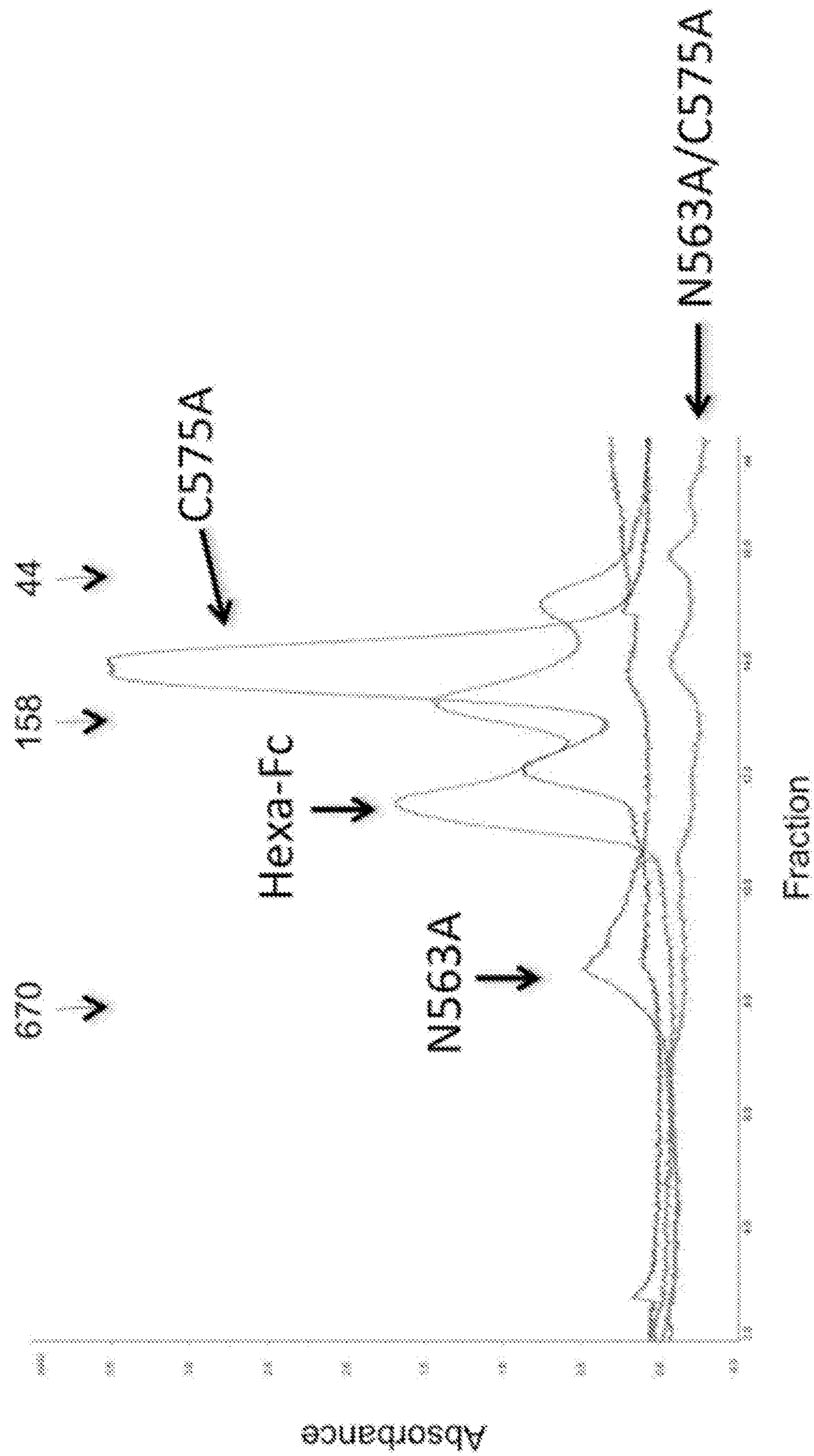

FIG. 7. Size-exclusion chromatography (SEC) analysis on Superdex-200 10/300GL column for hexa-Fc wildtype, and N563A, C575A, N563A/C575A mutants. Elution profiles of molecular weight standards are omitted for clarity but indicated with arrows for bovine thyroglobulin (670 kDa), bovine γ-globulin (158 kDa) and chicken ovalbumin (44 kDa).

Figure 8:
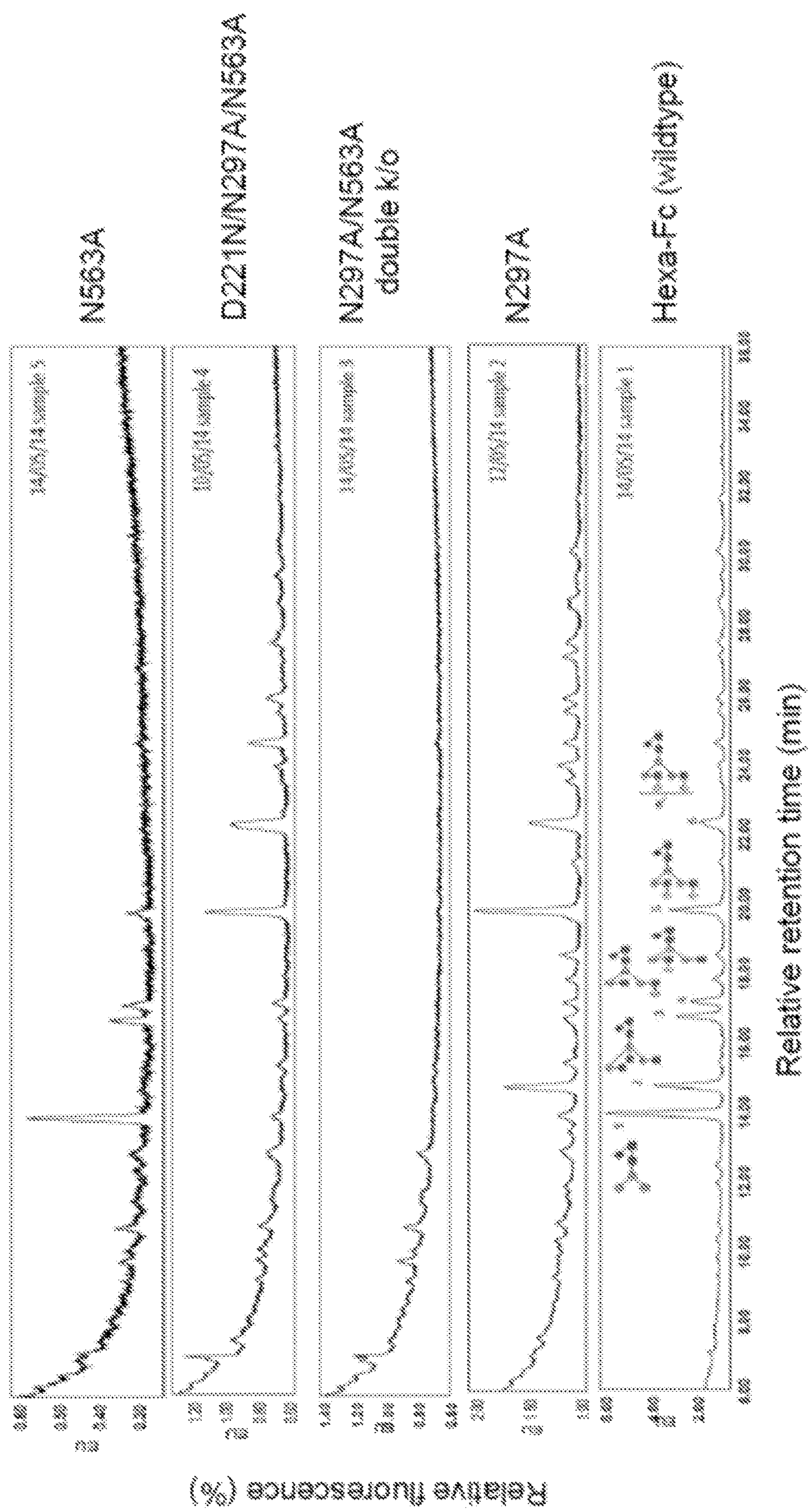

FIG. 8. Generation of differentially glycosylated hexa-Fc mutants. Normal-phase high-performance liquid chromatography analysis of N-linked glycans labelled with 2-aminobenzoic acid, released from target oligomeric recombinant Fc glycoformans by in-gel protein N-glycanase F digestion.

HPLC analysis of N-linked glycans was as previously described[1] (star) 5-N-acetylneuroaminic acid; (white rhombus) Gal; (square) GlcNAc; (circle) Man; (black rhombus) Fuc. The linkage position is shown by the angle of the lines linking the sugar residues (vertical line, 2-link; forward slash, 3-link; horizontal line, 4-link; black slash, 6-link). Anomericity is indicated by continuous lines for β-bonds and broken lines for α-bonds.

FIG. 9. A schematic showing the glycan and cysteine mutants generated on the hexa-Fc template plasmid hIgG1-Fc-CL309/310CH-TP. Stars indicate the hinge N221, the Cγ2 N297, and the tailpiece N563 glycan sites. C=A indicates mutation of cysteine 575 to alanine in the tailpiece. Abbreviations used include: M (monomer), D (dimer), O (oligomer), HOM (high order multimer) as determined by size-exclusion analysis and SDS-PAGE, n.d., not determined.

Figure 10:
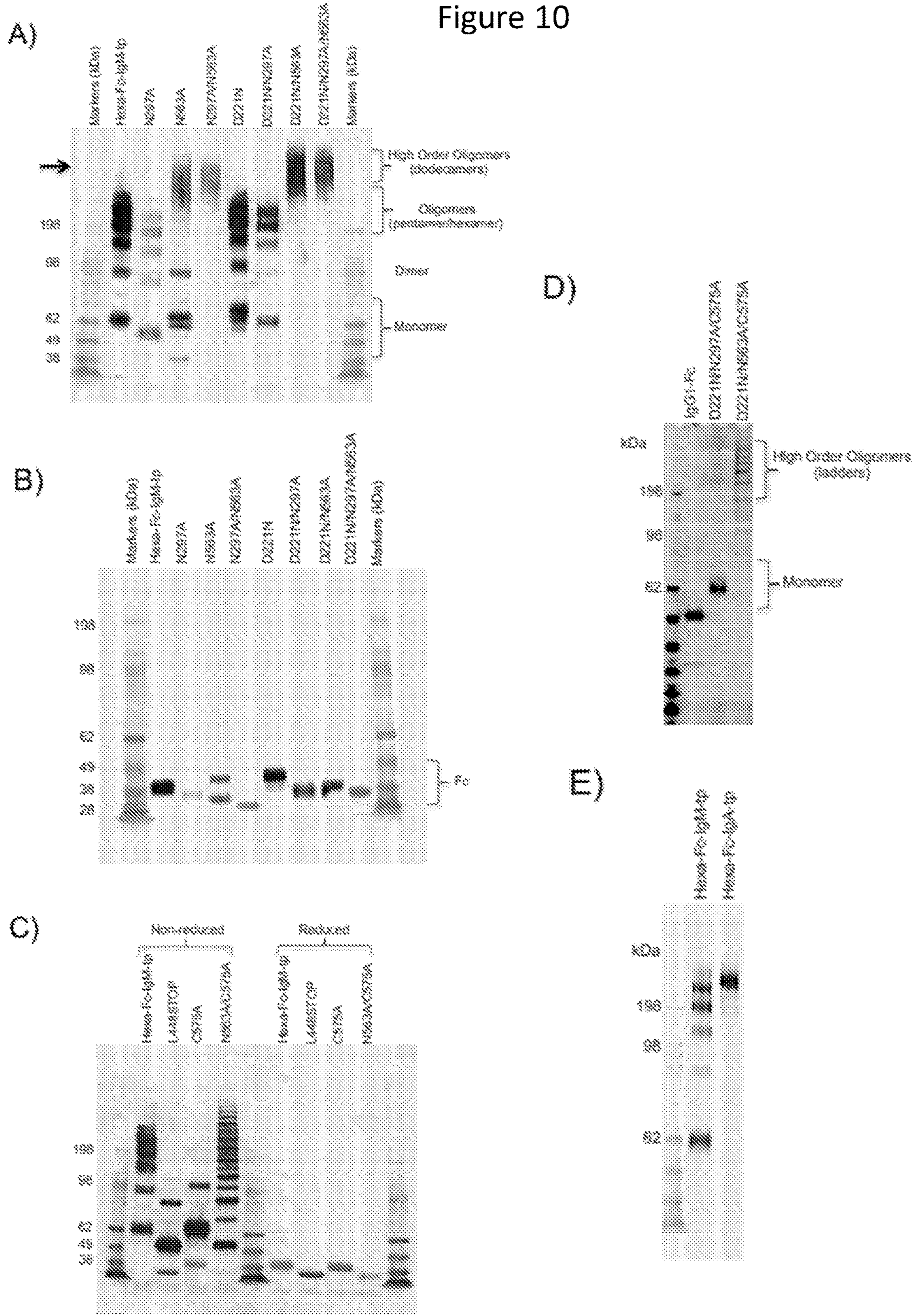

FIG. 10. Shows the characterisation of mutant Fc-proteins by SDS-PAGE. FIG. 10 A shows Hexa-Fc, N297A, N563A and N297A/N563A mutants run as high molecular weight multimers of varying valence under non-reducing conditions. The loss of the N297A glycan does not prevent multimerisation but results in lower molecular weight multimers commensurate with the loss of glycans from Asn297 as seen previously[3]. The N563A and N297A/N563A mutants run at molecular weights that approximate to dodecamers (also FIG. 17). The addition of a N-X-T/S glycan sequon to these mutants to generate N-terminally glycosylated hinges (the D221N series of mutants) did not affect multimerisation but increased the molecular weight of all mutants, and clearly shows that additional sugars may be attached to the N-terminus of the IgG1 hinge. FIG. 10 B shows the same mutants as in panel A but run under reducing conditions. The decreasing molecular weights seen in the Fc represent sequential loss of N-linked glycans. Thus the N297A/N563A mutant has the smallest molecular weight as it has no glycans attached to the Fc, and D221N has the largest molecular weight as it has three glycans attached. This panel also shows the comparative sizes of the glycans, the Asn221 and Asn563 glycans being larger than those attached to Asn297 (see also mass spectrometry data in FIG. 11 and FIG. 17). Loss of the N563A carbohydrate resulted in two observable Fc fragments that may represent differential glycosylation of Asn297. FIG. 10 C shows the N563A/C575A mutant results in proteins that run as laddered multimers under non-reducing conditions, while C575A and the L448STOP mutants run principally as monomers with a small proportion of dimer species observed. FIG. 10 D shows the D221N/N297A/C575A variant runs as a monomer whereas the D221N/N563A/C575A mutant runs as a ladder of varying molecular weights as seen with the N563A/C575A variant in panel C. FIG. 10 E shows the effects of replacing the eighteen amino-acid tailpiece from IgM with that from IgA resulted in a homogeneous preparation of multimers composed almost entirely of hexamers. All proteins were run under either non-reducing or reducing conditions at 1 μg protein per lane of a 4-8% acrylamide gradient gel, transferred to nitrocellulose, and blotted with anti-human IgG-Fc (Sigma).

FIG. 11. Shows results from HILIC-UPLC analysis of 2AA-labelled N-linked glycans from IgG1-Fc mutants expressed by CHO-K1 cells (see FIG. 9). Normal phase HILIC-UPLC analysis of 2AA-labelled N-linked glycans released from target antibody glycoforms by in-gel protein PNGase F digestion. Glycan profiles for the following variants: (A) hexa-Fc, IgG1-Fc, N563A (upper gel band), N563A (lower gel band); (B) D221N, D221N/N297A, D221N/N563A, D221N/N297A/N563A; (C) C575A, N563A/C575A, L448STOP. The y-axis displays relative fluorescence and the x-axis the relative elution time. Inserted Pie charts represent the means of two analytical replicates; the pie charts summarize the quantification of oligomannose-type (dark grey), galactosylated (light grey) and sialylated glycans (grey) on individual sites. Quantifications are based on the peak lists in FIG. 17 and FIG. 20. Percentages corresponding to this figure can be found in Table 3.

FIG. 12. A graph showing binding of IgG1-Fc variants to glycan receptors. FIG. 12 A shows binding of mutants lacking the N297 glycan are severely restricted in their capacity to bind DC-SIGN by ELISA. The addition of an N-linked sugar at position 221 results in proteins with a reduced capacity to bind DC-SIGN compared to their equivalent variants in which Asn221 is absent. FIG. 12 B shows binding of the hyper-sialylated D221N mutants bind Siglec-1. No binding was observed with the N297A/N563A glycan deficient mutant (n=2 independent experiments).

Figure 13:
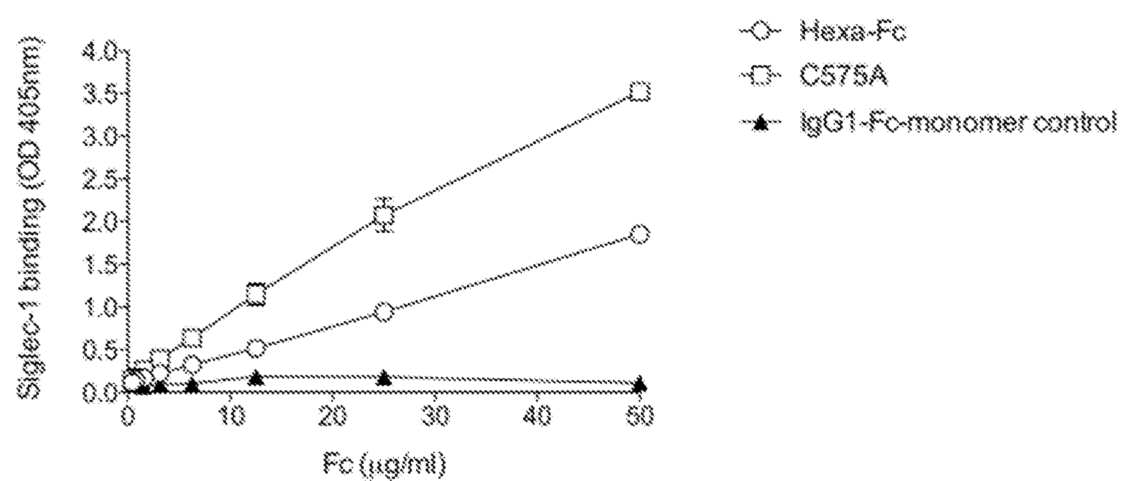

FIG. 13. A graph showing the binding of the monomeric IgG1-Fc C575A glycan variant to Siglec-1. The C575A monomer binds Siglec-1 better than hexa-Fc multimers. (n=2 independent experiments).

Figure 14:
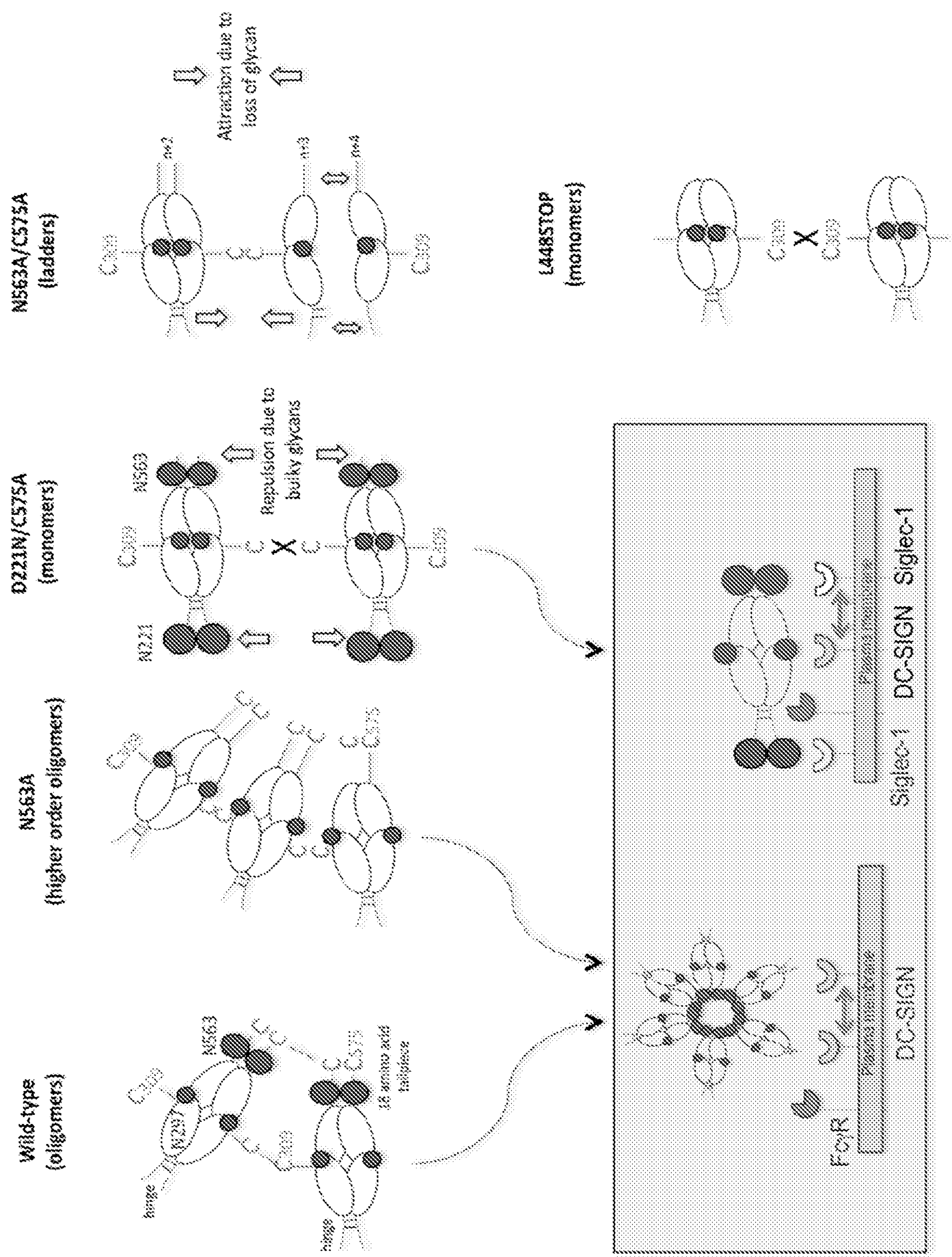

FIG. 14. A model showing the contribution of different N-linked glycan and cysteine residues on Fc stoichiometry. The presence of Cys575 allows optimal disulphide bonding between tailpieces of monomeric-Fcs. The tailpiece glycan Asn563 controls the number of monomeric tails that fit into the central corona (five to six in the case of hexa-Fc), whilst still allowing Cys309 inter-disulphide bridge formation. Cys575 allows disulphide bonding between tailpieces of different monomers, but the absence of the Asn563 glycan (the N563A mutant) allows many more tailpieces (up to twelve in the case of dodecamers) to fit into the central corona whilst still allowing disulphide bond formation through Cys309 and/or Cys575. The absence of Cys575 prevents disulphide bonding between tailpieces, thereby generating sialylated monomers at Asn563. The additional Asn563 tailpiece glycan in these monomers must explain the increased binding seen to Siglec-1. The bulkier Asn563 glycan with its predicted overall negative charge may lead to repulsion between two monomers, thus preventing disulphide bond formation between two Cys309 residues in each monomeric Fc. The loss of both Asn563 and Cys575 (the N563A/C575A mutant) means that the observed laddered multimers must arise through Cys309 mediated disulphide bonding in the Cγ2 domain. The presence of monomers, dimers, trimers, tetramers, pentamers, hexamers and other intermediates in this mutant (FIG. 100), suggests that these structures arise through a different mechanism, most likely via the sequential addition of 25 kDa halfmer Fc units at Cys309. The lack of observable ladders with the L448STOP mutant implies that other amino acids in the tailpiece are involved in bringing about monomer interactions that then facilitate disulphide bonding through either Cys309 and/or Cys575. Monomers with glycans located at both the N- and C-terminal ends of the Fc (Asn221 and Asn563) may allow for binding to receptors in cis.

Figure 15:
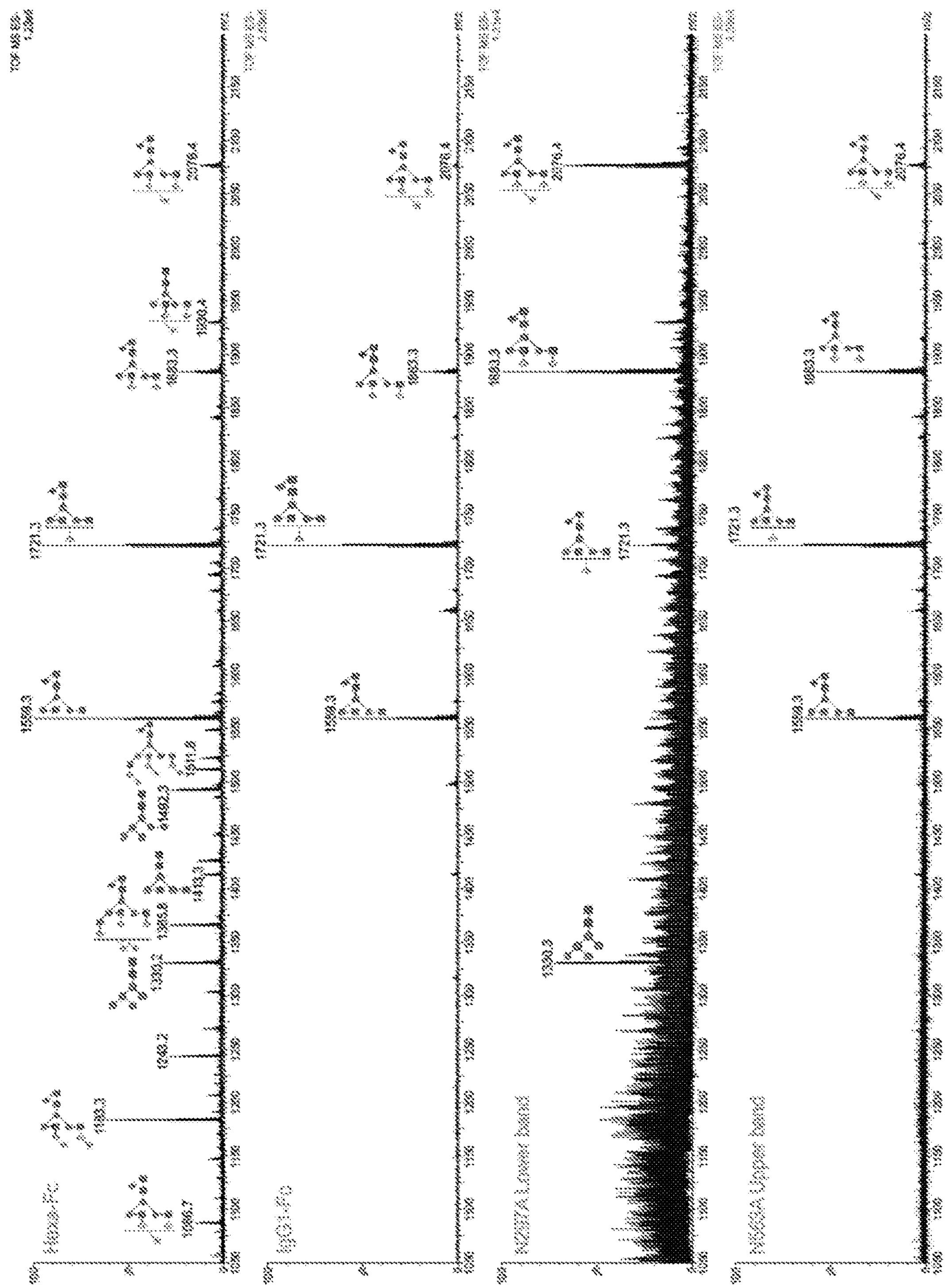
Figure 15:
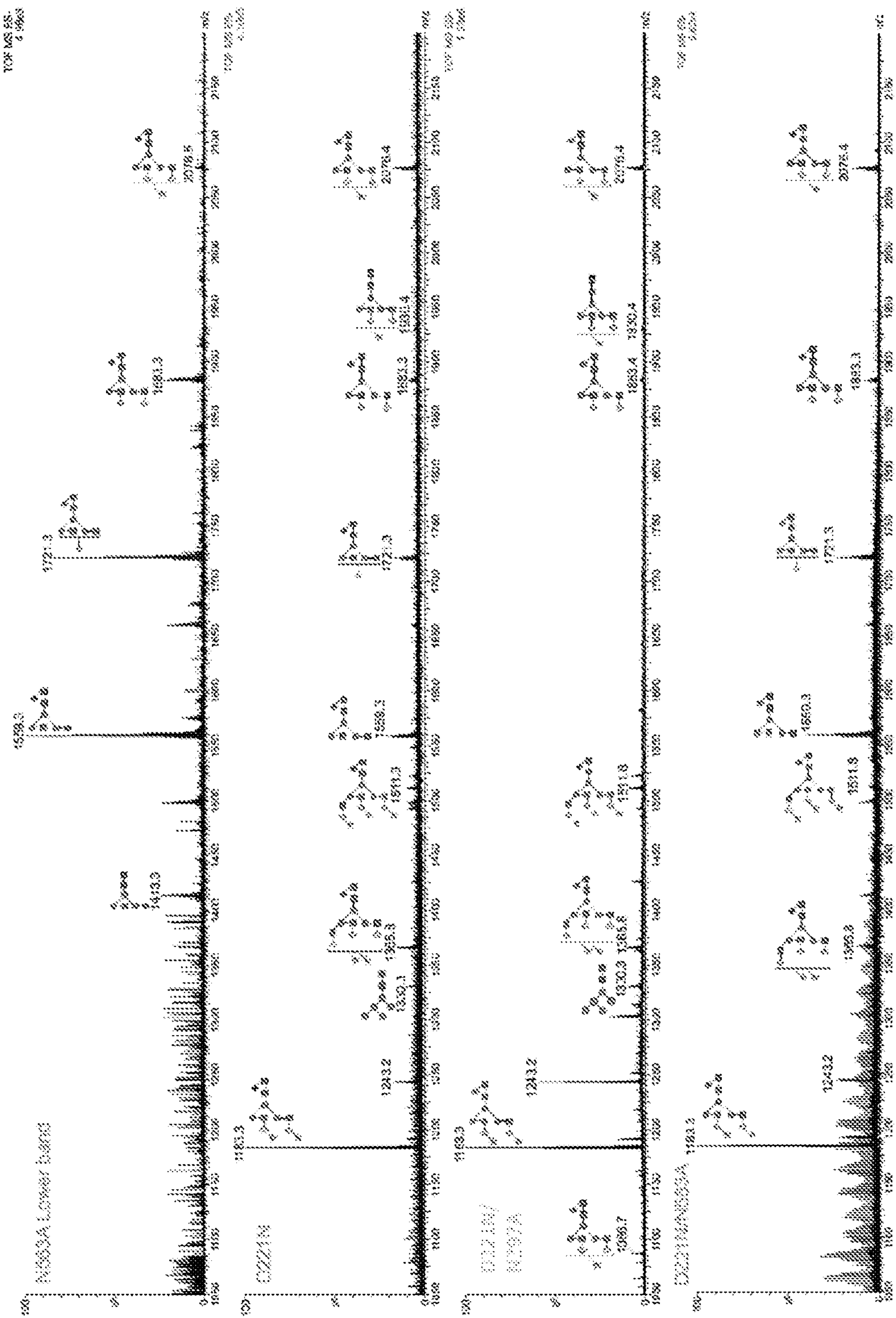
Figure 15:
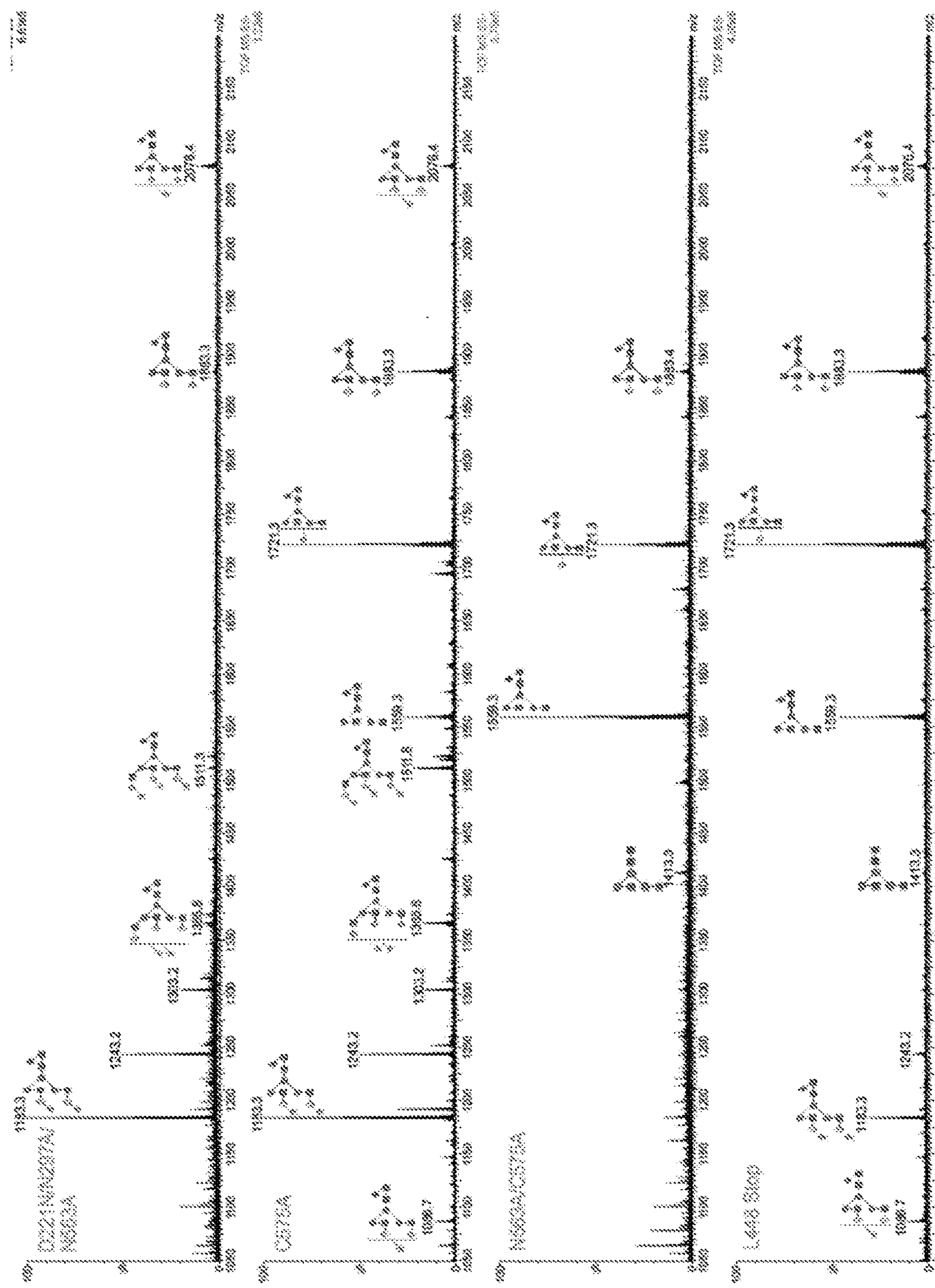
Figure 15:
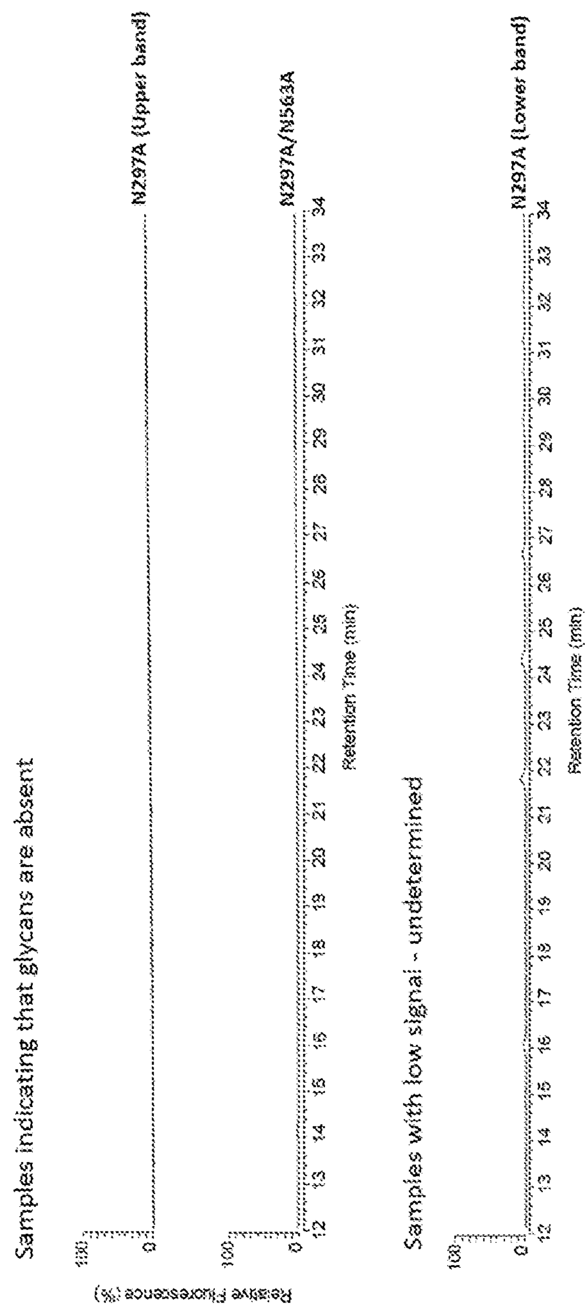

FIG. 15. Shows MALDI-TOF mass spectrometric analysis of N-linked glycans released from hexa-Fc variants. Above for hexa-Fc, IgG1-Fc, N297A (lower band), N563A (upper band); N563A (lower band), D221N, D221N/N297A, and D221N/N563A; D221N/N297A/N563A, C575A, N563A/C575A and L448STOP; N297A and N297A/N563A. N-linked glycans were released from IgG-Fc by PNGase F digestion. The symbolic representation of glycans follows that of Harvey et al [refs 1,4] with residues in both the schematic diagrams and molecular graphics following the Consortium for Functional Glycomics.

FIG. 16. Shows a list of masses, compositions and structures of the N-glycans derived from electrospray mass spectrometry and then converted into singly and doubly charged ions using ion mobility extraction.

EXAMPLES

Abstract

The human IgG1-Fc can be engineered into multimeric structures (hexa-Fcs) that bind to classical and non-classical Fc-receptors, including FcγRI, FcγRIIA, FcγRIIB, FcγRIIIA, FcRL5 and DC-SIGN with high avidity. Thus they may be attractive alternatives to antibodies and monomeric Fc proteins in applications where cross-linking of low-affinity receptors is mandatory for enhanced function and clinical utility. The critical influence of the unique N-linked glycan attached at Asn297 on the structure and function of the IgG1-Fc is well documented; however, whether this still applies to multimeric Fcs that bind with increased avidity is unknown. Hexa-Fc contains two N-linked sites, at Asn77 (equivalent to Asn297 in the Fc of IgG1) and Asn236 (equivalent to Asn563 in the tailpiece of IgM). We show that glycosylation at Asn297 is critical for functional interactions with Fc-receptors and complement, and that glycosylation at Asn563 is essential for controlling multimerisation. When an additional fully occupied N-linked glycosylation site is introduced at the N-terminus of the hinge at position 1 (equivalent to Asp221 in the Fc of IgG1), we show that the overall sialic acid content of Fc multimers is dramatically enhanced. Furthermore, replacement of Cys575 in the IgM tailpiece of such multimers results in monomers that have enhanced sialic acid content and show differential receptor binding profiles. Thus, the insertion of additional N-linked glycans into either the hinge and/or the IgM tailpiece of either monomers or multimers leads to molecules with enhanced sialylation that may be suitable for the treatment of inflammation or as blockers of pathogen invasion.

INTRODUCTION

Multimerised Fc and Fc-fusion proteins are increasingly being explored for novel drug and vaccine approaches. One potentially fertile area is their development as biomimetic replacements for intravenous immunoglobulin (IVIG) therapy. IVIG is a hugely successful biological with FDA approval for treating idiopathic thrombocytopenic purpura (ITP), Kawasaki disease, Guillain-Barré syndrome, Graves ophthalmopathy and numerous polyneuropathies. IVIG is increasingly viewed by clinicians as a last resort cure-all for a plethora of other diseases including: anemias, arthritides, lupus, transplant rejection, abortion, and chronic pain; especially when these are non-responsive to conventional therapies.

The global shortage and demand for IVIG is compounded by a number of other inadequacies with the current drug, the most significant being its dependency on human donors for its production, raising safety issues and greatly adding to cost. To add insult to injury <5% of the injected product (correctly glycosylated and/or oligomeric-Fc) is therapeutically active leading to a requirement for high dosages (2 g/kg). Consequently, IVIG is expensive and adverse events due to excessive IVIG loading not uncommon. There is therefore an urgent clinical need to develop synthetic replacements for IVIG for use in the clinic.

The mechanism of action of IVIG is incompletely understood. Although both Fab'$_2$ and Fc-mediated mechanisms may be involved, in humans the infusion of Fc fragments is sufficient to ameliorate ITP. IVIG suppresses harmful inflammation by engaging low-affinity inhibitory receptors and/or by forming complexes in vivo that allow IVIG to interact with these receptors with greater avidity, thus mediating more potent anti-inflammatory effects. The exact receptors or combinations of receptors involved are not definitively known, although both classical (type 1, e.g. FcγRIIB, FcγRIIIA) and non-classical (type 2, e.g FcγRs such as DC-SIGN, CD22, FcRL5) have been implicated in its therapeutic efficacy.

Based on the finding that Fc complexes can induce tolerance, a number of different approaches to Fc multimerization are being actively investigated. One approach utilizing the hinge region of human IgG2 generates laddered sequential multimers of diverse molecular weights when introduced into mouse IgG2a-Fc. The higher-order multimers, termed 'Stradomers™' bound strongly to low-affinity FcγRs and SIGN-R1, and were shown to protect animals from collagen-induced arthritis, ITP, inflammatory neuropathy, and autoimmune myasthenia gravis.

We took an alternative approach to multimerization by fusing the 18 amino-acid tailpiece from oligomeric IgM, together with a Leu to Cys substitution at position 309, into the IgG1-Fc. These molecules formed defined pentameric and hexameric structures whose binding to receptors was shown to be critically dependent on N-linked glycosylation. Glycosylation is important in increasing the solubility and in influencing interactions with both glycan- and Fc-receptors. Hexa-Fc contains two N-linked glycosylation sites at positions Asn297 in the Cγ2 domain and Asn563 in the eighteen amino acid IgM tailpiece of hexa-Fc. The hexameric Fc also binds the human neonatal receptor (FcRn), an interaction that is known to be critical to the maintenance of a long in vivo half-life and to enhanced immunogenicity. The efficacy of similar molecules in a mouse model of ITP has been reported in two patent applications (WO2015132364 and WO2015132365).

Glycosylation is important for correct protein folding in the endoplasmic reticulum and for exporting correctly folded proteins to the Golgi for post-translational modifications. Attached glycans also increase the solubility of proteins and have been shown to influence significantly the interactions of IgG with both glycan- and Fc-receptors. Glycosylation of the only available carbohydrate attachment site (Asn297) in the Fc is essential for interactions with both type 1 and 2 receptors. The Fc glycans at Asn297 are typically biantennary complex types, exhibiting high levels of fucosylation of the core GlcNAc residue, partial galactosylation, and bisecting GlcNac. Of these structures, less than 20% are sialylated. The reason for the low levels of branching and terminal structures, such as sialic acid, are believed to result from constraints on Asn297 glycan processing imposed by the Fc protein backbone.

The anti-inflammatory properties of the Fc are lost after deglycosylation of IVIG, and a population of IgG-bearing α2,6-sialylated Fcs has been identified as making a significant contribution to the control of inflammation. Higher levels of sialylation also lead to longer serum retention times. Indeed, the efficacy of sialylated Fc has generated an incentive to modify the existing glycans on Asn297, either by chemical means or through mutagenesis programs in the Fc protein backbone that disrupt the protein-Asn297 carbohydrate interface.

Here we have focused our studies on understanding the contribution of these two N-linked glycans, in combination with cysteine residues found in the tailpiece, to the structure and function of hexa-Fc. We show that the N-glycan at Asn297, whose sugars are enriched for high mannose and galactose when compared with IVIG, is essential for receptor binding by hexa-Fc. However, the glycans attached to the tailpiece Asn563 were found to be larger and more complex than those attached at Asn297 and were not critical to receptor binding as oligomers, but were essential in determining the type of oligomer formed. Removal of both Asn297 and Asn563 led to a significant drop in protein expression, inability to oligomerise, and a complete loss of receptor binding. These findings show the importance of N-linked glycosylation and the tailpiece in maintaining the structure and function of hexa-Fc, and as such, the translational potential of these molecules for either drug or vaccine applications.

Additionally, we have taken an unexplored approach to modifying glycosylation by introducing, in various combinations, up to three additional N-linked glycosylation sites into exposed areas of the IgG1-Fc (FIGS. 1 and 9). Hexa-Fc typically contains two N-linked glycosylation sites at positions Asn297 in the Cγ2 domain and at Asn563 in the eighteen amino acid IgM tailpiece of hexa-Fc.

We show, for the first time, that it is possible to add a further N-linked glycan onto the N-terminus of the IgG1-Fc hinge to generate a panel of hyper-sialylated molecules (the D221N series of mutants) that are still capable of forming multimers that then bind to the prototypic sialic acid dependent receptor, Siglec-1. By further mutagenesis of the tailpiece Cys575 to alanine, sialylated multimers can be converted into sialylated monomers that bind strongly to Siglec-1. This study clarifies the role of multiple N-linked glycans in maintaining a functional Fc structure, and provides routes to the development of antibody therapeutics with bespoke effector functions.

Materials and Methods

Production of Glycosylation Mutants.

The generation of hexa-Fc has been previously described[2,3]. The following mutants were constructed by PCR overlap extension mutagenesis from the wild-type vector (pFUSE-hIgG1-Fc-TP-LH309/310CL) as the template using pairs of internal mismatched primers for each mutant as follows.

```
N297A:
5'-GAGCAGTACGCCAGCACGTAC-3'/
3'-CTCGTCATGCGGTCGTGCATG-5';

N563A:
5'-CCCTGTACGCCGTGTCCCTG-3'/
3'-GGGACATGCGGCACAGGGAC-5';

D221N:
5'-GTTAGATCTAACAAAACTCAC-3'/
3'-CAATCTAGATTGTTTTGAGTG-5';

L448STOP:
5'-TCTCCGGGTAAATGAGTCCTAGGACCC-3'/
3'-AGAGGCCCATTTACTCAGGATCCTGGG-5';

C575A:
5'-ACCCTGCTTGCTCAACTCT-3'/
3'-GGCCAGCTAGCTCAGTAGGCGGTGCCAGC-5';
```

-continued

```
N297A/N563A:
primer pair N563A was used on the N297A mutant
plasmid;

D221N/N297A:
primer pair N297A was used on D221N mutant
plasmid;

D221N/N563A:
primer pair N563A was used on the D221N mutant
plasmid;

D221N/N297A/N563A:
primer pair N563A was used on the D221N/N297A
mutant plasmid;

N563A/C575A:
primer pair C575A was used on the N563A mutant
plasmid.
```

The following flanking primers were used in the overlap PCR. These are 5'-ACCCTGCTTGCTCAACTCT-3' and 3'-TGGTTTGTCCAAACTCATCAA-5' which are 71 or 22 base pairs upstream or downstream of the EcoRI/BglII and NheI (all from New England Biolabs) sites used in subcloning into the wild-type vector. DNA coding for the human IgA tailpiece (PTHVNVSVVMAEVDGTCY) was synthesised by EUROFINS and cloned as an AvrII/NheI fragment into pFUSE-hIgG1-Fc-TP-LH309/310CL. To verify incorporation of the desired mutation and to check for PCR-induced errors, the entire coding sequence of the new expression plasmids were sequenced on both strands using the same set of flanking primers. CHO-K1 cells (European Collection of Cell Cultures) were transfected with plasmid using FuGene (Promega) and positive clones selected, expanded and purified as previously described for hexa-Fc[2,3].

Enzymatic Release of N-Linked Glycans.

Recombinant proteins (50 μg) were fractionated by SDS-PAGE on Novex® NuPAGE Bis-Tris 4-12% pre-cast gels (Life Technologies, UK) under reducing condition. After staining with Coomassie Blue, gel bands were excised, washed five times with alternating acetonitrile and water, and air-dried. Each gel band was rehydrated in a reaction buffer (250 μL of 50 mM $NaHCO_3$ pH 7.4) containing 500 units/mL protein N-glycosidase F (PNGase F) (New England Biolabs, UK) and incubated at 37° C. for 16 h. The released glycans were extracted from the gel matrix by washing three times with water and then dried in a SpeedVac Concentrator Plus (Eppendorf, UK).

Fluorescent Labeling of N-Linked Glycans.

PNGase F-released glycans were fluorescently-labelled with 2-aminobenzoic acid (2-AA) as previously described[31]. Briefly, glycans were re-suspended in 30 μL of water, followed by addition of 80 μL of labelling mixture (3% w/v 2-AA, 4.5% w/v sodium cyanoborohydride, 4% w/v sodium acetate trihydrate and 2% w/v boric acid in methanol). After incubation at 80° C. for 1 h, samples were diluted with 1 mL of 97% v/v acetonitrile before being loaded onto Speed Amide-2 cartridges (Applied Separations, UK) and eluted with 2 mL of water to remove excess label.

Exoglycosidase Sequencing of N-Linked Glycans.

The 2-AA labelled glycans were sequentially digested using the following exoglycosidases: α2-3,6,8 neuraminidase from *Clostridium perfringens* (New England Biolabs, UK), β1,4-Galactosidase from *Bacteroides fragilis* (New England Biolabs, UK), α-L-Fucosidase from Bovine Kidney (Sigma-Aldrich, UK), β-N-Acetylglucosaminidase from *Xanthomonas manihotis* (New England Biolabs, UK), and α(1-2,3,6)-mannosidase from Jack Bean (Sigma-Aldrich, UK). Endoglycosidase H (endoH) from *Streptomyces picatus* (New England Biolabs, UK) was used for quantification of oligomannose structures. Digestions were carried out in an incubation buffer (50 mM sodium phosphate, pH 5.0) at 37° C. for 16 h. A polyvinylidene difluoride (PVDF) protein-binding membrane plates (Millipore, UK) were used for removal of enzymes prior to HILIC-UPLC analysis.

HILIC-UPLC

Fluorescently labelled glycans were separated by HILIC-UPLC using a 2.1 mm×10 mm (1.7 μm particle size) ACQUITY Ethylene Bridged Hybrid (BEH) glycan column (Waters, UK) on a Waters ACQUITY UPLC® instrument. The following gradient was run: time=0 min (t=0): 22% A, 78% B (flow rate of 0.5 mL/min); t=38.5: 44.1% A, 55.9% B (0.5 mL/min); t=39.5: 100% A, 0% B (0.25 mL/min); t=44.5: 100% A, 0% B; t=46.5: 22% A, 78% B (0.5 mL/min), where solvent A was 50 mM ammonium formate, pH 4.4, and solvent B was acetonitrile. Fluorescence was measured using an excitation wavelength of 250 nm and a detection wavelength of 428 nm. A 2-AA labelled glucose homopolymer ladder (Ludger, UK) was used as a calibration standard for UPLC analysis of glycans. Data processing was performed using Empower 3 software. The percentage abundance of oligomannose- and complex-type glycans were calculated by integration of the relevant peak areas before and after EndoH digestion and following normalisation.

Receptor and Complement Binding Assays

Methods describing the binding of mutants to tetrameric human DC-SIGN, C1q and C5b-9 have been described previously[3]. ELISAs were used to investigate the binding of oligomeric Fc mutants to FcγRI, FcγRIIA, FcγRIIB, FcγRIIIA and FcγRIIIB (all from R&D laboratories). Receptors were coated down to ELISA plates (Nunc) in carbonate buffer pH9 (Sigma-Aldrich) at 2 μg/ml overnight at 4° C. Plates were then blocked in PBS/0.1% Tween-20 (PBST) containing 4% skimmed milk (Tesco). Plates were then washed three times in PBS/0.1% Tween-20 (PBST) before adding Fc mutants at the indicated concentrations in PBST overnight at 4° C. Plates were washed as above and incubated for 2 h with 1:500 dilution of an alkaline phosphatase conjugated goat $Fab'_2$ anti-human IgG (Jackson Laboratories). Plates were washed as above and developed for 15 min with 100 μl of a Sigmafast p-nitrophenyl phosphate solution (Sigma-Aldrich). Plates were read at 405 nm and data plotted with Graphpad prism.

Negative Ion ESI MS/MS Analysis of N-Linked Glycans

The identity of the glycans was confirmed by negative ion ESI MS/MS using unlabeled glycans cleaned with a Nafion 117® membrane. Static nano-electrospray mass spectrometry was performed with a Waters Synapt G2-Si HDMS ion mobility quadrupole-time-of-flight instrument. Samples in 1:1 (v/v) methanol:water containing 0.5 mM ammonium phosphate (to ensure maximum formation of phosphate adducts) were infused through platinum-palladium-coated borosilicate capillaries prepared in-house. The ion source conditions were: temperature, 80° C.; infusion needle potential, 1.2 kV; cone voltage 100 V. The traveling-wave ion-mobility cell (nitrogen) was operated with a wave velocity of 450 m s-1 and a wave height of 40 V. For MS/MS data acquisition, the parent ion was selected at low resolution (about 4 m/z mass window) and fragmented in the transfer cell with argon. The voltage on the collision cell was adjusted with mass to give an even distribution of fragment ions across the mass scale. Typical values were 80-120 V. Spectra (2 s scans) were acquired with a digitization rate of 4 GHz and accumulated until a satisfactory signal:noise ratio had been obtained. Other operating voltages were as recommended by the manufacturer. Instrument control, data acquisition, and processing were performed with MassLynx software Version 4.1, and Waters DriftScope software was used to extract singly charged glycan ions from the total profile and to reject MS/MS fragment ions that were not associated with the target glycan. Glycan fragments were labelled according to the scheme proposed by Domon and Costello[4].

Results—1

Glycosylation Influences the Oligomerization State of Hexa-Fc

To determine the contribution of the two N-linked glycans in hexa-Fc to oligomerization, we created a panel of mutants by site-directed mutagenesis using the previously described hexa-Fc as template (FIG. 1)[2,3]. Following transfection of mutant IgG1-Fcs into CHO cells, stable cell lines were established, and the secreted Fcs were purified by protein G affinity chromatography. Typical yields for these mutants determined by sandwich ELISAs against titrations of IVIG are wild-type hexa-Fc=2.87 μg/ml; D221N=9.2 μg/ml; N297A=0.87 μg/ml; N563A=1.57 μg/ml; N297A/N563A=0.72 μg/ml; D221N/N563A=0.63 μg/ml; D221N/N297A=0.25 μg/ml; D221N/N297A/N563A=2.9 μg/ml, C575A=20 μg/ml.

Purified IgG1-Fc mutants were then analysed by SDS-PAGE electrophoresis and immunoblotting with a (Fab)2 anti-human IgG-Fc (FIG. 2). When analysed under non-reducing conditions (FIG. 2A), the hexa-Fc migrated as oligomers, corresponding to pentamers and hexamers as described previously[2,3]. The N297A mutant resulted in a slight lowering of the molecular weight of these oligomeric forms commensurate with the loss of glycans at Asn297.

Since removal of the tailpiece glycan (Asn563) in IgM has been shown to enhance polymer formation, mostly an increase in hexamers over pentamers, we reasoned that a similar mutation introduced into hexa-Fc would also lead to enhanced hexamer formation. To our surprise >95% of both the N563A and D221N/N563A mutants in which the tailpiece glycan was removed, migrated as higher order polymers (HOP) of approximately ~650 and 750 kDa respectively (FIG. 2A,C), which corresponded to a dodecameric species by size-exclusion chromatography (FIG. 7). Removal of both Asn297 and Asn563 glycans resulted in molecules that were unable to form oligomers and are expressed poorly by CHO-K1 cells. By running these mutants under reducing conditions we were able to determine the relative sizes of the various glycans attached at each position, such that Asn221 was larger than Asn563, which in turn was larger than Asn297 (FIG. 2B).

We confirmed that the glycans attached at Asn221 in the D221N/N297A/N563A mutant were indeed larger and more complex by normal-phase high-performance liquid chromatography analysis (FIG. 8). This analysis also demonstrated that the glycans attached to Asn297 were smaller and less complex than those attached to Asn563 in the tailpiece, while confirming the complete absence of glycans from the N297A/N563A double mutant (FIG. 8).

The N297 Glycan is Critical for Interactions of Hexa-Fc with Receptors

To determine which N-linked glycan on hexa-Fc contributes to receptor binding, we investigated the interaction of this panel of N-glycosylation mutants with soluble recombinant tetrameric human DC-SIGN (FIG. 3) and human FcγRs (FIG. 4) by ELISA. As previously published hexa-Fc bound to DC-SIGN and to the classical FcγRs. Removal of Asn297 resulted in a dramatic loss of binding to DC-SIGN and the FcγRs, while removal of Asn563 had only a minor effect (FIGS. 3 & 4). A similar important contribution of the Asn297 glycan to DC-SIGN binding was seen with the D221N/N297A mutant (FIG. 3). The lack of binding to DC-SIGN by the D221N/N297A mutant but not the D221N molecule supports our previous observations that oligomannose type glycans found on Asn297 are critical for interactions with DC-SIGN, and that neither Asn221 or Asn563 make a contribution to binding when the Fc is presented as oligomers.

The oligomeric structure of hexa-Fc allows for strong binding to C1q and permits C5b-9 deposition. To investigate which N-linked glycan on hexa-Fc is important for C1q binding and C5b-9 deposition, we screened the panel of mutants for binding to C1q and C5b-9 deposition by ELISA (FIG. 5). Binding to C1q and subsequent C5b-9 deposition was critically dependent on the presence of the Asn297 glycan since removal of the Asn563 tailpiece sugars in either the N563A or D221N/N563A mutants had little effect on complement activation (FIG. 5). Attachment of an additional glycan to the N-terminal hinge as seen in the D221N panel of mutants reduced overall interactions with C1q that are clearly dependent on the presence of the Asn297 glycan (FIG. 5).

The Eighteen Amino Acid C-Terminal IgM-Tailpiece, and in Particular Cys575, is Critical to the Formation of Oligomeric IgG1-Fcs To investigate the structural features of the human IgM tailpiece required for oligomerisation and function of hexa-Fc, we generated three additional mutants; including L448STOP, C575A and N563A/C575A (FIG. 1). Deletion of the entire tailpiece by stop codon introduction completely prevented the formation of higher order oligomers, although a very small proportion of dimers could still be seen (FIG. 2C). In the absence of the tailpiece the small proportion of dimers observed can only arise through inter-monomeric disulphide bridging at Cys309, the only other available free Cys residue found in hexa-Fc. Similarly, substitution of the penultimate residue of the tailpiece, Cys575, with alanine resulted in the secretion of IgG-Fc monomers alone (FIG. 2C). The two monomeric species seen at approximately 53 and 58 kDa with this C575A mutant most likely represent differentially glycosylated monomers as two N-linked sites N297 and N563 are available in this molecule. Substitution of Asn563 with alanine to prevent attachment of N-linked carbohydrate to the tailpiece resulted in the formation of higher order oligomers, most likely dodecamers (FIG. 2A,C). Deletion of both Asn563 and Cys575 in the tailpiece double-mutant (N563A/C575A) resulted in a laddering pattern of different molecular weights of ~50, 100, 150, 200, 250, 300, 350 and 400 kDa that most likely represent monomers, dimers, trimers, tetramers, pentamers and hexamers, although molecules as large as dodecamers as seen with N563A mutant were never observed (FIG. 2C). These most likely arise through disulphide bond formation between Cys309 of two adjacent monomers (FIG. 6).

We next investigated the functionality of these tailpiece mutants with respect of DC-SIGN binding and complement activation. The laddered oligomers formed in the N563A/C575A mutant were fully competent with respect to DC-SIGN binding (FIG. 3), FcγR binding (FIG. 4) and complement activation (FIG. 5A,B). The absence of the tailpiece carbohydrate in the N563A/C575A double-mutant fully supports our earlier observations that DC-SIGN binding is fully dependent on Asn297. Despite being expressed almost entirely as monomers, the C575A mutant was still capable of binding DC-SIGN, compare C575A against wildtype monomeric IgG-Fc (FIG. 3). The binding of the C575A mutant to all the FcgRs was otherwise broadly similar to the wildtype IgG1-Fc or L448STOP controls (FIG. 4). Although the C575A mutant bound C1q poorly by comparison to polymers (FIG. 5A), it was unable to activate complement as determined by C5b-9 deposition (FIG. 5B).

Discussion—1

We previously demonstrated the importance of carbohydrate to the binding of hexa-Fc to DC-SIGN and to the activation of the complement cascade[3]. In this study we used a protein engineering approach to determine the structural features of hexa-Fc required for oligomerisation and binding to receptors. We first investigated the relative contributions of two N-linked glycosylation sites found at Asn297 in the Cγ2 domain and Asn563 located in the eighteen amino-acid IgM tailpiece of hexa-Fc.

Human IgA and IgM antibodies that polymerize differ from other isotypes in possessing an eighteen amino acid C-terminal extension of the heavy chain termed the tailpiece, which previous studies have implicated in polymerization of monomer subunits in both IgA and IgM. In line with these earlier studies we found that complete removal of the tailpiece from hexa-Fc as in the L448STOP mutant resulted in proteins that were mostly monomeric, although a very small proportion of dimers were observed (FIG. 2C).

Intriguingly, removal of the tailpiece carbohydrate at Asn563 has been shown to enhance oligomer formation in IgM while reducing oligomerisation in IgA and we therefore wondered what impact removal of Asn563 would have on hexa-Fc containing an IgG1-Fc backbone. Remarkably, >95% of both the N563A and D221N/N563A mutants were secreted as discrete dodecameric species (~650 & ~700 kDa respectively) and no hexamers, pentamers or tetramers were observed as seen previously with the IgM (FIGS. 2A and C FIG. 7). In contrast with hexa-Fc, the formation of dodecameric IgM, dodecameric IgGs, or even dodecameric IgA is likely not possible given additional constraints imposed by the size of the Fc (extra Cμ2 domain in the Fc of IgM) and associated $F(ab)_2$ arms in each monomer of the heavy chains of these antibody types. Therefore the lack of bulky carbohydrates in the tailpiece, the absence of both Fab domains and the extra constant domain in the Fc, allows more of the unstructured tailpieces in the N563A or D221N/N563A mutants to form inter-monomeric disulphide bonds via Cys575, thus allowing for the optimal formation of dodecamers over other polymeric species described previously (FIG. 6). Despite their increased valency no improvement in the ability of either the N563A or D221N/N563A mutants to bind DC-SIGN or activate complement were observed (FIGS. 3 and 5).

Furthermore, the N563A, D221N/N563A, and the N563A/C575A mutants all show that binding to DC-SIGN is totally dependent on the presence of Asn297. These mutants may therefore have beneficial utility in various therapeutic applications where enhanced valence is required at no cost to receptor binding or complement activation, for example in the delivery of more copies of antigen in vaccine applications.

This study also expands our knowledge about the influence of glycosylation on Fc activity. Under normal circumstances, a single N-linked glycosylation site exists at amino acid 297 in the Cγ2 domain of all IgG subclasses, that we and others have shown is critical for interactions with DC-SIGN. We therefore hypothesised that the addition of an extra N-linked carbohydrate into an exposed region of the Fc would enhance interactions with glycan receptors like DC-SIGN. We therefore engineered an additional N-linked sequon at position 1 of the Fc polypeptide chain (FIGS. 1 and 2) to produce the D221N series of mutants. We show for the first time that it is possible to add N-linked glycans to the N-terminus of the hinge of IgG1-Fc to generate a molecules that are still capable of oligomerising into hexamers (FIGS. 2A and C). This was unanticipated, as N-linked glycans are not typically attached to the hinges of native IgG molecules (or of other classes of antibody), as they are presumed to interfere with disulphide bond formation and the capacity of the hinge to therefore act as a flexible linker. Native antibodies e.g. IgA tend to 0-glycosylate their hinges for this reason. Despite containing larger more complex glycans (FIG. 8) no improvement in binding to either DC-SIGN (FIG. 3) or C1q (FIG. 4) over hexa-Fc was observed with the D221N panel of mutants. However, we did observe enhanced binding of the D221N/N563A mutant to FcγRIIIA (FIG. 4), which may be relevant to diseases where IVIG is beneficial, and where the efficacy of treatment has been shown to be FcgRIIIA dependent. We therefore anticipate that monomers based on C575A into which the D221N glycan is inserted may have superior binding to both DC-SIGN and FcγRIIIA.

Since removal of the tailpiece in toto (the L448STOP mutant) resulted in the formation of a small proportion of dimers (FIG. 2C), presumably through inter-monomer disulphide bridges via Cys309 in the Cγ2 domain of hexa-Fc, we engineered two further tailpiece mutants in the presence or absence of Asn563 to explore the role of the tailpiece Cys575 to oligomerization and receptor binding via Asn563 (FIG. 1). Removal of Cys575 without loss of the Asn563 glycan resulted in molecules that mostly formed monomers (FIG. 2C). Monomers of C575A (in contrast to the monomeric IgG1-Fc control) could bind DC-SIGN and poorly to C1q, but were unable to activate complement activation as determined by C5b-9 deposition. This shows that Asn563 glycans can interact with receptors but that the binding sites are lost when Asn563 competent proteins are expressed as oligomers, as seen with the Asn563 competent mutants, N297A and D221N/N297. The presence of the Asn563 glycan in the absence of disulphide mediated oligomerization through Cys575 presumably restrains further disulphide bridging via Cys309 (FIG. 6) while allowing for interactions with DC-SIGN in the absence of complement activation. Surprisingly, removable of both Asn563 and Cys575 still allowed for the formation of oligomers of various molecular weights that in the absence of any other free cysteines must arise through Cys309 (FIG. 6). In the case of the N563A/C575A oligomers all the binding to DC-SIGN now being contributed by interactions via glycans on Asn297. Intriguingly, these N563A/C575A laddered oligomers bound FcγRI poorly by comparison to hexa-Fc, and were no better than hexameric-Fc at engaging all the other low-affinity FcγRs, suggesting that these constructs may not be optimal for use in vaccine approaches that require FcγRI. In the absence of both Cys575 and Asn563, other amino-acids within the eighteen amino-acid tailpiece must favour interactions between individual Fc-monomers that then allow for disulphide bond formation via Cys309 (FIG. 6).

Taken together, our results suggest that the Asn563 tailpiece glycans serve as spacers, limiting to five or six the number of monomeric IgG1-Fc subunits that can be incorporated into an oligomer (FIG. 6). As oligomers, binding to DC-SIGN and C1q are entirely dependent on glycans attached at Asn297, as those found on Asn563 are buried in oligomers, only becoming available to receptor interactions when found in the context of monomeric IgG1-Fcs, such as the protein of SEQ ID NO: 2 described here. Generating oligomeric Fcs for therapeutic applications brings significant bioprocessing and safety issues that are not found with monomeric Fc or Fc-fusion proteins, and therefore recombinant monomeric Fcs that bind DC-SIGN (and potentially other glycan receptors), and FcγRIIIA in the case of D221N/C575A, but do not activate complement, as in the C575A mutant, may have significant therapeutic potential as improved biomimetics for IVIG.

Results—2

Glycosylation Influences the Multimerisation State of Hexa-Fc

To determine the contribution of two N-linked glycans in hexa-Fc to multimerisation and receptor binding, we created a panel of glycosylation mutants by site-directed mutagenesis using the previously described hexa-Fc as the template (FIG. 9)[2,3]. We also inserted an additional N-linked attachment site at the N-terminus (D221N) to investigate the impact of additional glycosylation on hexa-Fc function (FIG. 9).

Following transfection of these mutated IgG1-Fc DNAs into Chinese Hamster Ovary (CHO)-K1 cells, stable clonal cell lines were established, and the secreted Fcs were purified by protein A/G affinity chromatography[2]. The purified IgG1-Fc proteins were analysed by SDS-PAGE and immunoblotting with anti-human IgG-Fc (FIG. 10). When analysed under non-reducing conditions (FIG. 10 A), the hexa-Fc migrated as monomers and multimers, corresponding to tetramers, pentamers and hexamers as described previously[2,3]. The N297A mutant resulted in a slight lowering of the molecular weight of all these multimeric forms commensurate with the loss of the glycan at Asn297 (FIG. 15 D), as described previously[3]. Therefore Asn297 does not contribute to multimerisation.

Since removal of the tailpiece glycan (Asn563) in IgM has been shown to enhance multimer formation, mostly as an increase in hexamers over pentamers, we reasoned that a similar mutation introduced into hexa-Fc would also lead to enhanced hexamer formation. Removal of Asn563, as in the N563A, N297A/N563A, D221/N563A and D221/N297A/N563A mutants, led to the formation of higher ordered multimers (HOO) whose molecular weight (~650-700 kDa) corresponded to dodecameric forms by size-exclusion chromatography (FIG. 10 A, arrowed and FIG. 7 for N563A). The type of multimers produced were unaffected by the addition of glycans at Asn221 (D221N), with all the molecular weights for the D221N molecules being larger than molecules in which Asn221 was absent (FIGS. 10 A and B).

By running these mutants under reducing conditions we were able to determine the relative sizes and occupancy of the various glycans attached at each position, showing that the Asn221 and Asn563 attached glycans are larger than those attached to Asn297 (FIG. 10 B). These observations on the molecular weights of the various glycoforms were also confirmed by HILIC-UPLC analysis of the carbohydrates as described below (FIG. 11 and FIG. 15).

N-Linked Glycoprofiling of Hexa-Fc Proteins

Glycans were released from purified Fc constructs via protein N-glycosidase F (PNGase F). The free sugars were fluorescently labeled and resolved via hydrophilic interaction chromatography (HILIC) using the AQUITY UPLC® Ethylene Bridged Hybrid (BEH) amide column. The HILIC-UPLC spectra from the Fc mutants expressed in CHO-K1 cells are shown in FIG. 11.

The glycans from IgG1-Fc are composed of a series of fucosylated, biantennary, complex-type carbohydrates, typical of the protein-directed glycosylation observed for IgG (FIG. 11 A). The most abundant species observed were galactosylated structures, a very small population (~2%) of sialylated material, and a complete absence of oligomannose structures (Table 3), findings that are broadly consistent with previous observations[3]. In contrast, hexa-Fc displayed a two-fold reduction in galactosylated sugars and enhanced oligomannose-type ($Man_5GlcNAc_2$, $Man_6GlcNAc_2$) structures, consistent with a previous observation for their putative contribution to DC-SIGN binding (FIG. 11 A and Table 3). The loss of $Man_5GlcNAc_2$ and $Man_6GlcNAc_2$ structures in the N563A and D221N/N563A multimers show that these oligomannose structures are attached at Asn563 in the tailpiece and not at Asn297 as previously modelled.

Tri-antennary species, not normally observed on the Fc, were detected on hexa-Fc (FIG. 11 A, FIG. 15). Additionally, increased terminal sialylation was also prominent on the hexa-Fc. Unusual di- and tri-galactosylated, di- and tri-sialylated species were also detected in the HILIC-UPLC spectra of hexa-Fc. Similar unusually sialylated structures have been detected in mouse serum glycoproteins, and all are attached via α2,3 linkages, as expected for proteins expressed by CHO-K1 cells. The structural assignments were confirmed by electrospray mass spectrometry for all the recombinant Fc proteins (FIGS. 14 and 16). The loss of these sialylated structures in the N563A mutant shows that these complex structures must be located on the tailpiece Asn563 glycan in hexa-Fc (FIG. 11 A). Under reducing conditions, the N563A mutant appeared as two separate bands. N-linked glycan analyses of these two bands revealed them to contain similar glycoprofiles but in different proportions (FIG. 11 A).

We generated the novel D221N series of mutants to investigate if N-linked sugars could be attached to the exposed N-terminus of the hinge, and what the impact of such glycosylation would be on glycan processing at Asn297 and Asn563 (FIG. 9). The addition of D221N onto the hexa-Fc scaffold doubled the overall sialic acid content while reducing the oligomannose-type glycans (Table 3 and FIG. 11 B). The D221N mutation was clearly the main driver for extensive sialylation, as the removal of both Asn297 and Asn563 in the D221N/N297A/N563A mutant resulted in recombinant multimers whose glycan composition was 75% sialylated with complete loss of oligomannose and a six-fold reduction in galactosylated glycans that would normally be located on Asn297 in the hexa-Fc (FIG. 11 B and Table 3). As expected, no glycans could be detected on the glycosylation-deficient double mutant N297A/N563A, and only weak signals that could not be assigned specific structures were observed for the N297A mutant (FIG. 15).

The Asn297 Glycan is Critical for Interactions of Hexa-Fc with DC-SIGN but not Siglec-1

To determine which N-linked glycan on the hexa-Fc contributes to receptor binding, we investigated the interaction of the panel of N-glycosylation mutants with soluble recombinant tetrameric human DC-SIGN by ELISA (FIG. 12 A). As previously published, hexa-Fc bound DC-SIGN[2, 3]. Removal of Asn297 resulted in a dramatic loss of binding to this receptor, while removal of Asn563 (as in the N563A mutant) had only a minor effect (FIG. 12 A). The loss of $Man_6GlcNAc_2$ and $Man_6GlcNAc_2$ in the N563A mutant (FIG. 11 A) that still binds DC-SIGN highlights that oligomannose structures are not necessary for DC-SIGN interactions by multimers, and that other glycan structures found at Asn297 are involved. A similar important contribution of the Asn297 glycan to DC-SIGN binding was seen with the D221N series of mutants, which all possessed reduced interactions with DC-SIGN compared to the controls that lack the D221N insertion (FIG. 12 A). This shows that the presence of the N-linked glycan at Asn221 can negatively affect interactions mediated via the Asn297 glycan. The lack of binding to DC-SIGN by both the D221N/N297A and D221N/N297A/N563A mutants, whose glycans are respectively 73% and 75% sialylated, also shows that α2,3-linked sialic acid containing structures do not make a significant contribution to human DC-SIGN binding, while confirming the critical role of Asn297 to binding.

Although we tentatively suggested that oligomannose may make a contribution to DC-SIGN binding by the hexa-Fc (14% oligomannose)[3], the requirement for oligomannose in DC-SIGN binding is clearly not essential, as the N563A and N563A/C575A mutants that are both devoid of oligomannose can still bind DC-SIGN (FIG. 15, Table 3), although not as well as hexa-Fc (FIG. 12 A). The data from these two mutants, whose glycosylation profiles were very similar to monomeric IgG1-Fc, shows that glycan structures other than oligomannose on Asn297 can contribute to DC-SIGN binding (FIG. 10 A). This finding may also provide a rational explanation for our previous conflicting observation that Endo H treatment of hexa-Fc did not abrogate DC-SIGN binding.

The remarkable sialylation profile of the D221N series of mutants (FIG. 11 B and Table 3 and FIG. 15) led us to investigate interactions with the sialic acid-dependent human receptor Siglec-1 (FIG. 12 B). Human Siglec-1, also known as sialoadhesin or CD169, is a cell surface receptor restricted to monocytes and macrophages with a predilection for α2,3 glycosidic linkages. All the D221N panel of Fc proteins bound Siglec-1 irrespective of the presence or absence of either Asn297 or Asn563 (FIG. 12 B). Indeed binding by the D221N/N297A/N563A mutant shows that Asn221 is sufficient for this interaction with Siglec-1 to occur. As expected, the complete absence of carbohydrate (as found in the N297A/N563A double-knockout), or the absence of sialic acid-containing glycans (as in the IgG1-Fc monomer) led to proteins that are unable to bind Siglec-1 (FIG. 12 B). We have also investigated binding to Siglec-2 (CD22), a receptor that has a binding preference for α2,6 glycosidic linkages, and observed little or no binding of these α2,3 linked sialo-Fcs to Siglec-2 (data not shown).

The Asn297 Glycan is Critical for Interactions of Hexa-Fc with the Classical Fcγ-Receptors and Complement We next investigated which of the N-linked glycans on the hexa-Fc contributes to Fcγ-receptor (FcγRs) binding (FIG. 13). As previously published, hexa-Fc bound with avidity and specificity to all the human FcγRs investigated[3]. Removal of Asn297 in either the N297A or D221N/N297A mutants completely abolished binding to all the human FcγRs, demonstrating a clear requirement for this Asn297 glycan in interactions with FcγRs. Attachment of N-terminal glycans at Asn221 inhibited binding to all FcγRs, although the removal of N563A in the tailpiece reinstated binding of the D221N-containing mutant (D221N/N563A) to FcγRs, and in particular to FcγRIIIA. Thus the N563A tailpiece glycan is not required for binding to FcγRs.

The multimeric structure of hexa-Fc also enables strong activation of the classical complement pathway. To investigate which N-linked glycan on the hexa-Fc is important for C1q binding and C5b-9 deposition, we screened the panel of mutants by ELISA (FIG. 5A). Binding to C1q and subsequent C5b-9 deposition was critically dependent on the presence of the Asn297 glycan. Removal of the Asn563 tailpiece carbohydrate in either the N563A or D221N/N563A mutants had little effect on complement activation, in stark contrast to all the mutants where Asn297 was absent (FIG. 5A). The addition of an N-linked carbohydrate to the N-terminus of the hinge (D221N and D221N/N563A)

reduced both C1q binding and complement activation, compared to equivalent proteins that lack Asn221 (FIG. 5A). Thus the presence of Asn297 is essential for complement activation in multimers.

The Eighteen Amino Acid C-Terminal Tailpiece, and in Particular Cys575, is Critical in the Formation of Multimeric IgG1-Fc To investigate the structural features of the human IgM tailpiece required for multimerisation and function of the hexa-Fc, we generated further mutants, including L448STOP, C575A, N563A/C575A, D221N/N297A/C575A, D221N/N563A/C575A, and hexa-Fc-IgA-tp where the eighteen amino-acid tailpiece from IgM was replaced with that from human IgA (FIG. 9). Deletion of the entire tailpiece by stop codon introduction (L448STOP) completely prevented the formation of higher order multimers, although a very small proportion of dimer and other multimers could still be seen (FIG. 10 C). In the absence of the entire tailpiece, the small proportion of multimers and dimer observed can only arise through inter-monomeric disulphide bridging at Cys309 (FIG. 14). Similarly, substitution of the Cys575 residue of the tailpiece with alanine resulted in the secretion of mostly IgG-Fc monomers but there is also evidence of a small proportion of higher order multimers (FIG. 10 C). It is intriguing that the introduction of a glycan at D221 together with the C575A mutation yields only monomers in the presence of Asn563 (FIG. 10 D). This shows that the Asn221 hinge glycan may constrain multimerisation mediated either through Cys309 or the tailpiece.

Deletion of both Asn563 and Cys575 in the tailpiece (N563A/C575A) resulted in a laddering pattern of different molecular weights from ~50 to greater than 400 kDa (FIG. 10 C), most likely representing monomers, dimers, trimers, tetramers, pentamers and hexamers, although molecules as uniform as those seen with the N563A-containing mutants were not observed (FIG. 10 C). These ladders probably arise through disulphide bond formation between Cys309 of two adjacent monomers (FIG. 14). The introduction of the C575A mutation onto the backbone of D221N/N297A (to generate the D221N/N297A/C575A mutant) resulted in monomers (FIG. 10 D), whereas the introduction of C575A onto the D221N/N563A backbone resulted in a similar laddered pattern of multimers (FIG. 10 D) as seen previously with N563A/C575A (FIG. 10 C).

Replacement of the eighteen tailpiece from IgM with that from IgA resulted in a homogeneously multimeric protein, indicating that amino acids other than Asn563 and Cys575 in the IgM-tailpiece are involved in determining the overall valence and quaternary structure of the multimer assembly (FIG. 10 E).

Introduction of Cys575 Generates Monomers with Altered Glycosylation Profiles and Enhanced Binding to Glycan Receptors The C575A glycan profile when compared to N563A/C575A shows that the Asn563 glycan in the tailpiece could be sialylated in the C575A monomer (FIGS. 10 C and 11 C). The C575A glycan profile resembles that seen with complex multimers including hexa-Fc (FIG. 11 C and Table 3), with approximately sixteen fold increase in sialylation compared to the IgG1-Fc control (Table 3). The C575A monomer was shown to be fully competent with respect to Siglec-1 binding (FIG. 13), and binding to all the FcγR was broadly similar to the IgG1-Fc or the L448STOP monomer control (FIG. 4 B). In contrast to hexa-Fc, the C575A mutant bound C1q poorly (FIG. 5) and was unable to activate complement as determined by C5b-9 deposition (FIG. 5).

Discussion—2

We previously demonstrated the importance of carbohydrate in the binding of hexa-Fc to DC-SIGN and in the activation of the complement cascade. In this study we used a protein engineering approach to determine the structural features of hexa-Fc required for multimerisation and binding to receptors, by investigating the relative contributions of two N-linked glycosylation sites found at Asn297 in the Cγ2 domain, and Asn563 located in the eighteen amino-acid IgM-tailpiece of hexa-Fc (FIG. 9).

Human IgA and IgM antibodies that multimerise differ from other isotypes in possessing an eighteen amino acid C-terminal extension of the heavy chain termed the tailpiece (tp), which previous studies have implicated in multimerisation of monomer subunits in both IgA and IgM. In line with these earlier studies we found that complete removal of the tailpiece from hexa-Fc, as in the L448STOP mutant, resulted in proteins that were mostly monomeric, although a very small proportion of dimers were observed (FIG. 10 C). Furthermore, attachment of the eighteen amino acid IgA tailpiece, rather than the IgM tailpiece, resulted in a homogeneous preparation of multimers with no monomers, dimers or other lower order multimeric forms being detectable (FIG. 10 E).

The removal of the tailpiece carbohydrate at Asn563 has been shown to enhance multimer formation in IgM while reducing multimerisation in IgA. We therefore wondered what impact the removal of Asn563 would have on hexa-Fc containing the IgG1-Fc backbone and IgM-tailpiece. Remarkably, greater than 95% of proteins from such mutants deficient in Asn563 were secreted with a molecular weight of ~600 kDa, approximating to dodecamers (FIGS. 10 A and 7). There is a precedent for dodecamer formation when the eighteen amino acid tailpiece from IgA was fused to the C-terminus of CD4, although whether dodecamers could arise when the IgM tailpiece is fused to the human IgG1-Fc has not been documented previously.

In contrast to hexa-Fc, the formation of native dodecameric IgM, IgG, IgE, or IgA is unlikely given additional constraints imposed by the size of the Fc (extra Cμ2 domain in the Fc of IgM and IgE) or the associated $F(ab)_2$ arms in each monomer of the heavy chains of these antibody types. Therefore the lack of bulky carbohydrates in the tailpiece, the absence of both Fab domains and the extra C1 constant domain in the Fc of IgM or IgE, allows more of the unstructured tailpieces in the N563A or D22N/N563A mutants to form inter-monomeric disulphide bonds via Cys575, thus allowing for the formation of higher ordered multimers over other multimeric species described previously (FIG. 15). Despite their increased valence, no improvement in the ability of either the N563A or D221N/N563A mutants to bind DC-SIGN or activate complement were observed (FIGS. 12 A and 5 A). Furthermore, the N563A, D221N/N563A, and the N563A/C575A mutants all show that binding to DC-SIGN is totally dependent on the presence of Asn297. These mutants may therefore have beneficial utility in various therapeutic applications where enhanced valence is required at no cost to receptor binding or complement activation, for example in the delivery of more copies of antigen in vaccine applications.

This study also expands our knowledge of glycosylation on Fc activity. Under normal circumstances, a single N-linked glycosylation site exists at amino acid 297 in the Cγ2 domain of all IgG subclasses, that we and others have shown is critical for interactions with FcγRs and DC-SIGN. We therefore hypothesised that the addition of an extra N-linked carbohydrate onto an exposed region of the Fc would enhance interactions with glycan receptors. We have engineered an additional N-linked sequon at position 1 of the Fc polypeptide chain to produce the D221N series of mutants (FIG. 9). We show for the first time that it is possible to add N-linked glycans to the N-terminus of the hinge of IgG1-Fc to generate molecules that are still capable of forming multimers (FIG. 10 A). This was unanticipated, as N-linked glycans are not typically attached to the hinges of native IgG molecules (or of other classes of antibody), as they are presumed to interfere with disulphide bond formation and the capacity of the hinge to act as a flexible linker. Native antibodies such as IgA likely O-glycosylate their hinges for this reason. Despite containing larger, more complex glycans (FIGS. 10 and 11 and Table 3) no improvement in binding to either DC-SIGN (FIG. 12 A) or C1q (FIG. 5 A) over hexa-Fc was observed with the D221N panel of mutants. The presence of the introduced glycan at Asn221 seems to have a detrimental effect on FcγR binding, presumably by interfering with the FcγR binding site located within the lower hinge region. The Asn221 attached glycans are larger than those found at Asn297 (FIGS. 7 and 11) and therefore, as already shown with multimeric Fc-fusions to antigens, their presence may interfere with FcγR binding. Although this may be the case for D221N hexamers, it clearly does not hold for the D221N/N563A that had markedly improved binding to FcγRIIIA (FIG. 4 A). We do not yet know the structure of the higher order multimers, but this data might anticipate subtle differences in their structure compared to hexa-Fc.

Since removal of the tailpiece in toto (the L448STOP mutant) resulted in the formation of a small proportion of dimers (FIG. 10 C), presumably through inter-monomer disulphide bridges via Cys309 in the Cγ2 domain of hexa-Fc, we engineered two further tailpiece mutants in the presence or absence of Asn563 to explore the role of the tailpiece Cys575 in multimerisation and receptor binding (FIG. 9). Removal of Cys575 without loss of the Asn563 glycan resulted in molecules that mostly formed sialylated monomers (FIGS. 10 C and 11 C). The monomeric C575A mutant could bind Siglec-1 (FIG. 13) and was comparable to the D221N mutant in respect of DC-SIGN binding, however the C575A monomer was still able to bind FcγRs and, like the IgG1-Fc control monomer, was unable to activate complement (FIG. 7).

The presence of the Asn563 glycan in the absence of disulphide-mediated multimerisation through Cys575 presumably restrains further disulphide bonding via Cys309 (FIG. 14), thus favouring the formation of monomers and allowing for interactions with glycan receptors such as Siglec-1 in the absence of complement activation (FIG. 7 and FIG. 13).

Surprisingly, removal of both Asn563 and Cys575 still allowed for the formation of multimers of various molecular weights that, in the absence of any other free cysteines, must arise through Cys309 (FIG. 14). In the case of the N563A/C575A multimers, all the binding to DC-SIGN is now due to interactions via glycans attached to Asn297. In the absence of both Cys575 and Asn563, other amino-acids within the eighteen amino-acid tailpiece must allow for interactions between individual Fc-monomers that then allow disulphide bond formation via Cys309 (FIG. 14), which cannot occur with the L448STOP mutant in which the whole tailpiece was removed. The hypothesis that other tailpiece residues, other than Asn563 and Cys575 are involved in determining the final quaternary structure of hexa-Fc, is supported by the finding that the use of the IgA-tailpiece instead of that from IgM leads to improved multimerisation and yields of hexameric IgG1-Fc (FIG. 10 E).

Taken together, our results show that the Asn563 tailpiece glycan serves as a spacer, limiting to five or six the number of monomeric IgG1-Fc subunits that can be incorporated into an multimer (FIG. 14). As multimers, binding to glycan receptors is entirely dependent on glycans attached at Asn297, as the glycans at Asn563 are buried in multimers, only becoming available to influence receptor interactions when found in the context of monomeric IgG1-Fcs, such as the C575A mutant.

IgG-Fc sialylation has emerged as an important but controversial concept for regulating anti-inflammatory activity of antibodies[6]. Translating this concept to potent anti-inflammatory therapies has been hampered by the difficulty of generating suitably enriched sialylated products for human use. All approaches to date have focussed on chemical or genetic modifications to the only available N-linked glycan found at position Asn297 in the Fc. We describe two complementary approaches to increasing the sialic acid content of the Fc, first by insertion of the 18 amino acid tailpiece from IgM onto the C-terminus of the IgG1-Fc into which a cysteine-to-alanine substitution is made at Cys575 (FIG. 11 and Table 3), and second by the addition of an extra N-glycan at Asn221. This D221N approach results in significantly higher sialylation over C575A, although whether this translates to greater in vivo efficacy still needs to be determined. Monomers in which all three glycosylation sites (Asn221, Asn297, and Asn563) are sialylated may therefore yield molecules with greater efficacy for use in sialic acid dependent therapies. This approach requires no expensive in vitro enzymatic or complex chemical modifications of the Fc glycan, and no requirement for glycosidase deficient/transgenic cell lines for their manufacture.

Although C-terminal tailpiece sialylation in monomers such as the C575A mutant may appear attractive for therapy, we have recently observed that C-terminal tailpiece additions can favour interactions with other plasma proteins, and therefore hinge focused approaches to enhancing sialylation (as in D221N mutants) may be more tractable for therapeutic development.

Generating commercial multimeric Fcs raises significant bioprocessing and safety issues that are not found with monomeric Fc production. For example, high mannose type glycans found in hexa-Fc have been shown to increase IgG clearance rates due to cellular uptake via the mannose receptor. Recombinant monomeric Fcs developed here that are devoid of oligomannose, and yet show improved binding to selected glycan receptors may therefore have significant therapeutic potential, for example as replacements for IVIG. Furthermore, given the known effects of Fc-sialylation in reducing IgG antibody-dependent cellular cytotoxicity activity, it may also be possible to use the D221N/C575A mutations to develop therapeutic antibodies with modified effector functions.

Multimeric Fcs may nonetheless be useful, for example when delivering antigens in vaccines or as high avidity receptor blockers. Many pathogens rely on glycans to infect host cells, and differentially glycosylated Fc-multimers may be useful inhibitors of infection. One immediate application for our hypersialylated molecules may be to block Siglec-1 dependent trans-infection of lymphocytes by retroviruses, including HIV and human T-cell leukaemia viruses. We anticipate that expression of these mutants in human cell lines e.g. HEK, will bestow hypersialylated molecules with α2,6 linkages with improved binding to α2,6-dependent receptors like Siglec-2 that are implicated in IVIG efficacy. Such receptor mimicry strategies need to overcome the high avidity of the natural receptor generated by the sum of the multiple low-affinity glycan binding sites that may now be achievable with the D221N series of hypersialylated multimers. Thus by adding or removing glycosylation and disulphide bonding sites within hexa-Fc, new portfolios of effector functions can be generated.

REFERENCES

1. Yu, X., Vasiljevic, S., Mitchell, D. a., Crispin, M. & Scanlan, C. N. Dissecting the molecular mechanism of IVIg therapy: The interaction between serum IgG and DC-SIGN is independent of antibody glycoform or Fc domain. *J. Mol. Biol.* 425, 1253-1258 (2013).
2. Mekhaiel, D. N. A. et al. Polymeric human Fc-fusion proteins with modified effector functions. *Scientific Reports* 1, (2011).
3. Czajkowsky, D. M. et al. Developing the IVIG biomimetic, Hexa-Fc, for drug and vaccine applications. *Sci. Rep.* 5, 9526 (2015).
4. B. Domon, C. E. Costello, A systematic nomenclature for carbohydrate fragmentations in FAB-MS/MS spectra of glycoconjugates, Glycoconj J, 5 (1988) 397-409.

TABLE 1

| SEQ ID NO. | Also referred to as | Changes compared to SEQ ID NO: 1 |
|---|---|---|
| 1 | Hexa-Fc | None |
| 2 | C248A | Cysteine at residue 575 substituted with alanine |

TABLE 2

| Residue number in SEQ ID NO: 1 | Residue number in SEQ ID NO: 2 | Also referred to herein as |
|---|---|---|
| Cys248 | Cys248 | Cys575, or position 575 of IgM |
| N77 | N77 | N297 |
| N236 | N236 | N563 |
| D1 | D1 | D221 |
| C89 | C89 | C309 |

TABLE 3

| Samples | Glycan composition (%) | | |
|---|---|---|---|
| | Oligomannose | Galactosylated | Sialylated |
| Hexa-Fc | 14.4 | 32.1 | 23.2 |
| IgG1-Fc | — | 58.6 | 2.3 |
| N563A (upper band) | — | 56.5 | 8.1 |
| N563A (lower band) | — | 41.6 | 2.5 |
| D221N | 11.1 | 23.8 | 40.9 |
| D221N/N297A | 5.3 | 5.1 | 72.6 |
| D221N/N563A | — | 20.9 | 44.8 |
| D221N/N297A/N563A | — | 5.8 | 75.7 |
| C575A | — | 44.3 | 38.4 |
| N563A/C575A | — | 62.9 | — |
| L448STOP | — | 38.1 | 12.2 |

Sequence information

```
SEQ ID NO: 1-Reference protein, also designated "Hexa-Fc or HexaGard"
DKTHTCPPCP APELLGGPSV FLFPPKPKDT LMISRTPEVT CVVVDVSHED PEVKFNWYVD
GVEVHNAKTK PREEQYNSTY RVVSVLTVCL QDWLNGKEYK CKVSNKALPA PIEKTISKAK
GQPREPQVYT LPPSREEMTK NQVSLTCLVK GFYPSDIAVE WESNGQPENN YKTTPPVLDS
DGSFFLYSKL TVDKSRWQQG NVFSCSVMHE ALHNHYTQKS LSLSPGKLVL GPPLYNVSLV
MSDTAGTCY

SEQ ID NO: 2-Protein of the invention also designated "C248A"
DKTHTCPPCP APELLGGPSV FLFPPKPKDT LMISRTPEVT CVVVDVSHED PEVKFNWYVD
GVEVHNAKTK PREEQYNSTY RVVSVLTVCL QDWLNGKEYK CKVSNKALPA PIEKTISKAK
GQPREPQVYT LPPSREEMTK NQVSLTCLVK GFYPSDIAVE WESNGQPENN YKTTPPVLDS
DGSFFLYSKL TVDKSRWQQG NVFSCSVMHE ALHNHYTQKS LSLSPGKLVL GPPLYNVSLV
MSDTAGTAY

SEQ ID NO: 3-DNA sequence for C248A
GACAAAACTCACACATGCCCACCGTGCCCAGCACCTGAACTCCTGGGGGGACCGTCAGTCTTCCTCTTCCCCC
CAAAACCCAAGGACACCCTCATGATCTCCCGGACCCCTGAGGTCACATGCGTGGTGGTGGACGTGAGCCACGA
AGACCCTGAGGTCAAGTTCAACTGGTACGTGGACGGCGTGGAGGTGCATAATGCCAAGACAAAGCCGCGGGAG
GAGCAGTACAACAGCACGTACCGTGTGGTCAGCGTCCTCACCGTCTGCCTCCAGGACTGGCTGAATGGCAAGG
AGTACAAGTGCAAGGTCTCCAACAAAGCCCTCCCAGCCCCCATCGAGAAAACCATCTCCAAAGCCAAAGGGCA
GCCCCGAGAACCACAGGTGTACACCCTGCCCCCATCCCGGGAGGAGATGACCAAGAACCAGGTCAGCCTGACC
TGCCTGGTCAAAGGCTTCTATCCCAGCGACATCGCCGTGGAGTGGGAGAGCAATGGGCAGCCGGAGAACAACT
ACAAGACCACGCCTCCCGTGCTGGACTCCGACGGCTCCTTCTTCCTCTACAGCAAGCTCACCGTGGACAAGAG
CAGGTGGCAGCAGGGGAACGTCTTCTCATGCTCCGTGATGCACGAGGCTCTGCACAACCACTACACGCAGAAG
AGCCTCTCCCTGTCTCCGGGTAAATTAGTCCTAGGACCCCCCCTGTACAACGTGTCCCTGGTCATGTCCGACA
CAGCTGGCACCGCCTAC

SEQ ID NO: 4-Comparator protein "N236A/C248A"
DKTHTCPPCP APELLGGPSV FLFPPKPKDT LMISRTPEVT CVVVDVSHED PEVKFNWYVD
GVEVHNAKTK PREEQYNSTY RVVSVLTVCL QDWLNGKEYK CKVSNKALPA PIEKTISKAK
GQPREPQVYT LPPSREEMTK NQVSLTCLVK GFYPSDIAVE WESNGQPENN YKTTPPVLDS
DGSFFLYSKL TVDKSRWQQG NVFSCSVMHE ALHNHYTQKS LSLSPGKLVL GPPLYAVSLV
MSDTAGTAY
```

-continued

| Sequence information |
| --- |

SEQ ID NO: 5-DNA sequence of the comparator protein "N236A/C248A"
GACAAAACTCACACATGCCCACCGTGCCCAGCACCTGAACTCCTGGGGGGACCGTCAGTCTTCCTCTTCCCCC
CAAAACCCAAGGACACCCTCATGATCTCCCGGACCCCTGAGGTCACATGCGTGGTGGTGGACGTGAGCCACGA
AGACCCTGAGGTCAAGTTCAACTGGTACGTGGACGGCGTGGAGGTGCATAATGCCAAGACAAAGCCGCGGGAG
GAGCAGTACAACAGCACGTACCGTGTGGTCAGCGTCCTCACCGTCTGCCTCCAGGACTGGCTGAATGGCAAGG
AGTACAAGTGCAAGGTCTCCAACAAAGCCCTCCCAGCCCCCATCGAGAAAACCATCTCCAAAGCCAAAGGGCA
GCCCCGAGAACCACAGGTGTACACCCTGCCCCCATCCCGGGAGGAGATGACCAAGAACCAGGTCAGCCTGACC
TGCCTGGTCAAAGGCTTCTATCCCAGCGACATCGCCGTGGAGTGGGAGAGCAATGGGCAGCCGGAGAACAACT
ACAAGACCACGCCTCCCGTGCTGGACTCCGACGGCTCCTTCTTCCTCTACAGCAAGCTCACCGTGGACAAGAG
CAGGTGGCAGCAGGGGAACGTCTTCTCATGCTCCGTGATGCACGAGGCTCTGCACAACCACTACACGCAGAAG
AGCCTCTCCCTGTCTCCGGGTAAATTAGTCCTAGGACCCCCCCTGTACGCCGTGTCCCTGGTCATGTCCGACA
CAGCTGGCACCGCCTAC SEQ ID NO: 6-Comparator protein "L448STOP"
DKTHTCPPCP APELLGGPSV FLFPPKPKDT LMISRTPEVT CVVVDVSHED PEVKFNWYVD
GVEVHNAKTK PREEQYNSTY RVVSVLTVCL QDWLNGKEYK CKVSNKALPA PIEKTISKAK
GQPREPQVYT LPPSREEMTK NQVSLTCLVK GFYPSDIAVE WESNGQPENN YKTTPPVLDS
DGSFFLYSKL TVDKSRWQQG NVFSCSVMHE ALHNHYTQKS LSLSPGK*****

SEQ ID NO: 7-DNA sequence of the comparator protein "L448STOP"
GACAAAACTCACACATGCCCACCGTGCCCAGCACCTGAACTCCTGGGGGGACCGTCAGTCTTCCTCTTCCCCC
CAAAACCCAAGGACACCCTCATGATCTCCCGGACCCCTGAGGTCACATGCGTGGTGGTGGACGTGAGCCACGA
AGACCCTGAGGTCAAGTTCAACTGGTACGTGGACGGCGTGGAGGTGCATAATGCCAAGACAAAGCCGCGGGAG
GAGCAGTACAACAGCACGTACCGTGTGGTCAGCGTCCTCACCGTCTGCCTCCAGGACTGGCTGAATGGCAAGG
AGTACAAGTGCAAGGTCTCCAACAAAGCCCTCCCAGCCCCCATCGAGAAAACCATCTCCAAAGCCAAAGGGCA
GCCCCGAGAACCACAGGTGTACACCCTGCCCCCATCCCGGGAGGAGATGACCAAGAACCAGGTCAGCCTGACC
TGCCTGGTCAAAGGCTTCTATCCCAGCGACATCGCCGTGGAGTGGGAGAGCAATGGGCAGCCGGAGAACAACT
ACAAGACCACGCCTCCCGTGCTGGACTCCGACGGCTCCTTCTTCCTCTACAGCAAGCTCACCGTGGACAAGAG
CAGGTGGCAGCAGGGGAACGTCTTCTCATGCTCCGTGATGCACGAGGCTCTGCACAACCACTACACGCAGAAG
AGCCTCTCCCTGTCTCCGGGTAAATGAGTCCTAGGACCCCCCCTGTACAACGTGTCCCTGGTCATGTCCGACA
CAGCTGGCACCTGCTACT SEQ ID NO: 17-Protein of the invention with additional glycosylation site in the hinge region (also referred to as "D1N/C248A" or "D221N/C575A")
NKTHTCPPCP APELLGGPSV FLFPPKPKDT LMISRTPEVT CVVVDVSHED PEVKFNWYVD
GVEVHNAKTK PREEQYNSTY RVVSVLTVCL QDWLNGKEYK CKVSNKALPA PIEKTISKAK
GQPREPQVYT LPPSREEMTK NQVSLTCLVK GFYPSDIAVE WESNGQPENN YKTTPPVLDS
DGSFFLYSKL TVDKSRWQQG NVFSCSVMHE ALHNHYTQKS LSLSPGKLVL GPPLYNVSLV
MSDTAGTAY

The invention claimed is:

1. A protein comprising two chimeric polypeptide chains, wherein each chimeric polypeptide chain comprises an Fc receptor binding portion comprising:

two immunoglobulin G heavy chain constant regions wherein at least one of the two immunoglobulin heavy chain constant regions is adapted by introduction of an artificial glycosylation site at a position corresponding to residue 1 of SEQ ID NO: 1; and an immunoglobulin tailpiece, and wherein the amino acid sequence and glycosylation of the immunoglobulin tailpiece region are adapted, as compared to the tailpiece of a wild-type immunoglobulin, by loss of the cysteine residue corresponding to residue 248 of SEQ ID NO: 1 to inhibit polymerisation of the protein.

2. A protein according to claim 1, wherein the cysteine residue is replaced with an alanine residue.

3. A protein according to claim 1, further comprising loss of a cysteine residue corresponding to residue 89 of SEQ ID NO:1.

4. A protein according to claim 1, wherein glycans attached to glycosylation sites of the protein are larger than those found on a control protein.

5. A protein according to claim 1, wherein a proportion of glycans that terminate in sialic acid is larger than the proportion of such glycans found on a control protein.

6. A protein according to claim 1, wherein the immunoglobulin tailpiece is based upon a tailpiece of an immunoglobulin selected from the group consisting of: IgM, IgA, and IgE.

7. A protein according to claim 6, wherein the tailpiece shares at least 70% identity with amino acid residues 232-249 of SEQ ID NO:2.

8. A protein according to claim 1, wherein the immunoglobulin G heavy chain constant regions are derived from an immunoglobulin selected from the group consisting of: IgG1; IgG2; IgG3; and IgG4.

9. A protein according to claim 1 comprising SEQ ID NO: 17.

10. A protein according to claim 1, wherein at least 95% of the protein is incorporated in a composition in monomeric form.

11. A method of preventing or treating an autoimmune or inflammatory disease, the method comprising providing a therapeutically effective amount of a protein comprising two chimeric polypeptide chains to a subject in need of such prevention or treatment, wherein each chimeric polypeptide chain comprises an Fc receptor binding portion comprising:

two immunoglobulin G heavy chain constant regions wherein at least one of the two immunoglobulin heavy chain constant regions is adapted by introduction of an artificial glycosylation site at a position corresponding to residue 1 of SEQ ID NO: 1; and an immunoglobulin tailpiece region, and wherein the amino acid sequence and glycosylation of the immunoglobulin tailpiece region are adapted, as compared to the tailpiece of a wild-type immunoglobulin, by loss of the cysteine residue corresponding to residue 248 of SEQ ID NO: 1 to inhibit polymerisation of the protein.

12. A method according to claim 11, wherein the protein is provided in intravenous immunoglobulin (IVIG) or subcutaneous immunoglobulin (SCIG) therapy.

13. A method according to claim 11 wherein the therapeutically effective amount of the protein is provided as a vaccine.

14. A method according to claim 13, wherein the protein is conjugated to an immune modulator.

15. A method according to claim 11 wherein the disease is mediated through binding of sialic acid-dependent receptors.

16. A method according to claim 11, wherein the protein comprises SEQ ID NO: 17.

17. A method according to claim 11, wherein the autoimmune or inflammatory-disease is selected from the group consisting of: autoimmune cytopenias, Guillain-Barré syndrome, myasthenia gravis, anti-Factor VIII autoimmune disease, dermatomyositis, vasculitis, and uveitis.

* * * * *